(12) United States Patent
Li et al.

(10) Patent No.: US 6,632,425 B1
(45) Date of Patent: *Oct. 14, 2003

(54) CHEMOKINE COMPOSITIONS

(75) Inventors: Yuling Li, Germantown, MD (US);
Mark Oelkuct, Frederick, MD (US);
Reiner L. Gentz, Rockville, MD (US)

(73) Assignee: Human Genome Sciences, Inc., Rockville, MD (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 6 days.

This patent is subject to a terminal disclaimer.

(21) Appl. No.: 09/215,160
(22) Filed: Dec. 18, 1998

Related U.S. Application Data

(62) Division of application No. 08/821,637, filed on Mar. 20, 1997, now Pat. No. 5,912,327.

(51) Int. Cl.[7] .................. A61K 45/00; C07K 14/00; C07K 19/52
(52) U.S. Cl. .................. 424/85.1; 530/300; 530/351
(58) Field of Search ............................... 530/300, 351; 424/85.1

(56) References Cited

U.S. PATENT DOCUMENTS

| | | | |
|---|---|---|---|
| 4,569,790 A | | 2/1986 | Koths et al. ............ 260/112 R |
| 4,705,848 A | | 11/1987 | Yang et al. .................. 530/399 |
| 4,880,788 A | * | 11/1989 | Moake et al. ................ 514/150 |
| 5,288,931 A | | 2/1994 | Chang et al. ................ 530/399 |
| 5,474,983 A | * | 12/1995 | Kuna et al. ..................... 514/2 |
| 5,504,003 A | * | 4/1996 | Li et al. .................. 435/240.2 |
| 5,556,767 A | | 9/1996 | Rosen et al. ................ 435/69.1 |
| 5,633,149 A | * | 5/1997 | Guegler et al. ............ 435/69.5 |
| 6,001,606 A | * | 12/1999 | Ruben et al. .............. 435/69.5 |
| 6,165,459 A | * | 12/2000 | Broxmeyer et al. ....... 424/85.2 |

FOREIGN PATENT DOCUMENTS

| | | |
|---|---|---|
| EP | 0 215 625 | 3/1987 |
| EP | 0 432 419 | 6/1991 |
| EP | 0 807 439 A2 | 11/1997 |
| WO | WO 95/17092 | 6/1995 |
| WO | WO 96/34891 | 11/1996 |
| WO | WO 96/39508 | 12/1996 |
| WO | WO 96/39521 | 12/1996 |
| WO | WO 97/15594 | 5/1997 |
| WO | WO 98/14582 | 4/1998 |
| WO | WO 98/24908 | 6/1998 |
| WO | WO 98/44117 | 10/1998 |

OTHER PUBLICATIONS

Bailey, S.M., and Meagher, M.M., "Chaotropic Agent–Enhanced Homogenization of *E. Coli*," Abstract of Papers, 207th ACS National Meeting, Abstract No. 223 (1994).

Bailey, S.M., et al., "Improved Homogenization of Recombinant *Escherichia coli* following Pretreatment with Guanidine Hydrochloride," *Biotechnol. Prog.* 11:533–539 (1995).

Fischer, B.E., "Renaturation of Recombinant Proteins Produced as Inclusion Bodies," *Biotech Adv.* 12:89–101 (1994).

Hart, R.A., and Bailey, J.E., "Solubilization and Regeneration of *Vitreoscilla* Hemoglobin Isolated from Protein Inclusion Bodies," *Biotechnol. and Bioeng.* 39:1112–1120 (1992).

Meagher, M.M., et al., "Extraction of rIL–2 Inclusion Bodies from *Escherichia coli* Using Cross–Flow Filtration," *Biotech. Bioeng.* 43:969–977 (1994).

Mikulski, A.J., et al., "Large–Scale Purification of Human Fibroblast Interferon by Tandem Chromatography," *Curr. Chemother. Infect. Dis., Proc. 11th Int. Congr. Chemother. and 19th Intersci. Conf. Antimicrob. Agents Chemother.* II:1746–1747 (1980).

Mikulski, A.J., et al., "Large–scale purification of human fibroblast interferon by tandem chromatography," *Chem. Abstr.* 93:21875 (1980).

Patel, V.P., et al., "Molecular and Functional Characterization of Two Novel Human C–C Chemokines as Inhibitors of Two Distinct Classes of Myeloid Progenitors," *J. Exp. Med.* 185:1163–1172 (Apr. 1997).

Patel, V.P., et al., "Molecular and functional characterization of two novel human C–C chemokines as inhibitors of two distinct classes of myeloid progenitors," *Chem. Abstr.* 126:316141 (Jun. 1997).

Proost, P., et al., "Purification and Identification of Natural Chemokines," *Methods* 10:82–92 (Aug. 1996).

Proost, P., et al., "Purification and identification of natural chemokines," *Chem. Abstr.* 125:165230 (Sep. 1996).

Tsuji, T., et al., "Characterization of Disulfide Bonds in Recombinant Proteins: Reduced Human Interleukin 2 in Inclusion Bodies and Its Oxidative Refolding," *Biochem.* 26:3129–3134 (1987).

Vandenbroeck, K., et al., "Refolding and single–step purification of porcine interferon–γ from *Escherichia coli* inclusion bodies, Conditions for reconstitution of dimeric IFN–γ," *Eur. J. Biochem.* 215:481–486 (1993).

Weir, M.P., and Sparks, J., "Purification and renaturation of recombinant human interleukin–2," *Biochem. J.* 245:85–91 (1987).

* cited by examiner

Primary Examiner—Yvonne Eyler
Assistant Examiner—Joseph F. Murphy
(74) Attorney, Agent, or Firm—Human Genome Sciences, Inc.

(57) ABSTRACT

The present invention relates to processes for the purification of proteins. More specifically, methods for solubilizing and purifying proteins expressed in an insoluble form using low concentrations of chaotropic agents, such as guanidine salts, are provided. Also provided are methods for refolding proteins solubilized according to the present invention.

15 Claims, 32 Drawing Sheets

SEQUENCE LISTING (1) GENERAL INFORMATION:

(iii) NUMBER OF SEQUENCES: 5

(2) INFORMATION FOR SEQ ID NO:1:

(i) SEQUENCE CHARACTERISTICS:
      (A) LENGTH: 5 amino acids
      (B) TYPE: amino acid
      (C) STRANDEDNESS: single
      (D) TOPOLOGY: Not Relevant (ii) MOLECULE TYPE: peptide (xi) SEQUENCE DESCRIPTION: SEQ ID NO:1:

Met Gln Gly Glu Asn
1            5

(2) INFORMATION FOR SEQ ID NO:2:

(i) SEQUENCE CHARACTERISTICS:
      (A) LENGTH: 5 amino acids
      (B) TYPE: amino acid
      (C) STRANDEDNESS: single
      (D) TOPOLOGY: Not Relevant (ii) MOLECULE TYPE: peptide (xi) SEQUENCE DESCRIPTION: SEQ ID NO:2:

Thr Asp Gln Leu Ser
1            5

(2) INFORMATION FOR SEQ ID NO:3:

(i) SEQUENCE CHARACTERISTICS:
        (A) LENGTH: 216 amino acids
        (B) TYPE: amino acid
        (C) STRANDEDNESS: single
        (D) TOPOLOGY: Not Relevant (ii) MOLECULE TYPE: protein (xi) SEQUENCE DESCRIPTION: SEQ ID NO:3:

```
Met Gly Ala Ala Arg Leu Leu Pro Asn Leu Thr Leu Cys Leu Gln Leu
 1               5                  10                  15

Leu Ile Leu Cys Cys Gln Thr Gln Gly Glu Asn His Pro Ser Pro Asn
            20                  25                  30

Phe Asn Gln Tyr Val Arg Asp Gln Gly Ala Met Thr Asp Gln Leu Ser
            35                  40                  45

Arg Arg Gln Ile Arg Glu Tyr Gln Leu Tyr Ser Arg Thr Ser Gly Lys
        50                  55                  60

His Val Gln Val Pro Gly Arg Arg Ile Ser Ala Thr Ala Glu Asp Gly
65                  70                  75                  80

Asn Lys Phe Ala Lys Leu Ile Val Glu Thr Asp Thr Phe Gly Ser Arg
                85                  90                  95

Val Arg Ile Lys Gly Ala Glu Ser Glu Lys Tyr Ile Cys Met Asn Lys
                100                 105                 110

Arg Gly Lys Leu Ile Gly Lys Pro Ser Gly Lys Ser Lys Asp Cys Val
            115                 120                 125

Phe Thr Glu Ile Val Leu Glu Asn Asn Tyr Thr Ala Phe Gln Asn Ala
130                 135                 140

Arg His Glu Gly Trp Phe Met Val Phe Thr Arg Gln Gly Arg Pro Arg
145                 150                 155                 160

Gln Ala Ser Arg Ser Arg Gln Asn Gln Arg Glu Ala His Phe Ile Lys
                165                 170                 175

Arg Leu Tyr Gln Gly Gln Leu Pro Phe Pro Asn His Ala Glu Lys Gln
            180                 185                 190

Lys Gln Phe Glu Phe Val Gly Ser Ala Pro Thr Arg Arg Thr Lys Arg
        195                 200                 205

Thr Arg Arg Pro Gln Leu Pro Thr
    210                 215
```

(2) INFORMATION FOR SEQ ID NO:4:

(i) SEQUENCE CHARACTERISTICS:
        (A) LENGTH: 7 amino acids
        (B) TYPE: amino acid
        (C) STRANDEDNESS: single
        (D) TOPOLOGY: Not Relevant (ii) MOLECULE TYPE: peptide (xi) SEQUENCE DESCRIPTION: SEQ ID NO:4:

```
Arg Val Thr Lys Asp Ala Glu
 1               5
```

(2) INFORMATION FOR SEQ ID NO:5:

(i) SEQUENCE CHARACTERISTICS:
        (A) LENGTH: 8 amino acids
        (B) TYPE: amino acid
        (C) STRANDEDNESS: single
        (D) TOPOLOGY: Not Relevant

```
    (ii) MOLECULE TYPE: peptide (xi) SEQUENCE DESCRIPTION: SEQ ID NO:5:

Arg Val Thr Lys Asp Ala Glu Thr
1               5
```

CHEMOKINE COMPOSITIONS

The present application is a divisional of U.S. application Ser. No. 08/821,637, filed Mar. 20, 1997, now U.S. Pat No. 5,912,327, the disclosure of which is incorporated by reference.

BACKGROUND OF THE INVENTION

1. Field of the Invention

The present invention relates to processes for the purification of proteins. More specifically, methods for solubilizing and purifying proteins expressed in an insoluble form using low concentrations of chaotropic agents, such as guanidine salts, are provided. Also provided are methods for refolding proteins solubilized according to the present invention.

2. Related Art

The advent of recombinant DNA technology has brought about an entirely new generation of protein products. The ability to clone and express proteins in bacteria, yeast and mammalian cells has made it possible to produce therapeutics and industrially important proteins at economically feasible levels. However, the expression of high levels of recombinant proteins in *Escherichia coli* often results in the formation of inactive, denatured protein that accumulates in intracellular aggregates known as insoluble inclusion bodies. (Krueger et al., "Inclusion bodies from proteins produced at high levels in *Escherichia coli*," in *Protein Folding*, L. M. Gierasch and P. King (Eds), Am. Ass. Adv. Sci., 136–142 (1990); Marston, *Biochem. J.*, 240:1–12 (1986); Mitraki, et al., *Bio/Technol.* 7:800–807 (1989); Schein, *Bio/Technol.* 7:1141–1147 (1989); Taylor, et al., *Bio/Technol.* 4:553–557 (1986)). Inclusion bodies are dense aggregates, which are 2–3 $\mu$m in diameter and largely composed of recombinant protein, that can be separated from soluble bacterial proteins by low-speed centrifugation after cell lysis (Schoner, et al. *Biotechnology* 3:151–154 (1985)).

The recovery of recombinantly expressed protein in the form of inclusion bodies has presented a number of problems. First, although the inclusion bodies contain a large percentage of the recombinantly produced protein, additional contaminating proteins must be removed in order to isolate the protein of interest Second, the proteins localized in inclusion bodies are in a form that is not biologically active, presumably due to incorrect folding.

Several methods have been developed to obtain active proteins from inclusion bodies. These strategies include the separation and purification of inclusion bodies from other cellular components, solubilization and reduction of the insoluble material, purification of solubilized proteins and ultimately renaturation of the proteins and generation of native disulfide bonds. The art teaches that concentrations of 6 M or greater of chaotropic agents, such as guanidine hydrochloride, guanidine isothiocyanate or urea are necessary for solubilization of the insoluble recombinant polypeptides from the inclusion bodies. See, for example, Vandenbroeck et al., *Eur. J Biochem.* 215:481–486 (1993); Meagher et al., *Biotech. Bioeng.* 43:969–977 (1994); Yang et al., U.S. Pat. No. 4,705,848, issued Nov. 10, 1987; Weir et al., *Biochem. J.* 245:85–91 (1987); and Fischer, *Biotech. Adv.* 12:89–101 (1994).

Contrary to the teachings of the prior art, the inventors have discovered that low concentrations of guanidine salts can be used to solubilize biologically active (i.e., correctly folded) proteins and extract this population of the protein from a heterogeneous protein mixture localized in inclusion bodies. The methods disclosed herein are particularly useful for the purification of chemokines.

SUMMARY OF THE INVENTION

The present invention relates to the use of low concentrations of guanidine salts to solubilize inclusion bodies comprising target proteins. The purification method of the present invention results in a highly homogeneous product with no aggregated form of the target protein and can be easily scaled up and adapted for cGMP manufacturing. Further, the recovered product has a high purity, extremely low endotoxin levels as well as low levels of residual DNA.

According to the invention, inclusion bodies are released from cells by lysis, optionally washed to remove cellular components prior to extraction, and extracted with solutions containing low concentrations of guanidine salts.

More specifically, the invention provides for methods for solubilizing inclusion bodies by treatment with guanidine salts at concentrations of about 0.7 to about 3.5 M. The present invention also provides methods for solubilizing inclusion bodies by treatment with guanidine salts at concentrations of about 1 to about 2 M.

In another aspect, methods are provided for refolding target proteins which have been solubilized using guanidine salts. These methods involve the rapid dilution of guanidine salt extracts and optionally employ agents which facilitate target protein refolding. The invention further relates to the purification of solubilized target proteins using tandem column techniques.

The methods of the invention have the advantage of offering uniformity of equipment requirements for any desired product. While conditions required for optimum efficiency of solubilization and refolding will vary with each protein, the present invention is applicable, with only minor modification, for any protein which forms inclusion bodies. The modifications required to achieve optimum solubilization and refolding conditions for specific proteins are disclosed herein or are will be readily apparent to the skilled artisan after reading the present specification.

DETAILED DESCRIPTION OF THE INVENTION

Figure 1:
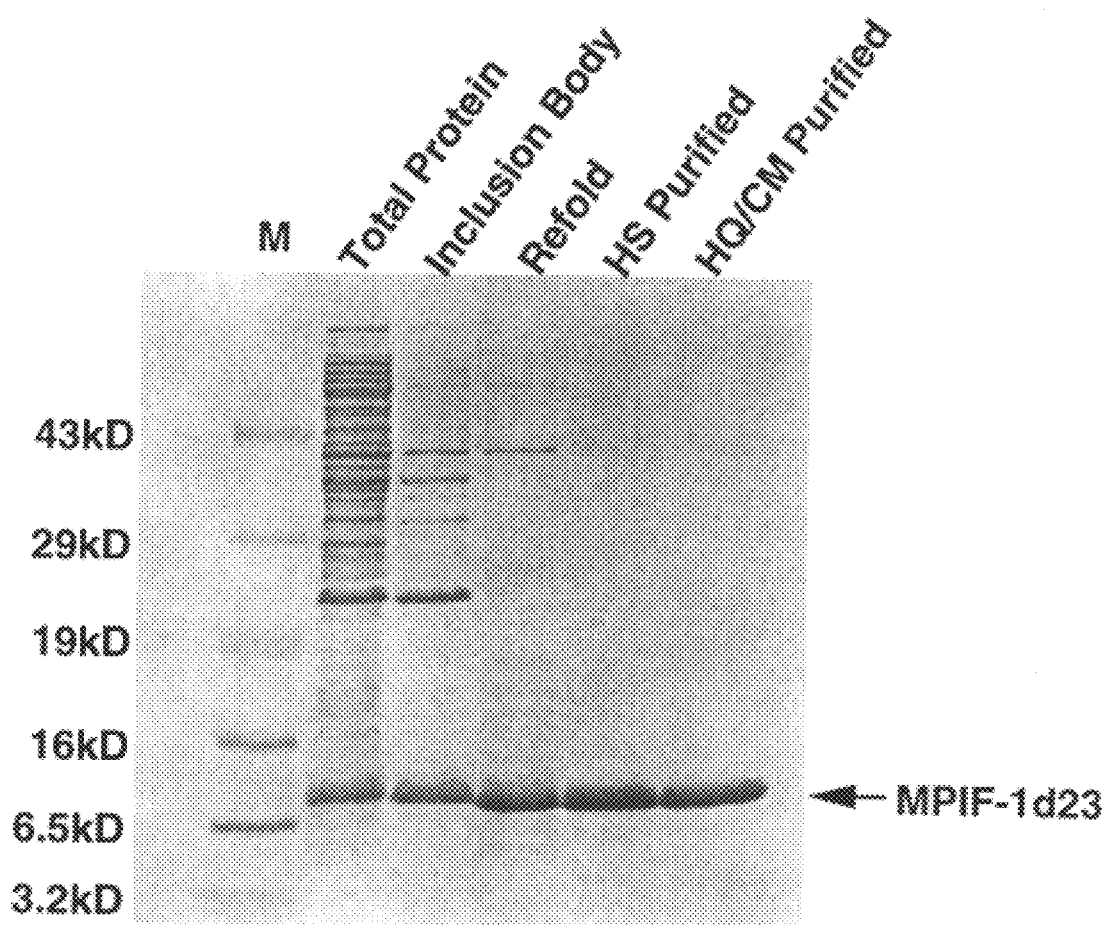
FIG. 1. SDS-PAGE analysis of in process samples of MPIF-1d23 under reducing conditions. The gel was stained with Coomassie blue. Lane 1 shows the molecular weight standards. Lane 2: Total protein from IPTG induced MPIF-1d23 transformed *E. coli*. Lane 3: Inclusion body. Lane 4: 0.16 $\mu$m filtered refold. Lane 5: HS purified MPIF-1d23. Lane 6: HQ/CM purified MPIF-1d23.
Figure 2:
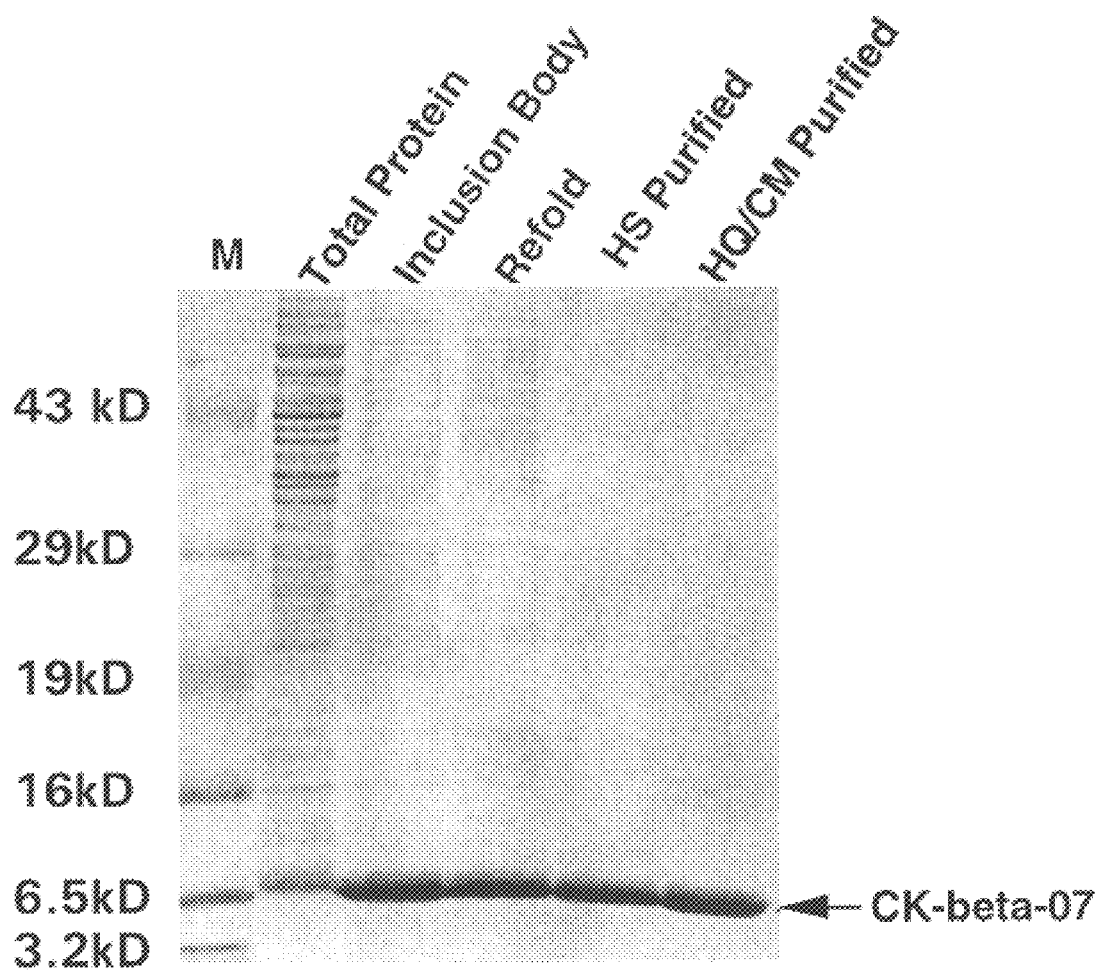
FIG. 2. SDS-PAGE analysis of in process samples of MIP-4 (CK-beta-07) under reducing conditions. The gel was stained with Coomassie blue. Lane 1 shows the molecular weight standards. Lane 2: Total protein from IPTG induced MIP-4 (CK-beta-07) transformed *E. coli*. Lane 3: Inclusion body. Lane 4: 0.16 $\mu$m filtered refold. Lane 5: HS purified MIP4 (CK-beta-07). Lane 6: HQ/CM purified MIP-4 (CK-beta-07).
Figure 3:
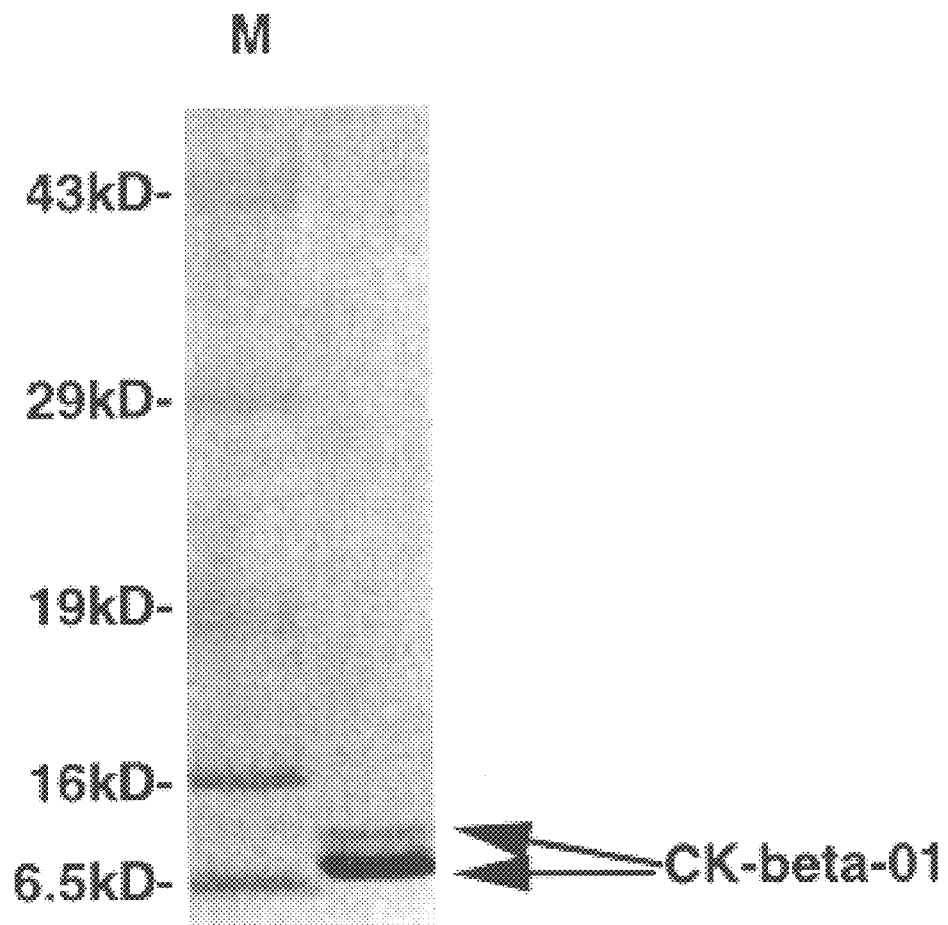
FIG. 3. SDS-PAGE analysis of 5 $\mu$g purified MCIF-1 under reducing conditions. The gel was stained with Coomassie blue. Lane 1 shows the molecular weight standards.
Figure 4:
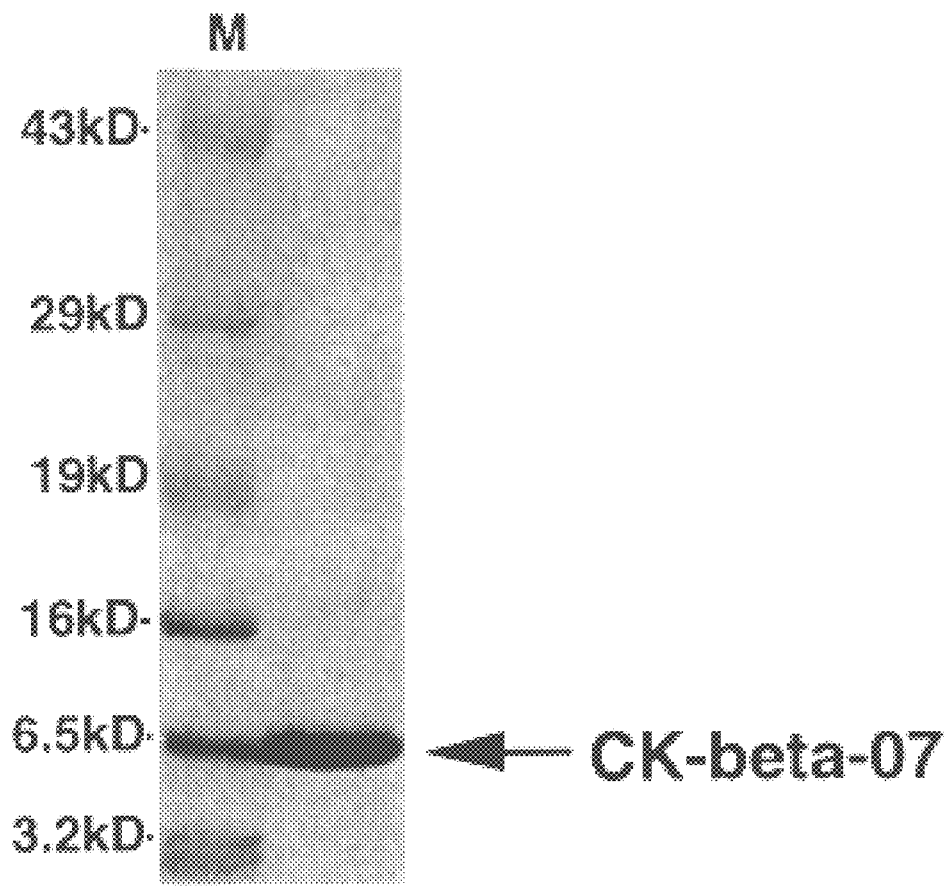
FIG. 4. SDS-PAGE analysis of 5 $\mu$g purified MIP-4 (CK-beta-07) under reducing conditions. The gel was stained with Coomassie blue. Lane 1 shows the molecular weight standards.
Figure 5:
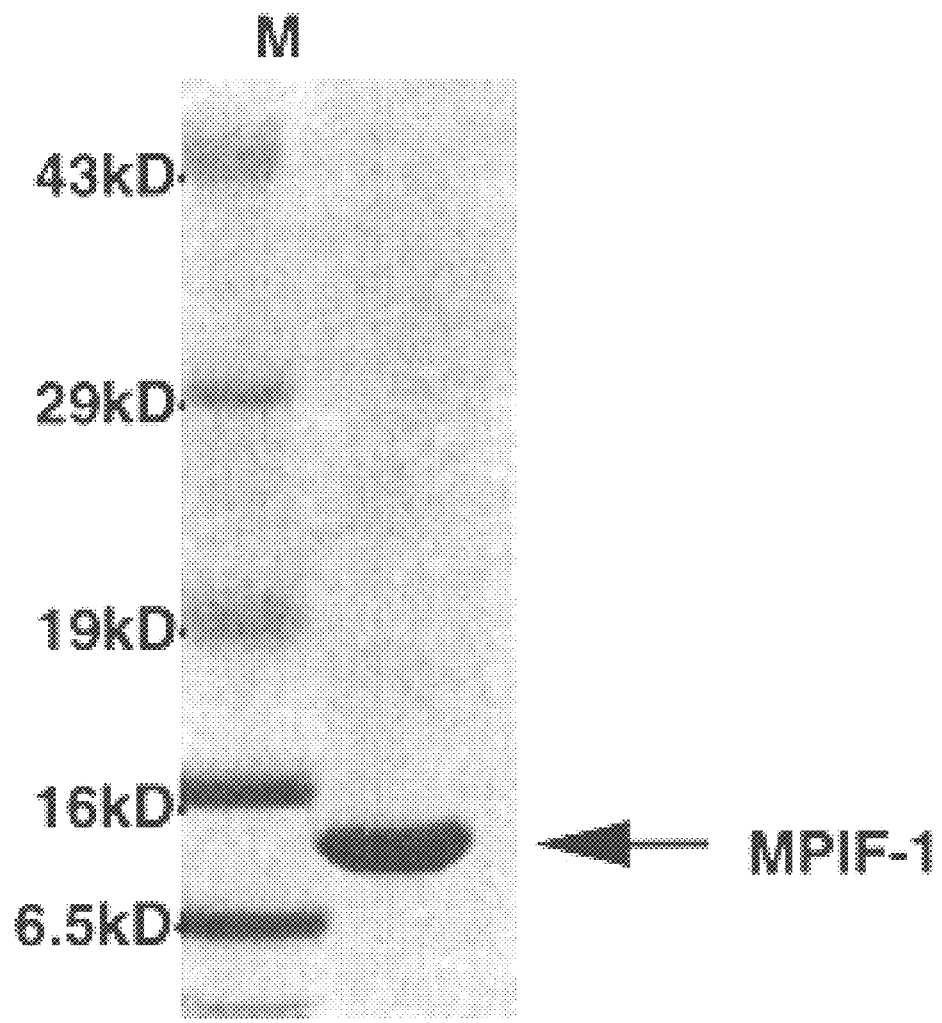
FIG. 5. SDS-PAGE analysis of 5 $\mu$g purified MPIF-1 under reducing conditions. The gel was stained with Coomassie blue. Lane 1 shows the molecular weight standards.
Figure 6:
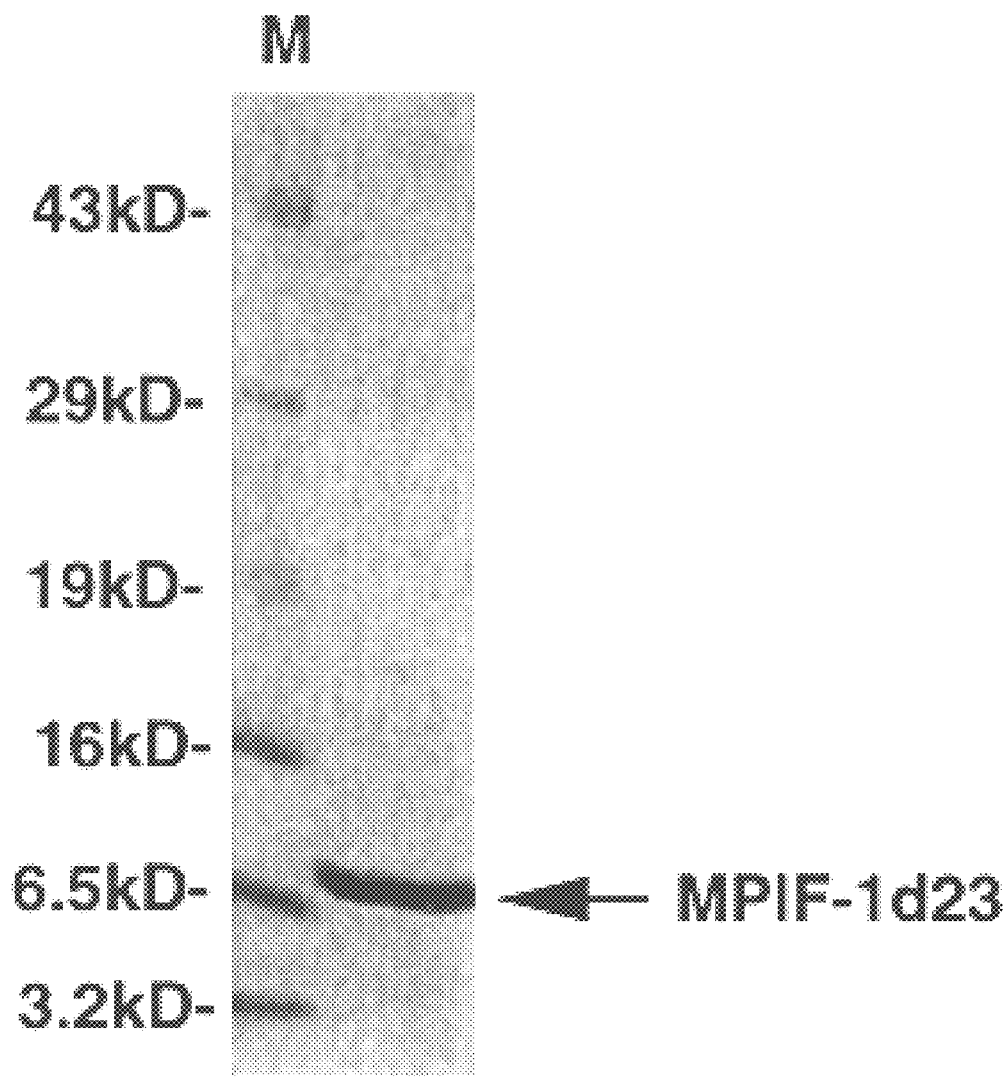
FIG. 6. SDS-PAGE analysis of 5 µg purified MPIF-1d23 under reducing conditions. The gel was stained with Coomassie blue. Lane 1 shows the molecular weight standards.
Figure 7:
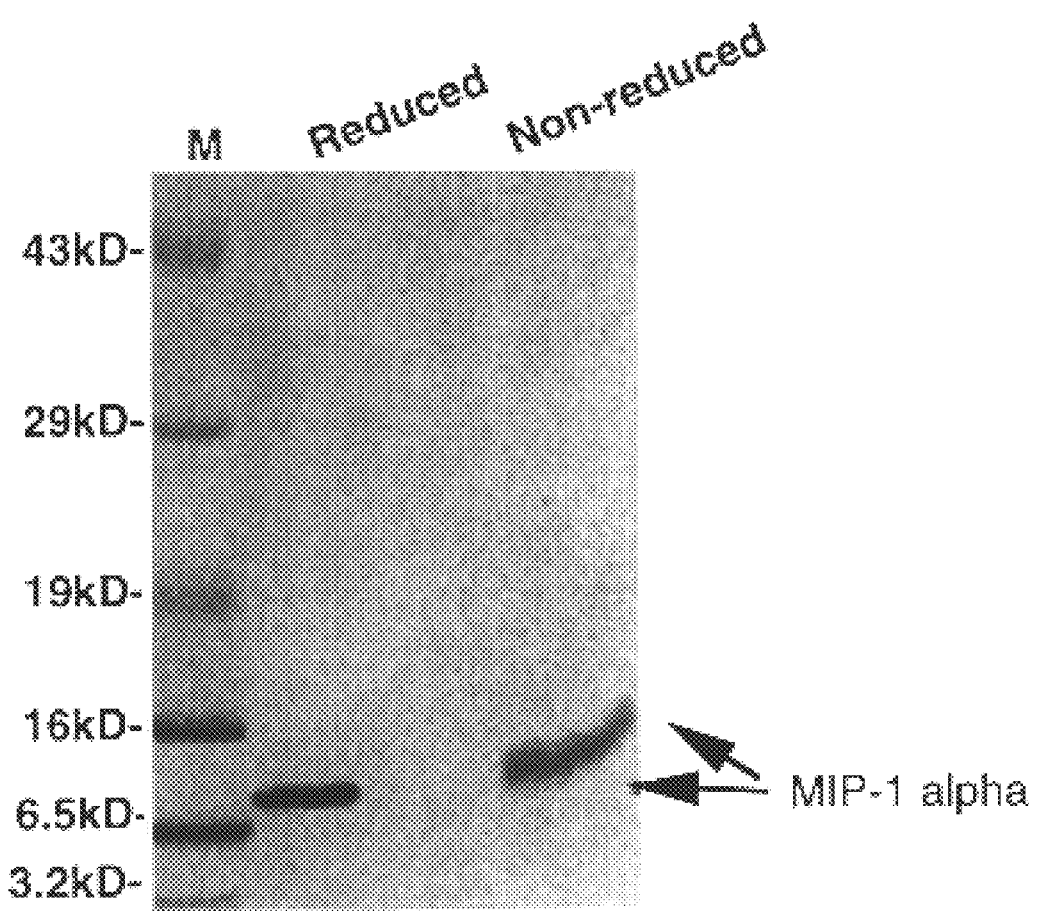
FIG. 7. SDS-PAGE analysis of 3 µg purified MIP-1 alpha. The gel was stained with Coomassie blue. Lane 1: Molecular weight standards. Lane 2: 3 µg MIP-1 alpha under reducing conditions. Lane 3: blank. Lane 4: 3 µg MIP-1 alpha under non-reducing conditions.
Figure 8:
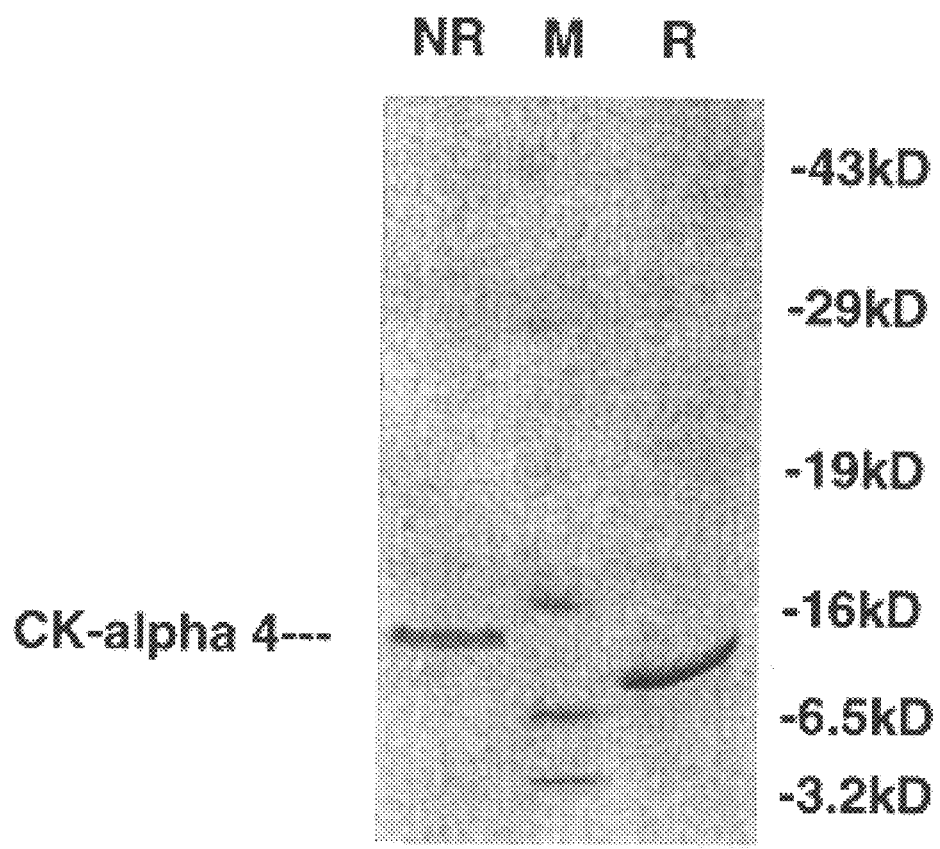
FIG. 8. SDS-PAGE analysis of 5 µg purified CK-alpha-04 under reducing conditions. The gel was stained with Coomassie blue. Lane 1 shows the molecular weight standards.

The present invention provides solubilization and refolding procedures which are applicable to recombinant proteins that form inclusion bodies. The present invention provides methods which employ low concentrations of guanidine salts (e.g., about 0.7 to about 3.5 M) to solubilize active protein from inclusion bodies which is contrary to the teachings of the prior art that concentrations of 6–8 M guanidine salt are necessary for such solubilization. As indicated above, the advantages of using the methods of the present invention for the purification of target proteins are that it is simple, low in cost, can be easily scaled for use with large volumes and adapted for cGMP manufacturing. Further, the present invention results in a highly homogeneous biologically active product having high purity, low residual DNA levels and extremely low endotoxin levels with no aggregated forms of the target protein.

By "target protein" is intended secreted recombinant protein or a recombinant protein localized in an inclusion body which is the subject of a purification procedure.

In another aspect, by "target protein" is intended secreted endogenous protein or endogeous protein localized in an inclusion body wherein the endogenous protein's natural expression characteristics have been modified using homologous recombination. By "endogenous" protein is intended protein expressed from a gene naturally occurring in the genome of a cell. Expressing protein using homologous recombination, which is described in detail in U.S. Pat. No. 5,272,071, WO 90/11354, WO91/06666, WO 91/06667, and WO 95/31560 (each of which are herein incorporated by reference), occurs without transfecting a cell with DNA that encodes the protein of interest. Instead, the gene is identified within the cell's genome and activated by inserting an appropriate regulatory segment by homologous recombination such that the regulatory segment is operatively linked to the gene and thereby modifies its expression. Positive and/or negative selectable markers can also be inserted to aid in selection of cells wherein the proper homologous recombination events have occurred. As an additional embodiment, such naturally occurring genes can be amplified for enhanced protein expression, whether the gene is normally transcriptionally silent and has been activated by the integrated regulatory segment, or endogenously expresses product.

By "refolded" is intended that a conformational form has been produced that exhibits at least one biological activity of the protein. Preferably, protein purified according to the present is refolded to its native conformation.

By "recombinant protein" is intended protein expressed in a host cell from a recombinant nucleic acid molecule.

By "inclusion body" is intended an insoluble protein aggregate produced by a microorganism (e.g., a bacterium) or other host cell (e.g., an insect or mammalian host cell). Examples of inclusion bodies are recombinantly expressed proteins.

By "biological activity" is intended an activity normally associated with a protein. For example, chemokines (intercrine cytokines) exhibit a wide variety of biological activities. A hallmark feature is their ability to elicit chemotactic migration of distinct cell types, including monocytes, neutrophils, T lymphocytes, basophils and fibroblasts. Many chemokines also have proinflammatory activity and are involved in multiple steps during an inflammatory reaction. These activities include stimulation of histamine release, lysosomal enzyme and leukotriene release, increased adherence of target immune cells to endothelial cells, enhanced binding of complement proteins, induced expression of granulocyte adhesion molecules and complement receptors, and respiratory burst. Certain chemokines have also been shown to exhibit other activities such as suppressing hematopoietic stem cell proliferation, inhibiting endothelial cell growth, and proliferating keratinocytes. Of course, activities normally associated with a vast number of other proteins are known in the art.

In one aspect, the invention provides a method for recovering a target protein from inclusion bodies which involves (1) treating inclusion bodies from lysed host cells with about 0.7 to about 3.5 M chaotropic agent to solubilize the protein; and (2) recovering the protein. The recovered, solubilized protein may then be purified using conventional techniques. Optionally, if deemed necessary, the target protein may be refolded prior to purification.

Also provided by the present invention is a method for solubilizing protein localized in inclusion bodies using concentrations of guanidine salt of about 1 to about 2 M. As one skilled in the art would recognize, each individual protein will be solubilized at a particular guanidine salt concentration.

In another aspect of the present invention, a series of solubilization steps is provided to separate target proteins from host cell contaminants. Initially, the cells containing the target protein are lysed and the homogenate is centrifuged to pellet the inclusion bodies. Preferably, the pellet is then washed (e.g., with a buffer containing 50 mM Tris, 25 mM EDTA and 0.5 M NaCl) to separate the inclusion bodies from cellular components. The partially purified inclusion bodies are then solubilized with a solution containing a guanidine salt (e.g., 1.5 M for 24 hours). Solubilized target protein remains in the soluble phase after centrifugation (e.g., 7,000×g). The supernatant is placed at 2–10° C. overnight prior to the second centrifugation at 30,000×g. Optionally, the resulting pellet can be further extracted overnight followed by re-centrifugation (e.g., at 30,000×g). The 30,000×g supernatant is referred to as the guanidine salt extract which generally contains most of the target protein originally present in the inclusion bodies. The portion of the protein that remains in the pellet after such extraction is generally difficult to refold and not biologically active.

Non-limiting examples of the guanidine salts that can be used in the process of the invention include guanidine hydrochloride and guanidine isothiocyanate. Urea can also be used as the chaotropic agent instead of the guanidine salts at concentrations of about 1 to about 4 M. In addition, detergents may be used to solubilize the target protein.

The inventors have shown that the present invention provides solubilized, biologically active target protein of higher yield and better purity than the processes known in the prior art. When the recombinant proteins are produced in the bacterial cell, inclusion bodies are formed that are heterogeneous in protein components. This heterogeneity comprises many conformational forms of the target protein that range from those which are correctly folded, those which are partially correctly folded, and those which are completely incorrectly folded. It is likely that the forms of the target protein present in the inclusion bodies that are closest to the correct protein conformation will be solubilized more readily in lower concentrations of guanidine salts than will those forms that are less correctly folded.

Surprisingly, the present inventors have obtained substantially higher yields of active protein using the process of the present invention than that obtainable by methods taught by the art that require higher concentrations (6–8 M) of guanidine salts for the solubilization of the inclusion body protein. The methods taught by the art involving the use of high concentrations of chaotropic agents may yield more protein but, in contrast to the process of the present invention, most of the protein is in an inactive form.

Although target proteins purified using the methods of the present invention will generally be correctly folded, a certain population of the isolated target protein may not be in a completely proper conformation. Thus, the present invention also provides methods for refolding proteins solubilized in the presence of guanidine salts. These methods involve the rapid dilution of guanidine salt extracts containing the solubilized target protein. In one aspect of the present invention, the guanidine salt extracted target protein is refolded by rapidly mixing the guanidine salt extract with a large volume of a buffer containing little or no guanidine salt (e.g., 20 volumes of 50–100 mM sodium acetate pH 4.5, 150 mM sodium chloride, 2 mM EDTA).

After solubilization of inclusion bodies, the solubilized proteins may be present in reduced form and may not contain disulfide bonds found in the native protein. Several known methods for regenerating native sulfide bonds include air oxidation systems, glutathione renaturation systems, and renaturation using mixed sulfides. These methods are described in Fischer, B. Biotech. Adv. 12:8914 101 (1994), which is herein incorporated by reference.

Depending on the factors which contribute to the native conformation of the target protein, it may be desirable to refold the target protein either using a renaturing system or in the presence of a reagent which assists in the formation of the target protein's native conformation. Such reagents include reducing agents, oxidizing agents and salts. Examples of such agents include DTT, β-mercaptoethanol, glutathione, cysteamine and cysteine. Other such agents would be apparent to one skilled in the art. Concentrations and incubation conditions for the use of these agents with the present invention would also be apparent to one skilled in the art. Generally, however, when DTT is used it would a protein concentration of 100 µg/ml to 500 µg/ml of protein would be treated with 5–100 mM DTT for about 24 hours at 2–25° C. Similarly, when β-mercaptoethanol is used a concentration of 100 µg/ml to 300 µg/ml of protein may generally be treated with 10 mM–200 mM β-mercaptoethanol for about 24 hours at 2–25° C. Similarly, when glutathione is used a concentration of 100 µg/ml to 300 µg/ml of protein may generally be treated with 1–10 mM oxidized and 9–90 mM reduced glutathione for about 24 hours at 2–25° C. Thus, another aspect of the present invention provides methods for refolding target proteins in the presence of agents which aid in the formation of the protein's native conformation.

The methods of the present invention can be applied to solubilize and refold any target protein deposited in inclusion bodies (i.e., cytokines, growth factors, enzymes, transcription factors, etc.). Non-limiting examples of such proteins include fibroblast growth factor 13 (FGF13), myeloid progenitor inhibitory factor-1 (MPIF-1), myeloid progenitor inhibitory factor-1 having the N-terminal 23 amino acids deleted (MPIF-1d23), macrophage inhibitory protein-1α (MIP-1α), monocyte-colony inhibitory factor (M-CIF), macrophage inhibitory protein-4 (MIP-4), chemokine-α4 (ck-α4), chemokine β-13 (ck β-13).

After solubilization and, optionally, refolding of target proteins, these proteins can be recovered and purified by methods well known in the art including ammonium sulfate or ethanol precipitation, acid extraction, anion or cation exchange chromatography, phosphocellulose chromatography, hydrophobic interaction chromatography, reverse phase chromatography, affinity chromatography, hydroxylapatite chromatography and lectin chromatography. Most preferably, high performance liquid chromatography ("HPLC") is employed for purification.

Target proteins may be expressed in modified form, such as a fusion protein, and may include heterologous functional regions. For instance, a region of additional amino acids, particularly charged amino acids, may be added to the N-terminus or C-terminus of the target protein to improve stability and persistence in the host cell, during purification, or during subsequent handling and storage. Also, peptide moieties may be added to the target protein to facilitate purification. Such regions may be removed prior to final preparation of the target protein.

The present invention can also be used to purify His-tagged proteins produced in an insoluble form. The bacterial expression vector pQE9 (QIAGEN, Inc., 9259 Eton Avenue, Chatsworth, Calif., 91311) is one example of a vector which may be used to produce a target protein containing a His tag. A DNA sequence encoding a target protein can be inserted into this vector such that the inserted sequence expresses the target protein with the His residues covalently linked to the amino terminus of the protein. These histidine residues allow for the affinity purification of the target protein using a nickel-nitrilo-tri-acetic acid ("Ni-NTA") affinity resin.

Vectors and Host Cells for Expression of Target Protein

Recombinant constructs for the expression of target protein may be introduced into host cells using well known techniques such as infection, transduction, transfection, transvection, electroporation and transformation. The vector may be, for example, a phage, plasmid, viral or retroviral vector. Retroviral vectors may be replication competent or replication defective. In the latter case, viral propagation generally will occur only in complementing host cells.

The polynucleotides encoding the target protein may be joined to a vector containing a selectable marker for propagation in a host. Generally, a plasmid vector is introduced in a precipitate, such as a calcium phosphate precipitate, or in a complex with a charged lipid. If the vector is a virus, it may be packaged in vitro using an appropriate packaging cell line and then transduced into host cells.

Preferred are vectors comprising cis-acting control regions to the polynucleotide of interest. Appropriate trans-acting factors may be supplied by the host, supplied by a complementing vector or supplied by the vector itself upon introduction into the host.

Vectors that provide for specific expression, include those that may be inducible and/or cell type-specific. Particularly preferred among such vectors are those inducible by environmental factors that are easy to manipulate, such as temperature and nutrient additives.

Expression vectors useful for the expression of target proteins include chromosomal-, episomal- and virus-derived vectors, e.g., vectors derived from bacterial plasmids, bacteriophage, yeast episomes, yeast chromosomal elements, viruses such as baculoviruses, papova viruses, vaccinia viruses, adenoviruses, fowl pox viruses, pseudorabies viruses and retroviruses, and vectors derived from combinations thereof, such as cosmids and phagemids.

The DNA insert containing the gene for the target protein should be operatively linked to an appropriate promoter, such as the phage lambda PL promoter, the *E. coli* lac, trp and tac promoters, the SV40 early and late promoters and promoters of retroviral LTRs, to name a few. Other suitable promoters will be known to the skilled artisan. The expression constructs will further contain sites for transcription initiation, termination and, in the transcribed region, a ribosome binding site for translation. The coding portion of the target transcripts expressed by the constructs will preferably include a translation initiating at the beginning and a termination codon (UAA, UGA or UAG) appropriately positioned at the end of the polypeptide to be translated.

As indicated, the expression vectors will preferably include at least one selectable marker. Such markers include dihydrofolate reductase or neomycin resistance for eukaryotic cell culture and tetracycline, kanamycin or ampicillin resistance genes for culturing in *E. coli* and other bacteria. Representative examples of appropriate hosts include, but are not limited to, bacterial cells, such as *E. coli, Streptomyces* and *Salmonella typhimurium* cells; fungal cells, such as yeast cells; insect cells such as *Drosophila* S2 and *Spodoptera* Sf9 cells; animal cells such as CHO, COS and Bowes melanoma cells; and plant cells. Appropriate culture mediums and conditions for the above-described host cells are known in the art.

Among vectors preferred for use in bacteria expression of target proteins include pQE70, pQE60, pQE6, pQE7 and pQE-9, available from Qiagen; pBS vectors, Phagescript vectors, Bluescript vectors, pNH8A, pNH16a, pNH18A, pNH46A, available from Stratagene; and ptrc99a, pKK223-3, pKK233-3, pDR540, pRIT5 available from Pharmacia or the pHE vector series developed at HGS, Inc. Among preferred eukaryotic vectors are pWLNEO, pSV2CAT, pOG44, pXT1 and pSG available from Stratagene; and pSVK3, pBPV, pMSG and pSVL available from Pharmacia. Other suitable vectors will be readily apparent to the skilled artisan.

Among known bacterial promoters suitable for expression of target protein include the *E. coli* lacI and lacZ promoters, the T3 and T7 promoters, the gpt promoter, the lambda PR and PL promoters and the trp promoter. Suitable eukaryotic promoters include the CMV immediate early promoter, the HSV thymidine kinase promoter, the early and late SV40 promoters, the promoters of retroviral LTRs, such as those of the Rous sarcoma virus (RSV), and metallothionein promoters, such as the mouse metallothionein-I promoter.

Introduction of the expression construct into the host cell can be effected by calcium phosphate transfection, DEAE-dextran mediated transfection, cationic lipid-mediated transfection, electroporation, transduction, infection or other methods. Such methods are described in many standard laboratory manuals, such as Davis et al., *Basic Methods In Molecular Biology* (1986).

Transcription of the DNA encoding the target protein by higher eukaryotes may be increased by inserting an enhancer sequence into the vector. Enhancers are cis-acting elements of DNA, usually about from 10 to 300 bp that act to increase transcriptional activity of a promoter in a given host cell-type. Examples of enhancers include the SV40 enhancer, which is located on the late side of the replication origin at bp 100 to 270, the cytomegalovirus early promoter enhancer, the polyoma enhancer on the late side of the replication origin, and adenovirus enhancers.

For secretion of the translated target protein into the lumen of the endoplasmic reticulum, into the periplasmic space or into the extracellular environment, appropriate secretion signals may be incorporated into the expressed target protein. The signals may be endogenous to the target protein or they may be heterologous signals.

The target protein may be expressed in a modified form, such as a fusion protein, and may include not only secretion signals, but also additional heterologous functional regions. For instance, a region of additional amino acids, particularly charged amino acids, may be added to the N-terminus of the polypeptide to improve stability and persistence in the host cell, during purification, or during subsequent handling and storage. Also, peptide moieties may be added to the polypeptide to facilitate purification. Such regions may be removed prior to final preparation of the polypeptide. The addition of peptide moieties to polypeptides to engender secretion or excretion, to improve stability and to facilitate purification, among others, are familiar and routine techniques in the art. A preferred fusion protein comprises a heterologous region from immunoglobulin that is useful to solubilize proteins. For example, EP-A-O 464 533 (Canadian counterpart 2045869) discloses fusion proteins comprising various portions of constant region of immunoglobin molecules together with another human protein or part thereof. In many cases, the Fc part in a fusion protein is thoroughly advantageous for use in therapy and diagnosis and thus results, for example, in improved pharmacokinetic properties (EP-A 0232 262). On the other hand, for some uses it would be desirable to be able to delete the Fc part after the fusion protein has been expressed, detected and purified in the advantageous manner described. This is the case when Fc portion proves to be a hindrance to use in therapy and diagnosis, for example when the fusion protein is to be used as antigen for immunizations. In drug discovery, for example, human proteins, such as, hIL-5 has been fused with Fc portions for the purpose of high-throughput screening assays to identify antagonists of hIL-5. See, D. Bennett et al., *Journal of Molecular Recognition*, Vol. 8:52–58 (1995) and K. Johanson et al., *The Journal of Biological Chemistry*, Vol. 270, No. 16:9459–9471 (1995).

Process for Purifying Target Proteins

The bench scale method of the invention for protein production utilizes a series of solubilization procedures to separate the target proteins from the host contaminants by: cell lysis, 0.5M NaCl washes, to produce inclusion body containing partially purified target protein.

In the one embodiment of the invention, the partially purified inclusion bodies are subjected to further solubilization with 1.5 M of a guanidine salt extraction for 24 hours. Target protein is soluble and will stay in the soluble phase after 7,000×g centrifugation. Such sample is placed at 4° C. for further extraction overnight, centrifuged at 30,000×g. The supernatant, called a 1.5M guanidine salt extract, contains greater than 50% of the target proteins.

The 1.5M guanidine salt extracted target protein is refolded by quickly mixing the guanidine salt extract with 10–20 volumes of a buffer containing 50–100 mM sodium acetate pH 4.5, 150 mM sodium chloride, 2 mM EDTA with 30–60 minutes of vigorous stirring. The mixture is set at 2–10° C. without mixing for 1–48 hours prior to the chromatographic purification steps described below.

The refolded target protein samples are clarified through a 0.16 μm tangential filtration unit. The filtered sample was then captured through a strong cation exchange column. Suitable column materials are well known to those skilled in the art. Examples of such materials include POROS HS-50 column, Mono S, S Sepharose, SP Sepharose, Resource/ Source S, Toyopearl S, Toyopearl SP. The cation column is washed with a buffer containing 40 mM sodium acetate pH 4.5 to pH 6.0, 250 mM sodium chloride, eluted with steps of 500 mM, 1000 mM, 1500 mM sodium chloride. Target protein is eluted at the 500–1000 mM salt steps.

The cation column purified samples are diluted 4-fold, then applied onto a strong anion/weak cation tandem columns. Suitable column materials are well known to those skilled in the art. Examples of such columns include POROS HQ-50/POROS CM-20. Alternative materials for the strong anion column for the tandem column include Mono Q, Q Sepharose, Resource/Source Q, DEAE, Toyopearl Q. Alternative materials for the weak cation column for the tandem column include CM Sepharose, Toyopearl CM. The target protein will bind either to the anion or to the cation column depending upon the particular target protein. As will be understood by those skilled in the art, the arrangement of the column materials in the tandem column chromatography step can be reversed depending on which type of column material will bind target protein. In the tandem chromatography step, contaminants such as DNA, endotoxins and other proteins with lower pIs will bind to the strong anion column and the chemokines will pass through and bind to the weak cation column. For example, in the purification of proteins such as chemokines, the tandem columns are run with the chemokine sample passing over the strong anion column followed by the weak cation column.

The tandem columns are washed with 40 mM sodium acetate pH 4.75–6.0, 150–250 mM sodium chloride. The column having the bound target protein is eluted with a linear gradient of 250–1000 mM NaCl in 10–20 column volumes. The eluted fractions are analyzed through SDS-PAGE and the target protein containing peak fractions are combined.

Using the process described above, 50% purity can be achieved after the initial recovery and isolation of the inclusion bodies. The refolded target proteins are about 60–70% pure with a greater than 50% refolding efficiency. Indeed, the refolding efficiency for chemokines is about 60–80%. The subsequent chromatographic steps yield target proteins that were typically of greater than 95% purity. No major contaminant bands are visualized by commassie blue staining when 5 μg of such purified protein is analyzed on SDS-PAGE.

As the skilled artisan will recognize, additional purfication steps may be performed on the target protein using techniques that are well known to those skilled in the art. For example, additional chromotography steps such as size exclusion, ion exchange, hydrophobic interaction, affinity, reverse phase may be employed.

Although target proteins purified using the process of the present invention will generally be correctly folded, a certain population of the isolated target protein may not be in a completely proper conformation. Thus, it may be desirable, in these cases, to subject the target protein through a refolding process to restore that population to its native form by treating with reagent such as DTT, β-mercaptoethanol, glutathione, cysteamine or cysteine are present in the appropriate medium. In such cases, generally a concentration 100 μg/ml to 500 μg/ml of protein is treated with 5 mM–100 mM DTT for about 10–48 hrs at 2–25° C., preferably a concentration of 100 μg/ml to 300 μg/ml of protein is treated with 5 mM–100 mM DTT for about 48 hrs at 2–10° C. In addition, a concentration 100 μg/ml to 500 μg/ml of protein is treated with 10 mM–200 mM βME for about 10–48 hrs at 2–25° C. Alternatively, a concentration 100 μg/ml to 500 μg/ml of protein is treated with 10 mM–100 mM glutathione for about 10–48 hrs at 2–25° C. The target protein may, while in solution, be subjected to standard techniques directed to the purification of the protein such as gel filtration or ion exchange chromatography.

Industrial Scale Process for Purifying Target Proteins

Figure 30:
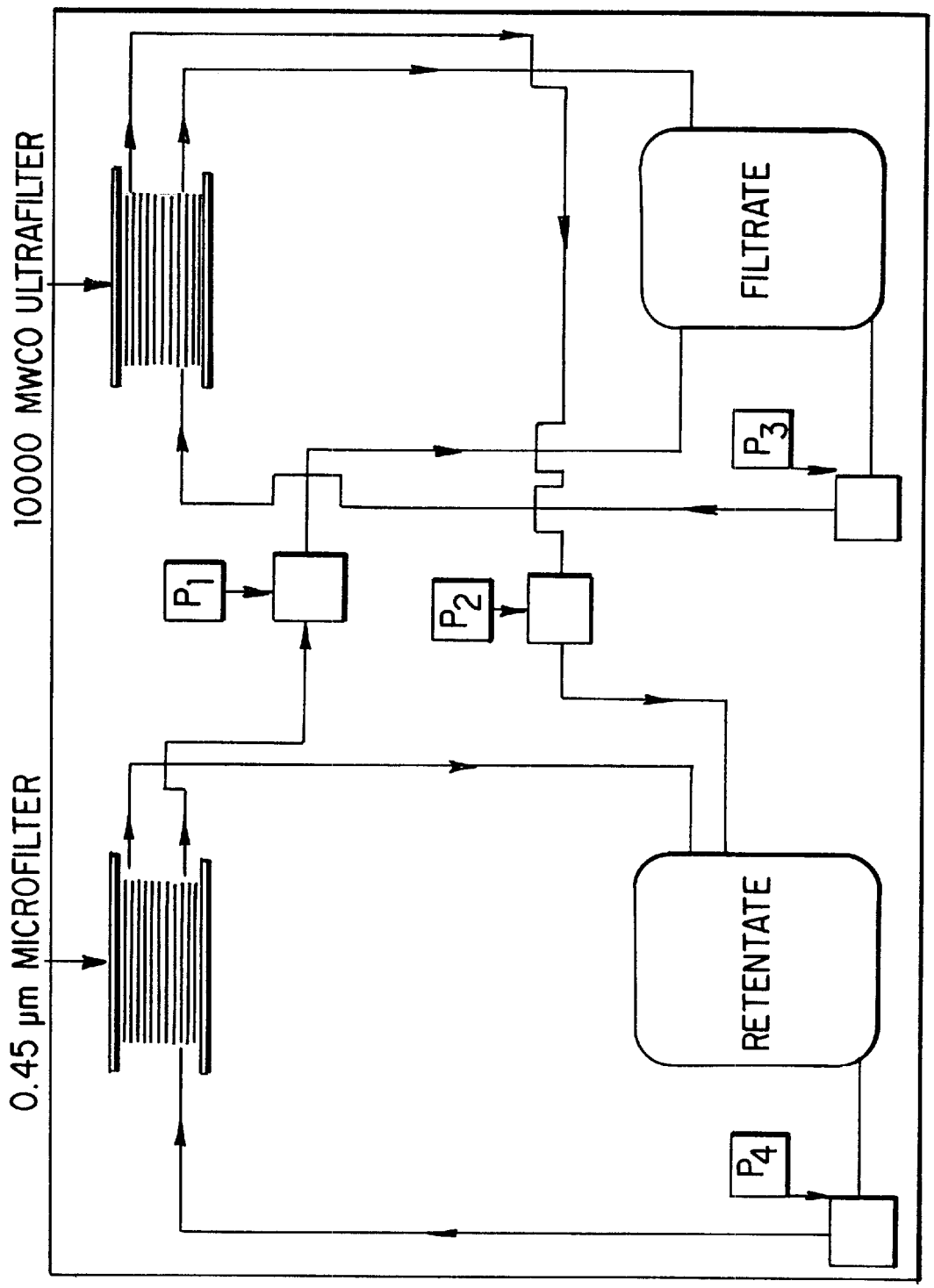
FIG. 30 shows the Microfiltration and Ultrafiltration Process Equipment-Product Flow Diagram.

The following provides an industrial scale manufacturing process for the present invention. It will be apparent to those skilled in the art that adjustments can be made to the process by routine optimization to accommodate the increased size of finished product desired. Within the stated process, there are steps that require centrifuation for the recovery of product. Although centrifugation Is used in industrial scale manufacturing, the product can alternatively be recovered using more economical and scaleable techniques such as Microfiltration and Ultrafiltration (Meagher et al, *Biotechnology and Bioengineering* 43:969–977 (1994)). This system has been employed for industrial scale recovery, clarification, concentration, and diafiltration for *E. coli*, mammalian and all insect cell expressed target proteins. (FIG. 30).

The principles of filtration were successfully applied within the stated process for inclusion body recovery, solubilization and refold with no effect on the homogeneity, identity, purity and activity of the target protein. For industrial scale manufacturing the following parameters of the process can be modified by the skilled artisan using routine optimization. The following process is applicable to all proteins using this invention.

Microfiltration is the use of a 0.45 μm tangential flow filter that retains large particles at approximately 0.45 μm or greater in diameter. This filter serves two purposes to wash inclusion bodies and to filter product through during Gu-HCl solubilization.

Ultrafiltration is the use of a 10,000 molecular weight cut off (MWCO) tangential flow filter that retains particles at approximately 10,000 kilodalton molecular weight or greater. The filter serves two purposes: to capture Gu-HCl solubilized target protein and to diafilter protein through retold.

(1) Bacterial cell paste is harvested by Microfiltration using a Pall-Filtron Nylon 0.45 μm tangential flow filter (such filters for industrial scale manufacturing can also be obtained from Millipore or AG Technology) and concentrated two fold. The *E. coli* cell particles are retained by the filter at this step.

(2) Suspension is then lysed (2 X in Microfluidizer (6,000–12000 psi) to release inclusion bodies.

(3) The lysed sample with inclusion bodies are washed by first diafiltering the sample with 4 diafiltration volumes of 100 mM Tris (pH 7.4); 25 mM EDTA and 0.5 M NaCl, followed by two diafiltration volumes of 100 mM Tris (pH 7.4); 25 mM EDTA. The inclusion bodies are retained by the filter at this step.

(4) Solubilization of target protein from inclusion bodies is achieved by adding solid Gu-HCl directly to the washed inclusion body suspension to a final concentration of about 1.5 M.

(5) The resulting supernatant contains target protein released from inclusion bodies and is recovered by recirculating the sample through the same Microfiltration device as in step 1.

(6) The product at this point passes through the 0.45 μm Microfiltration filter and is commonly referred to as filtrate. The product is then retained and concentrated using the 10,000 Kd MWCO Ultrafiltration device (such filters can be obtained from Pall-Filtron, Millipore or AG Technology Hollow fiber Filters). The Ultrafiltration filtrate is then passed back to the Microfiltration sample in order to maintain a constant Microfiltration volume. The recirculation process is maintained until >95% product has passed through the Microfiltration device and is captured by the Ultrafiltration device.

(7) The Ultrafiltration sample, containing about 80% target protein, is stored at 2–10° C. for 12–24 hours.

(8) The target proteins, such as chemokines, are refolded by removing the 1.5 M Gu-HCl using the same Ultrafiltration device as in step 6. The target proteins, such as chemokines are retained by the 10000 Kd MWCO filter and the Gu-HCl is removed by diafiltering the sample with 50–100 mM Sodium Acetate (pH4.5) 125 mM NaCl; 2 mM EDTA. Approximately 4–6 diafiltration volumes are sufficient to refold the protein.

(9) Liquid chromatographic purification is begun by either a 0.45 μm or 0.22 μm dead end filtration. However, a 0.16 μm tangential flow filtration can be used to filter out any precipitate present that would foul dead end filtration.

Figure 28:
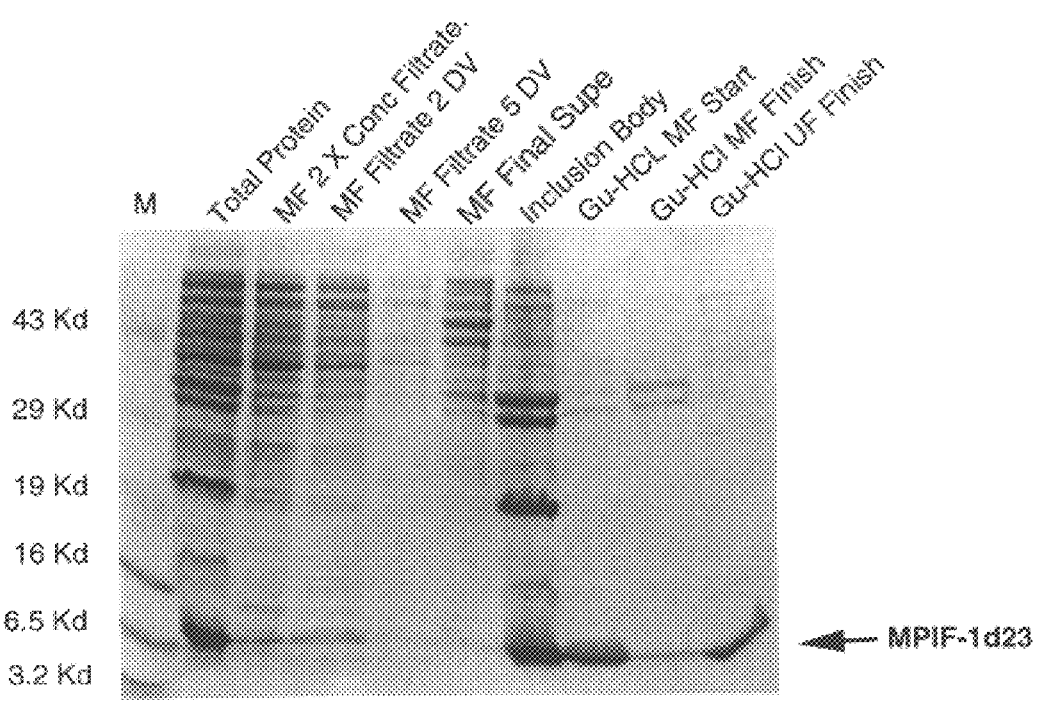
FIG. 28 shows SDS-Page analysis of Microfiltration-Ultrafiltration in process samples of MPIF-1d23 under reducing conditions. The gel was stained with coomassie blue. Lane 1 shows the molecular weight standards. Lane 2 Total, protein from IPTG induced MPIF-1d23 transformed E. coli post lysis. Lane 3 Microfiltration filtrate of a two times concentrate of total protein from IPTG induced Id23 transformed E. coli post lysis. Lane 4 Microfiltration filtrate after two diafiltration wash volumes. Lane 5 Microfiltration filtrate after five diafiltration wash volumes. Lane 6 Remaining contaminants present in sample supernatant after microfiltration wash. Lane 7 Inclusion body. Lane 8 Microfiltation starting sample supernatant of the 1.5 M Gu-HCl solubilized sample. Lane 9 Microfiltration retentate after filtration of the 1.5 M Gu-HCl solubilized sample. Lane 10 Ultrafiltration retentate of the 1.5 M Gu-HCl solubilized sample.
Figure 29:
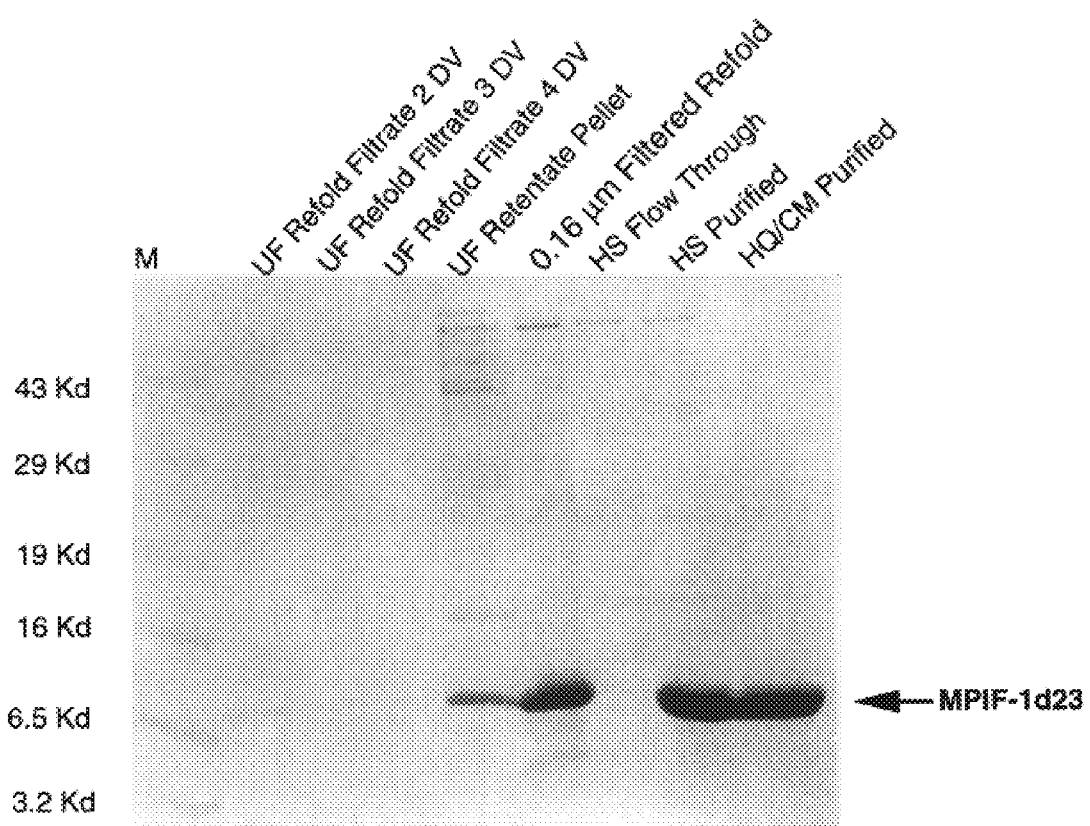
FIG. 29 shows SDS-PAGE analysis of Microfiltration-Ultrafiltration in process samples of MPIF-1d23 under reducing conditions. The gel was stained with coomassie blue. Lane 1 shows the molecular weight standards. Lane 2 Ultrafiltration filtrate after 2 diafiltration volumes with refold buffer. Lane 3 Ultrafiltration filtrate after 3 diafiltration volumes with refold buffer. Lane 4 Ultrafiltration filtrate after 4 diafiltration volumes with refold buffer. Lane 5 Ultrafiltration retentate pellet post diafiltration refold. Lane 6 0.16 μm filtered refold of the Ultrafiltration diafiltration refold sample. Lane 7 HS flow through. Lane 8 HS purified MPIF-1d23. Lane 9 HQ/CM purified MPEF-1d23.

At this point in the process liquid chromatography purification is peformed as stated above for the bench scale process of the invention. For industrial scale manufacturing column chromatography purification would be appropriately scaled to the size of the manufacturing batch desired. The results of the industrial scale process are shown in FIGS. 28 and 29. The skilled artisan familiar in the practices of large scale cGMP manufacturing would know how to adjust the parameters required to adapt this process for their particular use.

Chemokines

Chemokines are one class of proteins which are generally produced as inclusion bodies when expressed at a high level in bacteria. Chemokines, also referred to as intercrine cytokines, are a subfamily of structurally and functionally related cytokines. These molecules are 8–14 kd in size. In general, chemokines exhibit 20% to 75% homology at the amino acid level and are characterized by four conserved cysteine residues that form two disulfide bonds.

The intercrine cytokines exhibit a wide variety of functions as discussed above. In light of the diverse biological activities, it is not surprising that chemokines have been implicated in a number of physiological and disease conditions, including lymphocyte trafficking, wound healing, hematopoietic regulation and immunological disorders such as allergy, asthma and arthritis.

For example, the chemokines MPIF-1, MPIF-1d23, MIP-1α, M-CIF, MIP-4, Ck-β-13, and Ck-α-4 purified according to the method of the present invention can be used for therapeutic purposes, such as, to protect bone marrow stem cells from chemotherapeutic agents during chemotherapy, to remove leukemic cells, to stimulate an immune response, to regulate hematopoiesis and lymphocyte trafficking, treatment of psoriasis, solid tumors, to enhance host defenses against resistant and acute and chronic infection, and to stimulate wound healing. In addition, disorders that could be treated with chemokines MPIF-1, MPIF-1d23, MIP-1α, M-CIF, MIP-4, Ck-β-13, and Ck-α-4 include tumors, cancers, and any disregulation of immune cell function including, but not limited to, autoimmunity, arthritis, leukemias, lymphomas, immunosuppression, sepsis, wound healing, acute and chronic infection, cell mediated immunity, humoral immunity, inflammatory bowel disease, myelosuppression, and the like.

A preferred embodiment of the present invention is outlined below and comprises the following: cell lysis and inclusion body suspension are provided by steps (1)–(3); inclusion body solubilization is provided by steps (4)–(6);

chemokine refolding is provided by steps (7)–(8); and chemokine purification is provided by steps (9)–(14).

(1) Bacterial cell paste is resuspended in buffer (100 mM TRIS (pH 7.4); 50 mM EDTA);

(2) Suspension is lysed (2 X in Microfluidizer (4,000–12,000 psi)) to release inclusion bodies;

(3) Lysed sample with inclusion bodies is mixed with a NaCl solution to bring the final concentration of NaCl to 0.5 M and then centrifuged (7,000× g) 15 min;

(4) The pellet (containing chemokine target protein inclusion bodies) is washed again with the same buffer as in step (3). The pellet (i.e., inclusion bodies) is solubilized with using 1.5 M GuHCl (2–4 hours);

(5) The GuHCl solubilized sample is centrifuged (7,000× g) and the resulting supernatant contains chemokine protein released from inclusion bodies by step (4). A second extraction of the 7,000× g pellet can be optionally performed with a higher concentration GuHCl if desired;

(6) Supernatant is stored at 4° C. for two hours and the supernatant is optionally recentrifuged at up to 30,000 × g (80% chemokine);

(7) Chemokine is refolded by mixing the GuHCl extracted supernatant with 10–20 volumes of buffer (50–100 mM sodium acetate (pH 4.5), 150 mM NaCl; 2 mM EDTA);

(8) Refolded protein is stored at 4° C. for 1–48 hours before chromatographic purification;

(9) Liquid chromatographic purification is begun by 0.16 $\mu$m tangential filtration. The chemokine is captured by chromatography using a strong cation column;

(10) Column is washed in buffer (40 mM Na acetate (pH 6.0), 250 mM NaCl);

(11) Elution is carried out using a step wise gradient consisting of 500, 1000, & 1500 mM NaCl (biologically active chemokines are found in the 500 and 1000 mM NaCl steps);

(12) Chemokine fractions are diluted 2–4 times in buffer (appropriate for both anion and cation chromatography) followed by tandem chromatography using strong anion and weak cation exchange chromatography;

(13) The weak cation column is washed in buffer (40 mM Na acetate (pH 6.0), 150–250 mM NaCl); and

(14) Chemokine is eluted from the weak cation column with a 10–20 column volume linear gradient of 250–1000 mM NaCl ; and

(15) The peak fractions are further polished through a size exclusion column (sephacryl S-100) equilibrated with 50 mM NaOAc at pH 6, 150–300 mM NaCl.

The eluted fractions obtained from step (15) are analyzed using SDS-PAGE and the chemokine containing peak fractions are combined.

Figure 9:
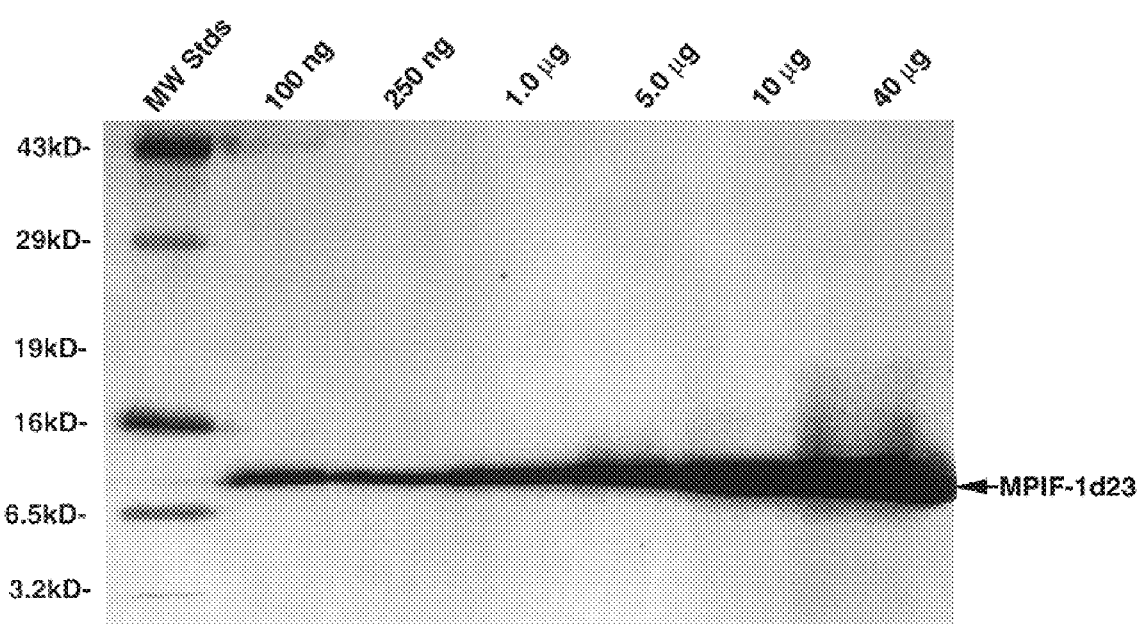
FIG. 9. Silver stained SDS-PAGE analysis of purified MPIF-1d23 under reducing conditions. The gel was loaded with the indicated amounts of purified MPIF-1d23 and was silver stained. Lane 1 shows the molecular weight standards.

Using the process described above, 50% purity can be achieved after the initial recovery and isolation of the inclusion bodies. The refolded chemokines are about 60–70% pure with a greater than 60% refolding efficiency. The subsequent chromatographic steps yield chemokine proteins (e.g., MPIF-1) that are typically of greater than 95% purity. As noted in Example 1, no major contaminant bands were visualized by silver staining when 40 $\mu$g of MPIF-1 purified by this method was analyzed by SDS-PAGE. (FIG. 9)

As noted above, the skilled artisan will recognize that additional purification steps may be performed on the isolated chemokine using techniques that are well known to those skilled in the art.

The method of the present invention provides a very unique process for purifying proteins from inclusion bodies. The process itself is very simple, scalable and reproducible for all seven chemokines tested (i.e, MPIF-1, MPIF-1d23, MIP-1$\alpha$, M-CIF, MIP-4, Ck-$\beta$-13, Ck-$\alpha$-4).

The invented process greatly improves the yield of the exemplified recombinant chemokines from cell (e.g., bacterial) lysates. Further, the resulting protein is highly homogenous and biologically active.

The process of the present invention has been shown to be very effective in removal of endotoxin. Endotoxin removal is a very important part of protein purification, especially for proteins produced in $E. coli$ that will be used therapeutically. The method of the present invention can separate the target protein away from greater than 90% of endotoxin contamination at the very first step. The final purified protein contains 100 million-fold less endotoxin (i.e., 0.01–1 EU/mg).

This method can be applied to the production of other chemokines which form inclusion bodies when expressed in host cells and has resulted in an increase of production scale from several milligrams to grams for MPIF-1, MPIF-1d23, MIP-1$\alpha$, M-CIF, MIP-4, Ck-$\beta$-13, and Ck-$\alpha$-4. As a result, large quantities of such products can be cGMP manufactured for FDA IND submission and Phase I Clinical Trials using the methods of the present invention.

Process for the Purification of Secreted Target Proteins

Another aspect of the invention provides for the purification of target proteins that have been expressed in a secreted form from insect cells and mammalian cells. Since the secreted target proteins expressed in these systems are not in the form of inclusion bodies, the protein would not require solubilization. The process of the invention for the purification of secreted proteins is as follows.

The target protein samples are clarified through a 0.16 $\mu$m tangential filtration unit. The filtered sample is then captured through a strong cation exchange column. Suitable column materials are well known to those skilled in the art. Examples of such strong anion exchange column materials include POROS HS-50 column, S Sepharose, SP Sepharose, Reseource/Source S, Toyopearl S. The cation column is washed with a buffer containing 40 mM sodium acetate pH 4.5 to pH 6.0, 250 mM sodium chloride, eluted with steps of 500 mM, 1000 mM, 1500 mM sodium chloride. Target protein is eluted at the 500–1000 mM salt steps.

The cation column purified samples are diluted 4-fold, then applied onto a strong anion/weak cation tandem columns. Suitable such column materials are well known to those skilled in the art. Examples of such columns include POROS HQ-50/POROS CM-20. Alternative materials for the strong anion column for the tandem column include Mono Q, Q Sepharose, Resource/Source Q, DEAE, Toyopearl Q. Alternative materials for the weak cation column for the tandem column include CM Sepharose, Toyopearl CM. The target protein will bind to either the anion or to the cation column depending upon the particular protein. As will be understood by those skilled in the art, the arrangement of the column materials in the tandem column chromatography step can be reversed depending on which type of column material will bind target protein. The tandem columns are washed with 40 mM sodium acetate pH 4.75–6.0, 150–250 mM sodium chloride. The column having the bound target protein is eluted with a linear gradient of 250–1000 mM NaCl in 10–20 column volumes. The eluted fractions are analyzed through SDS-PAGE and the target protein containing peak fractions are combined.

As the skilled artisan will recognize, additional purfication steps may be performed on isolated target protein using techniques that are well known to those skilled in the art. For example, additional chromatography steps such as size exclusion, ion exchange, hydrophobic interaction, affinity, reverse phase may be employed.

Having generally described the invention, the same will be more readily understood by reference to the following examples, which are provided by way of illustration and are not intended as limiting.

EXAMPLES

Example 1: Purification of MPIF-1d23 from E. coli

A bacterial expression construct with the chemokine gene without the secreted signal peptide was made and used to transform E. coli host cells. IPTG induction of the lac Z promoter is used to express the chemokine. Other induction modes can also be used.

Recent studies have shown that some N-terminus truncated MPIF-1 variants have higher biological efficacy compared to the full length protein. Many forms of MPIF-1 variants were constructed and subsequently expressed in E. coli. and purified.

MPIF-1d23 is a variant in 23 residues are deleted from the N-terminus of MPIF- 1. MPIF-1d23 is produced in E. coli with IPTG induction and is present in the insoluble fraction (so called inclusion body) after cell lysis.

Methods

Expression of MPIF-1d23

The MPIF-1d23 gene was inserted into the expression vector pQE7 by using recombinant DNA techniques well known to those skilled in the art. The coding sequence of the MPIF-1 d23 was amplified by PCR during which unique restriction sites, SphI/HindIII, were introduced thereby allowing the gene to be cloned into the E. coli expression vector pQE7. The resulted plasmid DNA was used to transform E. coli M15 Rep4 host cell. For small scale fermentation, bacterial transformant was grown in LB medium containing Ampicillin and Kanamycin, then induced for production of chemokine with 1 mM IPTG for 3 hours. For large scale production, a semi defined medium or defined medium without antibiotics was used.

Solubilization of MPIF-1d23 from E. coli

MPIF-1d23 was produced as insoluble protein deposited as inclusion bodies. The method of MPIF-1d23 production utilizes a series of solubilization procedures to separate the target protein from the host contaminants by: cell lysis, 0.5M NaCl washes, to isolate inclusion body that containing partially purified MPIF-1d23. In details, E. coli cell paste was resuspended in a buffer containing 100 mM Tris pH 7.4, 25 mM EDTA, passed through a Microfluidizer twice at 6000–8000 psi. The lysed sample was mixed with NaCl to a final concentration of 0.5M, then spun at 7000×g for 15 minutes. The resulting pellet was washed with the same buffer plus 0.5M NaCl again as partially purified inclusion body.

The partially purified inclusion body was subjected to further solubilization with 1.5–1.75 M guanidine hydrochloride for 2–4 hours at 4–25° C. MPIF-1d23 was soluble and remained in the soluble phase after 7,000×g centrifugation. This sample was placed at 4° C. for further solubilization overnight, then centrifuged at 30,000×g. The supernatant is called a 1.75M GuHCl extract of which 50–70% is MPIF-1d23 protein.

Refolding

The 1.75M GuHCl extracted chemokine was refolded by quickly mixing the GuHCl extract with 10 volumes of a refold buffer containing 50 mM sodium acetate pH 4.5, 125 mM sodium chloride, 2 mM EDTA with 30 minutes of vigorously stirring. The mixture was set at 4° C. without mixing for 0.5–48 hours prior to the chromatographic purification steps described below.

Liquid Chromatogjaphic Purification of MPIF-1

The refolded MPIF-1d23 samples were clarified through a 0.16 $\mu$m tangential filtration unit. The filtered sample was captured through a strong cation exchange (poros HS-50) column. The HS-50 column was washed with a buffer containing 50 mM sodium acetate pH 6.0, 300 mM sodium chloride, eluted with steps of 500 mM, 750 mM, 1000 mM, 1500 mM sodium chloride.

The HS-50 0.5 M sodium chloride eluted fraction was diluted 2-fold, then applied onto a set of anion (poros HQ-50) and cation (poros CM-20) exchange columns in a tandem mode. Both columns were washed with 50 mM sodium acetate pH 6.0, 150 mM sodium chloride. The CM column was eluted with a linear gradient of 150–750 mM NaCl in 10–20 column volumes. Elute fractions were analyzed through SDS-PAGE and RP-HPLC. The MPIF-1d23 containing peak fractions which has the expected RP-HPLC profile were combined. The HQ/CM purified MPIF-1d23 was further polished by a size exclusion (Sephacryl S-100) chromatographic step.

Purification of MPIF-1 and MPIF-1d23

A production process of MPIF-1 described in the method section above was used to purified MPIF-1d23. A 50–70% purity can be achieved after the initial recovery and isolation of inclusion body. From the 1.75 M GuHCl extract, the refolding efficacy of MPIF-1d23 is greater than 80%.

Refolded sample was subsequently purified through three chromatographic steps. After the HS-50 and HQ/CM steps, MPIF-1d23 sample is typically 98% pure. The recovery of the chromatographic procedures is greater than 50%. Only two minor bands (approximately 50 ng each) are seen by silver staining when 40 $\mu$g of such purified protein is loaded. Size exclusion chromatography as the last step was very effective in removing these two minor contaminants. This step also will be useful as a buffer exchange step for final bulk formulation of the protein. The final purified MPIF-1d23 is free of any visible contaminating bands by silver staining when 40 $\mu$g of protein is loaded. (FIG. 9).

Table I is an outline example of the purification results. FIG. 1 shows the SDS-PAGE of the purified protein. Typically, the yield of MPIF-1 is 1 gram per kilogram E coli cell paste.

TABLE 1

Purification Table of MPIF-1d23

| Step | Volume (ml) | Protein Conc. (mg/ml) | Total Protein (mg) | Estimated Purity (%) | Purified MPIF-1d23 (mg) | Total Recovery (%) |
|---|---|---|---|---|---|---|
| E. coli Culture | (24000) | | (1.2 Kg. Wt.) | | | |
| GuHCl Extract | 6000 | 5 | 3000 | 60% | 1800 | 100 |
| 0.16 $\mu$m filtration | 50000 | 0.05 | 2500 | 70% | 1750 | 97 |

TABLE 1-continued

Purification Table of MPIF-1d23

| Step | Volume (ml) | Protein Conc. (mg/ml) | Total Protein (mg) | Estimated Purity (%) | Purified MPIF-1d23 (mg) | Total Recovery (%) |
|---|---|---|---|---|---|---|
| HS pool | 650 | 2.5 | 1625 | 90% | 1462 | 81 |
| HQ/CM pool | 140 | 8.2 | 1148 | 98% | 1125 | 63 |
| S-100 pool | 275 | 4.0 | 1100 | 99% | 1089 | 61 |

Analysis of Purified MPIF-1

1. Size exclusion chromatography

A monomeric MPIF-1d23 is 8.9 kD, and a dimer will be 17.8 kD. Purified MPIF-1d23 runs as a single symmetrical peak just behind the 17 kD (myoglobin) molecular marker. Because of the limited resolution of the sizing column at this molecular weight range, it cannot be precisely determined if the protein is a monomer. However, mass spec data and primary NMR analysis indicate that purified MPIF-1d23 is monomeric.

2. Reverse phase HPLC

Active MPIF-1d23 purified from E. coli as described above has a retention time of 6.15 (±0.1) minutes with a shoulder at 6.8 (±0.1) minutes in a C8 RP-HPLC analysis while other isoforms have longer retention time such as 6.7 to 7.1 minutes. The active MPIF-1d23 reversed phase HPLC profile is very similar to those of the MPIF-1 purified from baculovirus infected Sf-9 supernatant and CHO cell supernatant.

It has not yet been fully determined what component corresponds to the shoulder peak. Since this main peak plus shoulder profile is also seen in baculovirus (HG00300-B5, HG00300-B7) and CHO (HG00311-C1) expressed MPIF-1 which does not involve a refolding process, thus, the shoulder peak is not likely generated from incomplete refolding. Mass spec analysis show that the main peak and shoulder have the exact same molecular weight as expected from the amino acid sequence of MPIF-1d23.

3. Endotoxin level

Purified MPIF-1 from the above process contains low level of endotoxin, typically below 0.1 EU/mg purified protein.

4. IEF

Final purified MPIF-1 run as a single band on an isoelectric focusing gel. This is indicative of homogeneity of the protein.

Characterization of MPIF-1d23 Isoforms

We have observed the presence of different isoforms of MPIF-1d23 from E. coli cell paste. With the purification methods described above, many different active isoforms MPIF-1d23 were isolated When MPIF-1d23 inclusion body pellet was extracted with 1.75 M GuHC1 for 2–4 hours, normally 50% of MPIF-1d23 is in the soluble phase. The other 50% of MPIF-1d23 which is not solubilized under such conditions can be extracted out by higher concentration of GuHC1, then refolded, purified and tested for HPLC profiles and bioactivities. It was found that such populations of MPIF-1d23 have different CM and RP-HPLC profiles, and they are less active or inactive in our in vitro bioassays. Therefore, there are different isoforms of MPIF-1d23 present in the inclusion body. By solubilizing inclusion body with low concentration GuHC1, the primarily active portion of MPIF-1d23 can be selectively extracted out from a heterogeneous MPIF-1d23 population.

The 1.75M GuHC1 extract was refolded through dilution. Greater than 80% of MPIF-1d23 remains in solution and refolded protein is 60–70% pure as analyzed by SDS-PAGE. Such sample was captured in a HS column and eluted using NaCl steps into 0.5 M, 0.75M, 1.0M and 1.5 M sodium chloride fractions. Each of the fractions contains MPIF-1d23 protein and shows same protein band on SDS-PAGE. Our analysis on each fractions shows that the 0.5 M sodium chloride fraction contains the most active MPIF-1d23 while other fractions eluted with higher concentration of sodium chloride have different CM and RP-HPLC profiles than the 0.5M fraction and subsequently are less or not active in the bioassay. Therefore, the HS step elution further separate the active MPIF-1d23 from other less active isoforms.

The HS purified MPIF-1d23 was subsequently applied onto a set of HQ-50 and CM-20 columns in a tandem mode. MPIF-1d23 was eluted from CM column with a linear gradient as a main peak at approximately 400 mM sodium chloride in 50 mM sodium acetate pH 6.0. Several small peaks are often present after the main peak and they were identified as the less active isoforms by RP-HPLC and bioassays (see Table 2).

TABLE 2

Comparison of Different CM Peak of MPIF-1d23

| MPIF-1d23 Sample | Sample Elution (mM NaCl) | RP-HPLC Retention Time (min) | Ca++ Mobilization (ng/ml)* | LPP-CFC Inhibition (ng/ml)# |
|---|---|---|---|---|
| CM Peak 1 | 400 mM | 6.1 | 100 | 1 |
| CM Peak 2 | 450 mM | 6.1, 6.71 | 100 | 100 |
| CM Peak 3 | 500 mM | 6.8 | 1000 | >1000 |

*Minimum concentration required to mobilize calcium in THP-I cells
Concentration producing 50% inhibition of LPP-CFC colony formation compared to the control The three CM peaks have identical sizing HPLC profiles. Mass Spec analysis shows that the CM peak 1 and peak 3 samples have the exact same molecular mass as expected for a monomeric MPIF-1d23 based on its amino acid sequence. Since MPIF-1d23 has 6 cysteins, there could be many different disulfide bond related conformations. To demonstrate this possibility, the two MPIF-1d23 fractions were treated with 6M GuHC1 with or without 50 mM DTT at room temperature overnight, then refolded and purified using the same methods described above. Samples treated with 6 M GuHC1 without DTT retain their original RP-HPLC profiles. However, peak 3 sample treated with 6 M GuHC1 plus 50 mM DTT presented a shift of RP-HPLC profiles which contains 50% of the 6.1 minute peak. There is a possibility that these two isoforms have different disulfide linkages. With treatment of GuHC1 plus DTT, a less active isoform was converted to active MPIF-1d23 through rearrangement of the disulfide linkage.

Discussion

The foregoing demonstrates that the purification method of the present invention results in the successful recovery and purification of *E. coli* derived chemokines. The advantages of using this method are that it is simple, it can be done at relatively low cost and, thus, can be easily scaled up and adapted for cGMP manufacturing. It yields a biologically active, highly homogeneous product with no aggregated forms of the target protein, and good recovery of chemokine is achieved with high purity and extremely low endotoxin level.

This method can be applied to the production of other chemokines from *E. coli* and has resulted in an increase of protein production scale for MPIF-1, MPIF-1d23, MIPα1, M-CIF and MIP-4, among others, from several milligrams to gram quantities. As a result, large quantities of target proteins can be cGMP manufactured to achieve goals for IND submissions and Phase I Clinical Trials.

Example 2: GuHCl Titration

Since the GuHC1 concentration for inclusion body solubilization might play a role in the initial output of the active and inactive MPIF-1d23, a GuHC1 titration experiment was performed to optimize the GuHC1 extraction step and systematically evaluate the process. MPIF-1d23 inclusion body was prepared as described, then solubilized with 0.75M, 1.5M, 2.0M, 3.0M, 4.0M, and 6.0M GuHC1 for three hours.

Figure 10:
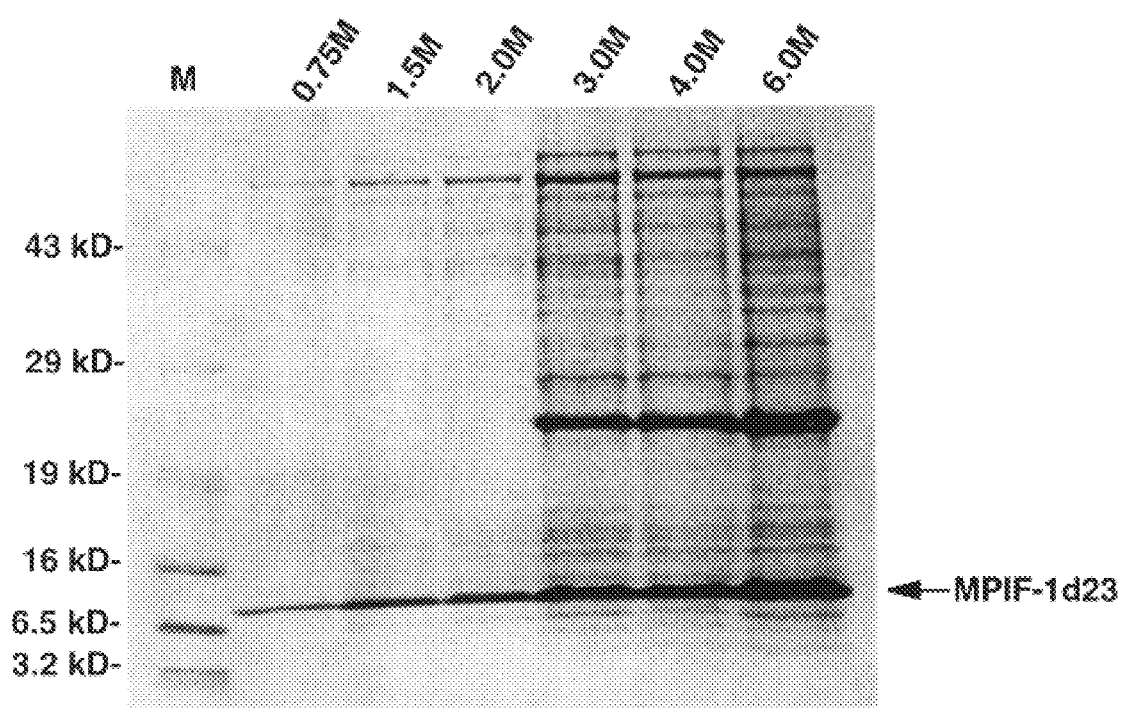
FIG. 10: MPIF-1d23 inclusion body was prepared and solubilized as described on page 23 steps (1)–(6) with the indicated concentrations of GuHC1 for 3 hours, separately. 20 µl of the GuHC1 extracts were precipitated with Trichloride Acid (TCA) and analyzed by SDS-PAGE under reducing conditions. The gel was stained with coomassie blue.
Figure 11:
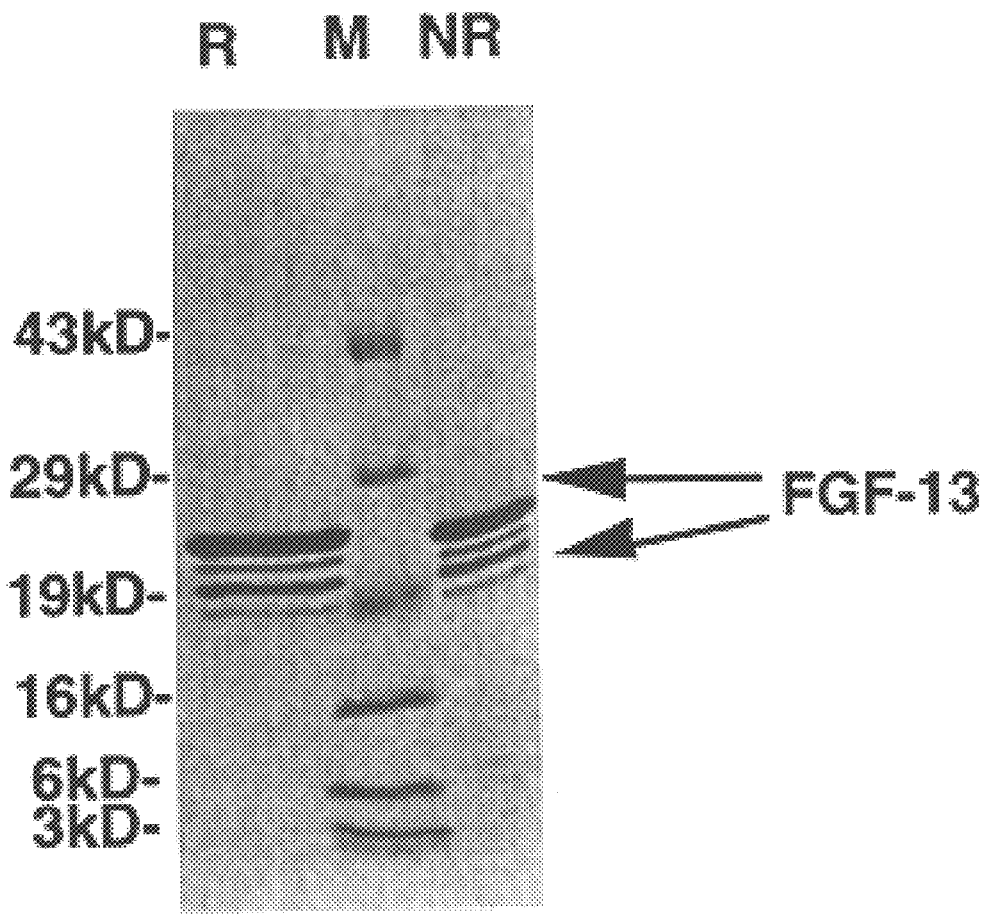
FIG. 11: SDS-PAGE analysis of 5 µg purified FGF-13. The gel was stained with Coomassie blue. Lane 1: 5 µg FGF-13 under reducing conditions. Lane 2: Molecular weight standards. Lane 3: 5 µg FGF-13 under non-reducing conditions.
Figure 12:
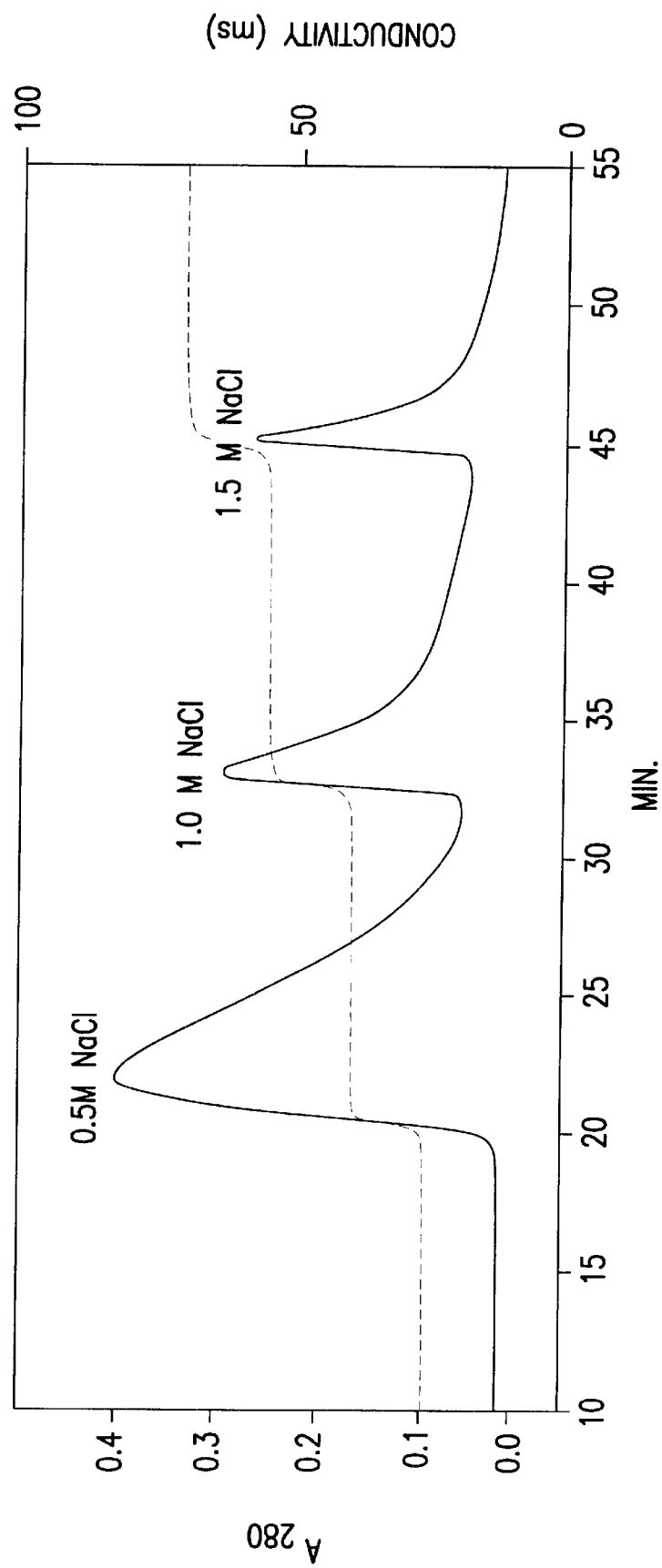
FIG. 12. Purification of MPIF-1d23 through strong Cation Exchange HPLC in a BioCad 250 HPLC workstation (PerSeptive Biosystem). The refolded MPIF-1d23 sample was filtered through a 0. 16 µm tangential filtration unit, then applied to a POROS HS-50 column. The HS colunm was washed with a buffer containing 50 mM sodium acetate, 300 mM sodium chloride, then eluted with 500 mM, 1000 mM, 1500 mM sodium chloride steps in 50 mM sodium acetate pH 6.0. The absorbance of 280 nm and conductivity were continuously monitored. Active MPIF-1d23 was mainly present in the 0.5 M sodium chloride fractions.
Figure 13:
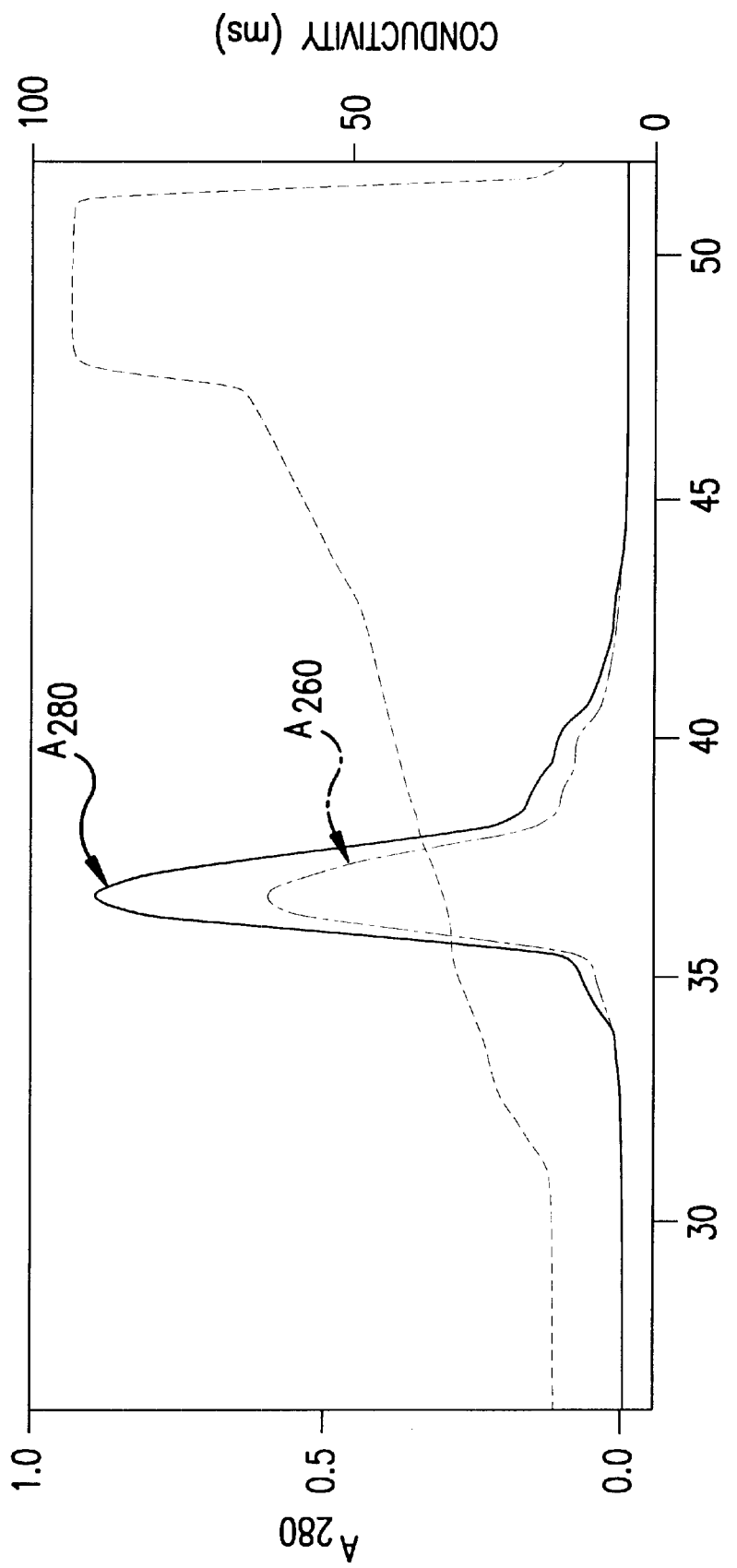
FIG. 13. Purification of MPIF-1d23 through Anion/Cation Exchange tandem HPLC in a BioCad 60 HPLC workstation (PerSeptiveBiosystem). The HS purifiedMPIF-1d23 sample was diluted 2-fold, then applied to a set of POROS HQ-50/CM-20 colunms in a tandem mode. Both columns were washed with a buffer containing 50 mM sodium acetate, 250 mM sodium chloride. The CM column was eluted with a 10–20 column volume linear gradient of 250–1000 mM sodium chloride in 50mM sodium acetate pH 6.0. The absorbance of 280 nm, 260 nm and conductivity were continuously monitored. Active MPIF-1d23 was present in the main peak.

The initial extraction shows that 0.75M GuHC1 was able to extract out some MPIF-1d23, 1.5–2.0M GuHC1 has better extraction, 3.0M to 6.0M GuHC1, considerable amount of other contaminants are present in the extract (see FIG. 10). After refolding through dilution to final concentration of 150 mM GuHC1, samples were captured in a HS column and eluted with steps of 0.3 M, 0.5M, 0.75M, 1.0 M and 1.5M NaCl. Previous experiments showed that active MPIF-1d23 was eluted in the 0.5M NaCl step. 0.5M NaCl pooled MPIF-1d23 was further purified through HQ/CM tandem columns and the first peak which was identified as the active MPIF-1d23 peak from CM column was pooled as the final purified sample.

The purified samples were analyzed by SDS-PAGE, RP-HPLC, total yield, and calcium mobilization activity (Table 3). Table 3 shows that 1.5M to 2.0M GuHC1 extraction produced the best recovery and best purity for active MPIF-1d23. However, 0.75M GuHC1 is not enough to dissociate MPIF-1d23 from the inclusion body. While high concentration of GuHC1 seems to extract out more MPIF-1d23 initially as well as other contaminants from inclusion body as shown on SDS-PAGE (FIG. 10), this MPIF-1d23 band includes the non-active MPIF-1d23 isoform. The presence of these contaminants might significantly interfere with the refolding. The final result is less active protein and lower purity from higher concentration of GuHC1 extraction. Therefore, the range of about 1.5M to about 1.75M GuHC1 appears to be optimal.

TABLE 3

Summary of GuHCl Titration Experiments

| Sample | Total Recovery (mg) | Purity by SDS-PAGE (%) | RP-HPLC# Active Peak (%) | Ca++ Mobilization* (nM) |
|---|---|---|---|---|
| 0.75M. GuHCl | 0.33 mg | 80% | 38% | 124,224 |
| 1.5M GuHCl | 17.82 mg | 98% | 80% | 159,253 |
| 2.0M GuHCl | 25.74 mg | 98% | 75% | 126,262 |

TABLE 3-continued

Summary of GuHCl Titration Experiments

| Sample | Total Recovery (mg) | Purity by SDS-PAGE (%) | RP-HPLC# Active Peak (%) | Ca++ Mobilization* (nM) |
|---|---|---|---|---|
| 3.0M GuHCl | 11.76 mg | 95% | 73% | 141.268 |
| 4.0M GuHCl | 4.29 mg | 92% | 65% | 113.245 |
| 6.0M GuHCl | 3.3 mg | 90% | 37% | 109.208 |

*Change in intracellular calcium at 100 and 1000 ng/ml of MPIF-1d23, respectively
Percentage of the 6.1 minutes peak integrated area to the overall peak area.

Example 3: Refolding Time for MPIF-1d23

To optimize the refolding process, a refold time course was performed. The 1.75 GuHCl extract of MPIF-1d23 was prepared as described in the method above, then diluted 10-fold in the refolding buffer (50 mM sodium acetate pH 4.5, 125 mM sodium chloride, 2 mM EDTA). Refolded samples were taken after one, three, six and twenty hours. Each time course sample was processed through the HS and HQ/CM chromatographic steps.

The purified samples were analyzed by SDS-PAGE, RP-HPLC, total yield, and calcium mobilization activity. Table 4 shows that sample taken just one hour after dilution is just as active and pure as the one taken after 20 hours refold. Therefore, there is no need for lengthy refolding in our process. Perhaps, a portion of MPIF-1d23 presence in the inclusion body population is already in a corrected folded conformation. This portion of protein can be easily dissociated from inclusion body by low concentration of GuHCl which does not cause major denaturation, therefore, no major refolding process is needed.

TABLE 4

Summary of Refolding Time Course Experiments

| Sample | Total Recovery (mg) | Purity by SDS-PAGE (%) | RP-HPLC# Active Peak % | Ca++ Mobilization* (nM) |
|---|---|---|---|---|
| Refold TC 1 hour | 4.8 | 98% | 80% | 160, 259 |
| Refold TC 3 hours | 4.5 | 98% | 80% | 119, 257 |
| Refold TC 6 hours | 4.4 | 98% | 80% | 136, 273 |
| Refold TC 20 hours | 5.1 | 98% | 80% | 149, 250 |

*Change in intracellular calcium at 100 and 1000 ng/ml of MPIF-1d23, respectively.
Percentage of the 6.1 minutes peak integrated area to the overall peak area.

Example 4: Endotoxin Removal

Endotoxin removal is an important step of protein purification, especially in the case of *E. coli* derived product. During chemokine purification process, the level of endotoxin at different steps was monitored and found that over 90% of endotoxin can be removed through the step of inclusion body isolation (see Table 5). The final purified MPIF-1d23 contains known extremely low level of endotoxin.

TABLE 5

Endotoxin Removal During the Chemokine Purification Process

| Sample | EU/ml | Vol (ml) | Total EU | % |
|---|---|---|---|---|
| E. coli cell paste | $5 \times 10^5$ | 2000 | $1.0 \times 10^9$ | 100 |
| Cell lystate supern | $6 \times 10^5$ | 2000 | $1.2 \times 10^9$ | 120 |
| Cell lystate pellet | $4.4 \times 10^4$ | 2000 | $8.8 \times 10^7$ | 5.4 |
| Refold | 0.26 | 5500 | $1.5 \times 10^3$ | 0.00015 |
| HS pool | 2.4 | 550 | $1.3 \times 10^3$ | 0.00013 |
| HQ/CM pool 1 | 0.6 | 60 | 36 | 0.0000036 |
| HQ/CM pool 2 | 0.09 | 60 | 5.4 | 0.00000054 |

Example 5: Purification of M-CIF from E. coli

The M-CIF gene was inserted into the expression vector pQE6 using recombinant DNA techniques well known to those of skill in the art. Briefly, the coding sequence of M-CIF was amplified by PCR during which unique restriction sites (BsphI and BamHI) were introduced thereby allowing the gene to be cloned into the E. coli expression vector pQE60. The resulting plasmid DNA was used to transform E. coli M15 Rep4 host cells. Cell cultures were prepared as described in Example 1.

The purification involves the following steps, and unless otherwise specified, all procedures were conducted at 4–10° C.

M-CIF was produced as insoluble protein deposited in inclusion bodies. Upon completion of the production phase of the E. coli fermentation, the cell culture was cooled to 4–10° C. and the cells were harvested by continuous centrifugation at 15,000 rpm (Heraeus Sepatech). On the basis of the expected yield of protein per unit weight of cell paste and the amount of purified protein required, an appropriate amount of cell paste, by weight, was suspended in a buffer solution containing 100 mM Tris, 50 mM EDTA, pH 7.4 in a 10–20 ml buffer per gram cell paste ratio. The cells were dispersed to a homogeneous solution using a high shear mixer.

The cells were then lysed by passing the solution through microfluidizer (Microfluidics, Corp. or APV Gaulin, Inc.) twice at 4000–12000 psi. The homogenate was mixed with a NaCl solution to a final concentration of 0.5 M NaCl, followed by centrifugation at 7,000×g for 15 min. The resulting pellet was washed again using 0.5 M NaCl, 100 mM Tris, 50 mM EDTA, pH 7.4, followed by centrifugation at 7000×g for 15 min.

The washed inclusion bodies (pellet) were solubilized with 1.5 M guanidine hydrochloride (GuHCl) for 2–4 hours. After centrifugation at 7,000×g for 15 min., the pellet was discarded and the M-CIF-containing supernatant was placed at 2–10° C. overnight.

Following high speed centrifugation (30,000×g) to remove the insoluble particles, the GuHCl solubilized proteins were refolded by vigorous stirring the GuHC1 extract with 20 volumes of buffer containing 50 mM sodium, pH 4.5, 150 mM NaCl, 2 mM EDTA. The refolded diluted protein solution was kept at 2–10° C. without mixing for 1–72 hours prior to further purification steps.

To clarify the refolded M-CIF solution, a previously prepared tangential filtration unit equipped with 0.16 μm membrane filter with appropriate surface area (Filtron), equilibrated with 40 mM sodium acetate, pH 6.0 was employed. The filtered sample was loaded onto a cation exchange of POROS HS-50 resin (Perseptive Biosystems). The column was washed with 40 mM sodium acetate, pH 6.0 and eluted with 250 mM, 500 mM, 1000 mM, and 1500 mM NaCl in the same buffer, in a stepwise manner. The absorbance at 260 nm and 280 nm of the effluent was continuously monitored. Fractions were collected and further analyzed by SDS-PAGE.

Those fractions containing the desired protein were then pooled and mixed with 4 volumes of water. The diluted sample was then loaded onto a previously prepared set of tandem columns of strong anion (POROS HQ-50, Perseptive Biosystems) and weak cation (POROS CM-20, Perseptive Biosystems) exchange resin. The columns were equilibrated with 40 mM sodium acetate, pH 6.0. Both columns were washed with 40 mM sodium acetate, pH 6.0, 200 mM NaCl. The CM-20 column was then eluted using a 10 column volume linear gradient ranging from 0.2 M NaCl, 50 mM sodium acetate, pH 6.0 to 1.0 M NaCl, 50 mM sodium acetate, pH 6.0. Fractions were collected under constant A280 monitoring of the effluent. Those fractions containing the protein of interest (determined by SDS-PAGE) were then pooled.

The resultant M-CIF was of greater than 95% purity after the above refolding and purification steps. No major contaminant bands were observed from the Coomassie Blue stained 16% SDS-PAGE gel when 5 μg of purified protein was loaded. The purified protein was also tested for endotoxin/LPS contamination. The LPS content was less than 0.1 ng/ml according to LAL assays.

Example 6: Purification of FGF-13 from E. coli

The coding sequence of FGF-13 was amplified by PCR during which unique restriction sites SphI and HindIII were introduced and then cloned into the E. coli expression vector pQE7. The resulting plasmid DNA was used to transform E. coli M15 Rep4 host cells. Cell cultures were prepared as described in Example 1. FGF-13 (HODAH63) protein, was produced in E. coli transformant as two bands in modest amount with IPTG induction.

The purification involves the following steps, and unless otherwise specified, all procedures were conducted at 4–10° C.

Solubilization of FGF-13 from E. coli

FGF-13 was produced as insoluble protein deposited in inclusion bodies. Upon completion of the production phase the E. coli fermentation, the cell culture was cooled to 2–10° C. and the cells were harvested by continuous centrifugation at 15,000 rpm (Heraeus Sepatech). Per gram of E. coli cell paste was resuspended in 10 ml buffer containing 100 mM Tris-HCl pH 7.5, 50 mM EDTA using a shear mixer.

The cells were lyzed in a microfluidzer (Microfluidics, Corp. or APV Gaulin, Inc.) at 4,000–12,000 psi twice. The homogenate was mixed with a NaCl solution to a final concentration of 0.5 M NaCl, followed by centrifugation at 7,000×g for 15 minutes. The resulting pellet was washed again using 100 mM Tris-HCl pH 7.4, 50 mM EDTA, 0.5 M NaCl, followed by centrifugation at 7000×g for 15 min.

The washed inclusion bodies (pellet) were extracted with 2 M GuHCl in 50 mM Tris pH7.5, 25 mM EDTA for 2–4 hours. After centrifugation at 7000×g for 15 minutes, the FGF-13 containing supernatant was placed at 2–10° C. overnight followed by centrifugation at 30,000×g for 20 minutes. This supernatant which contains 60–80% FGF-13 is called the 2 M GuHCl extract.

Refolding

The 2M GuHC1 extract was refolded by quickly mixing the GuHCl extract by vigorously stirring for 30 minutes with 20 volumes of a buffer containing 50 mM Tris pH7.5, 25 mM EDTA, 200 mM NaCl, 20 μg/ml Pefabloc SC, 2 μg/ml E-64 (Boehringer Mannheim). The mixture was placed at 2–10° C. without mixing for 1–48 hours.

Liquid Chromatographic Purification of FGF-13

The refolded FGF-13 was clarified through a 0.16 μm tangential filtration unit. The filtered sample was applied to a POROS HS-50 (PerSeptive Biosystem) cation exchange column at pH7.5. The HS column was washed with a buffer containing 50 mM Tris pH 7.5, 0.5M NaCl, and eluted with 750 mM, 1.2 M, and 1.5 M NaCl steps. FGF-13 was eluted in the 1.5 M NaCl step.

The HS purified FGF-13 was diluted 4-fold, then applied onto a set of POROS HQ-50/POROS CM-20 (PerSeptive Biosystem) anion/cation columns in a tandem chromatographic mode. Both columns were washed with a buffer containing 50 mM Tris pH 7.5, 400 mM NaCl. The CM column was eluted with a 20 column volume of 0.4 M to 1.25 M NaCl linear gradient. FGF-13 was eluted with approximately 700 mM NaCl, and finished with a S200 Sepharcryl HR (Pharmacia) size exclusion column at greater than 95% purity.

Results

FGF-13 transformed *E. coli* produced two bands after IPTG induction. After cell lysis, FGF-13 protein was extracted with GuHCl from the insoluble fraction as described in the method section. The GuHCl extracted protein appears to be the same size as the starting material on SDS-PAGE and is greater than 60% pure. However, two additional minor bands which seem to be 2 kD smaller than the original two bands appeared on SDS-PAGE after refolding. Proteolytic degradation might occur during refolding and four bands are present.

Refolded FGF-13 was captured by a strong cation exchange POROS HS-0 50 column and eluted at 90% purity with 1.25 to 1.5M NaCl. The resulted protein was passed through a set of tandem columns consisted of a strong anion exchange (POROS HQ-50) column and a weak cation exchange (POROS CM-20). FGF-13 was eluted from the CM column with 700–800 mM NaCl. At least four different bands at MW 18–22 kD appear on reduced SDS-PAGE in the CM purified FGF-13 (FIG. 10). All four bands are confirmed to be FGF-13 protein by N-terminal sequence analysis.

| | |
|---|---|
| The upper 1st band: | MQGEN (SEQ ID NO:1) N-terminus |
| The upper 2nd band: | MQGEN (SEQ ID NO:1) N-terminus |
| 3rd and 4th bands: | TDQLS (SEQ ID NO:2) 21 residues shorter than above |

From the above results, it was expected that the C-terminal degradation might occur to the 2nd and the 4th bands. The cleavage site was determined based on mass through Mass Spec analysis. It was concluded that 9 amino acid residues were removed at the C-terminus from a small percentage of the protein.

Example 7: Biological Activity of MPIF-1 Purified by the Inventive Process

MPIF-1 protein has been expressed in baculovirus, *E. coli* and CHO expression systems and purified to >95% homogeneity as determined by Coomassie Blue staining of an SDS-PAGE gel. The mammalian expressed and purified protein was composed of 99 amino acids with an RVT-KDAE amino acid sequence at the N-terminus and contained neither mannose nor N-acetylglucosamine, as expected from the absence of consensus N-linked glycosylation sites in the deduced primary amino acid sequence. Purified MPIF-1 from *E. coli* has an additional methionine followed by the "RVTKDAE" (SEQ ID NO:4) MPIF-1 sequence at the N-terminus. Purified MPIF-1 from baculovirus, *E. coli* and CHO expression systems have been found to stimulate chemotaxis of T-lymphocytes and granulocytes in vitro, induce a transient rise in the intracellular calcium concentration in monocytes, and inhibit colony formation by mouse bone marrow derived Low Proliferative Potential Colony-Forming Cells (LPP-CFC) in vitro.

To demonstrate that MPIF-1 purified according to the process of the present invention is biologically active, the following in vitro and in vivo experiments were performed.

Materials and Methods

Reagents and chemicals:

Hanks Balanced Salt Solution (HBSS), IMDM, and MEM tissue culture media were purchased from Life Technologies Inc., Gaithersburgh, Md. Fetal bovine serum (FBS), Histopaque 1077, and Histopaque 1119 were purchased from Sigma Tissue Culture Products, St. Louis, Mo. MyeloCult™ H5100 and MethoCult™ H4535 growth medium for culturing hematopoietic progenitors were purchased from Stem Cell Technologies Inc., Vancouver, BC, Canada. Human and murine recombinant cytokines were all purchased from R and D Systems Inc., Minneapolis, Minn. QBEND/10 CD34 cell isolation kit, Type RS columns, and VarioMac were purchased from Miltenyi Biotech Inc., Sunnyvale, Calif. All the monoclonal antibody reagents against the human hematopoietic cell surface antigens were purchased from Becton Dickinson Immunocytometry Systems, San Jose, Calif.

Mouse bone marrow cells:

Mouse bone marrow cells (MBMC) were isolated from the femur and tibia of 6–8 week old, female, C57Bl/6 mice (Jackson Laboratories, Barharbor, Mass.) by flushing with IMDM supplemented with 5% FBS. A low density fraction of the cell population was then obtained by centrifuging (750×g for 30 min. at 23° C.) the cell suspension over a cushion of Histopaque (1.119 gm/ml). Cells sedimenting at the interface of the medium and the ficoll were washed three times with IMDM growth medium, plated in a 10 cm diameter tissue culture dish (Costar, Cambridge, Mass.), and then incubated for 1 hour at 37° C. in a tissue culture incubator to remove cells capable of adhering to the treated

```
                     Full length sequence of FGF-13

75%                  20%
                          MQGEN (SEQ ID NO:1)  TDQLS (SEQ ID NO:2)
                          ::::                 :::::
MGAARLLPNL  TLCLQLLILC  CQTQGENHPS  PNFNQYVRDQ  GAMTDQLSRR
QIREYQLYSR  TSGKHVQVPG  RRISATAEDG  NKFAKLIVET  DTFGSRVRIK
GAESEKYICM  NKRGKLIGKP  SGKSKDCVFT  EIVLENNYTA  FQNARHEGWFMV
FTRQGRPRQA  SRSRQNQREA  HFIKRLYQGQ  LPFPNHAEKQ  KQFEFVGSAP
TRRTKRTRRP  OLPT (SEQ ID NO:3)
``` polystyrene surface. The resulting non-adherent populations of cells were then used as target cells in clonogenic assays. For some experiments, MBMC's were enriched by negative immunoselection for primitive hematopoietic progenitors. Briefly, a low density fraction of MBMC's were treated at 4–8° C. with a panel of rat monoclonal antibodies against murine antigens (CD11b, CD4, CD8, CD45R, and Gr. 1). Antibody-bound, committed hematopoietic precursors and mature cells were then removed by incubation with immunomagnetic beads. The resulting populations of cells, referred to as lineage-depleted populations of cells (Lin$^-$ cells), is typically 60- to 80-fold enriched for High Proliferative Potential Colony-Forming Cells (HPP-CFC) as determined by clonogenic assays (see below).

CD34$^+$human hematopoietic stem cells:

CD34 cells were isolated from human cord blood by immunoselection using QBEND/10 Cell Isolation Kit and high-gradient magnetic cell sorting according to the manufacturers instructions. Briefly, 45 ml of cord blood was collected in 5 mM EDTA solution with 20 U/ml heparin and centrifuged at 200×g for 10 minutes at 23° C. The buffycoat was then resuspended in PBS supplemented with 5 mM EDTA and centrifuged on Histopaque (density 1.077 g/ml). PBMCs were collected by harvesting the interface band and washed three times with PBS containing 5 mM EDTA, resuspended in ice cold PBS with 5 mM EDTA and 0.5% BSA, and then subjected to the QBEND/10 Cell Isolation protocol. Typically, this procedure yielded a population of cells that was 95% CD34$^+$as determined by FACScan.

Clonogenic assays on mouse bone marrow cells:

HPP-CFC and LPP-CFC colony formation assays were performed in a two-layered agar culture system. Briefly, the bottom layer was prepared in 3.5 cm diameter tissue culture dishes with 1 ml of MEM medium supplemented with 20% FBS, 0.5% Difco agar, and a panel of recombinant cytokines that consisted of mouse IL-3 (7.5 ng/ml), mouse SCF (75 ng/ml), human M-CSF (7.5 ng/ml), and mouse IL-1 a (15 ng/ml). Chemokines were also incorporated into the bottom agar where indicated. This layer was then overlayed with 0.5 ml of murine bone marrow cell suspension (1,500 cells/dish) prepared in the agar medium described above except that it contained 0.3% agar and no cytokines. The dishes were then incubated for fourteen days in a tissue culture incubator (37° C., 88% $N_2$, 5% $CO_2$, and 7% $O_2$) and colonies were scored under an inverted microscope.

The above combination of cytokines typically stimulates colony formation by two classes of progenitors; HPP-CFC is a primitive, multipotential progenitor that exhibits many properties of hematopoietic stem cells and gives rise to a colony of >5 mm in diameter, whereas LPP-CFC is a committed progenitor which differentiates along the granulocyte and monocyte lineages and gives rise to colonies that are <1 mm in diameter. In some experiments the impact of MPIF-1 on the growth of BFU-E, CFU-E, and CFU-GM was also determined. Bone marrow cells ($5 \times 10^4$ cells) were suspended in 1.0 ml of MethoCult semisolid medium in 3.5 cm diameter tissue culture dishes. For CFU-E assays, the above medium was supplemented with recombinant human Epo at 3 U/ml and the dishes were incubated as above for two days. After this two day incubation, hemoglobinized colonies (4–16 cells/colony) were identified by acid benzidine stain and scored under an inverted microscope using bright-field optics. For BFU-E and CFU-GM assays, the above medium was supplemented with recombinant mouse IL-3 (5 ng/ml), GM-CSF (10 ng/ml), and Epo (3 U/ml) and the dishes were incubated for eleven days. Colonies were then scored as above using an inverted microscope.

Animal studies:

Twelve to fifteen weeks old, female, C57Bl/6 mice purchased either from Jackson Laboratories or Harlan Industries were utilized throughout all experiments reported here. Mice were fed a standard diet and housed under standard conditions of lighting, temperature, and air. Neutropenia was induced by administering (I.P.) a single dose of freshly prepared 5-Fu solution (in warm distilled water) at 150 mg/Kg body weight. In some experiments, two doses of 5-Fu were administered at the above dosage. Blood was collected from mice either from the tail vein or periorbital sinus in tubes containing 20 U/ml sodium heparin and 5 mM disodium EDTA as anticoagulants. White blood cell (WBC) counts in the peripheral blood was determined using a Coulter counter.

Results

MPIF-1 inhibits colony formation by LPP-CFC

Clonogenic assays were performed, where a limiting number of low density population of mouse bone marrow cells were plated in methylcellulose-or agar containing growth medium supplemented with appropriate combinations of cytokines to demonstrate the effect of MPIF-1 purified according to the present invention on hematopoietic cell differentiation. No colonies were detected, of any kind, either in the absence of any added cytokines or in the presence of MPIF-1 alone. However, the numbers of cytokine stimulated CFU-GM and LPP-CFC colonies in the presence of MPIF-1 were decreased to 30% of those found in the control cultures (Table 6). The inhibitory effect of MPIF-1 appeared to be specific, as MPIF-1 had no effect on colony formation by CFU-E, BFU-E, and HPP-CFC (Table 6). MCP4, a β-chemokine which was also expressed and purified by the process of the present invention as MPIF-1, had no effect on colony formation by CFU-GM, CFU-E, BFU-E, LPP-CFC, and HPP-CFC (Table 6). Thus, as anticipated, the inhibitory effect of MPIF-1 was specific to LPP-CFC and this effect is not due to a contaminant copurified in the MPIF-1 preparation.

Figure 14A:
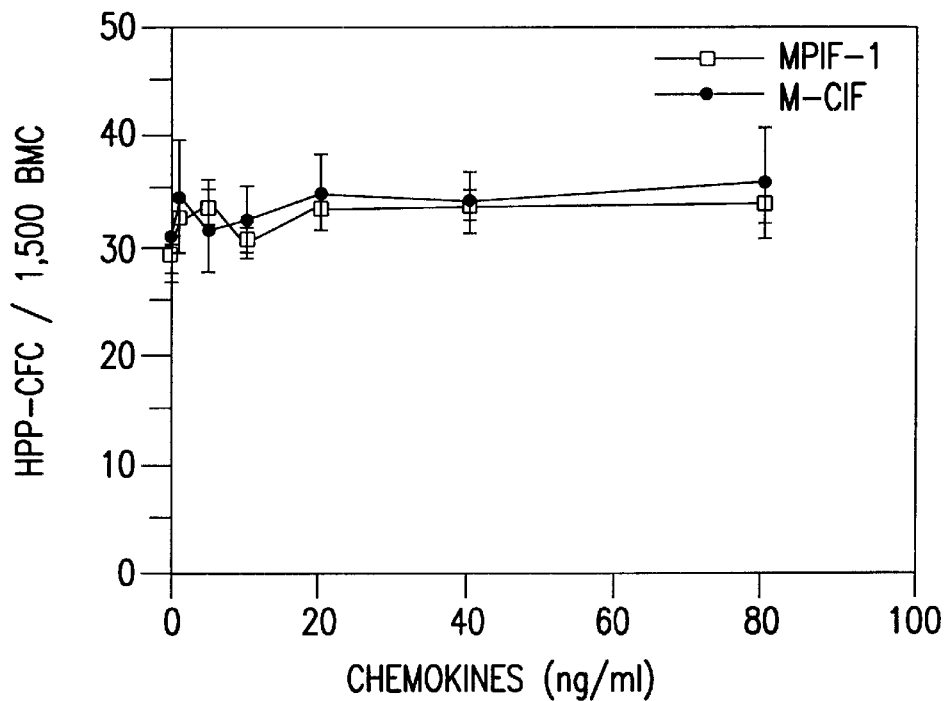
FIG. 14A and 14B show the effects of MPIF-1 concentration on the growth and differentiation of HPP-CFC and LPP-CFC. A low density population of mouse bone marrow cells was plated (1,500 cells/dish) in agar containing medium with or without the indicated concentrations of the chemokines, but in the presence of IL-3 (5 ng/ml), SCF (100 ng/ml), IL-1 alpha (10 ng/ml), and M-CSF (5 ng/ml). Colonies were counted after 14 days. Data shown are pooled from two independent experiments and are expressed as Mean +/–S.D. The results show that MPIF-1 purified according to present invention inhibits growth of LPP-CFC colonies in a dose-dependent fashion.
Figure 14B:
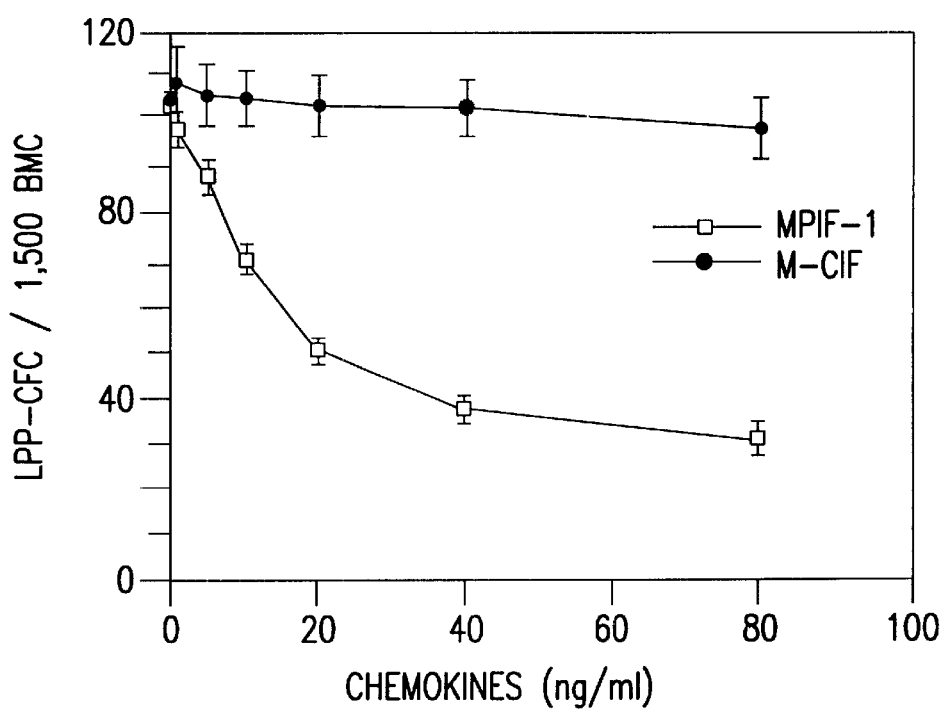
Figure 15:
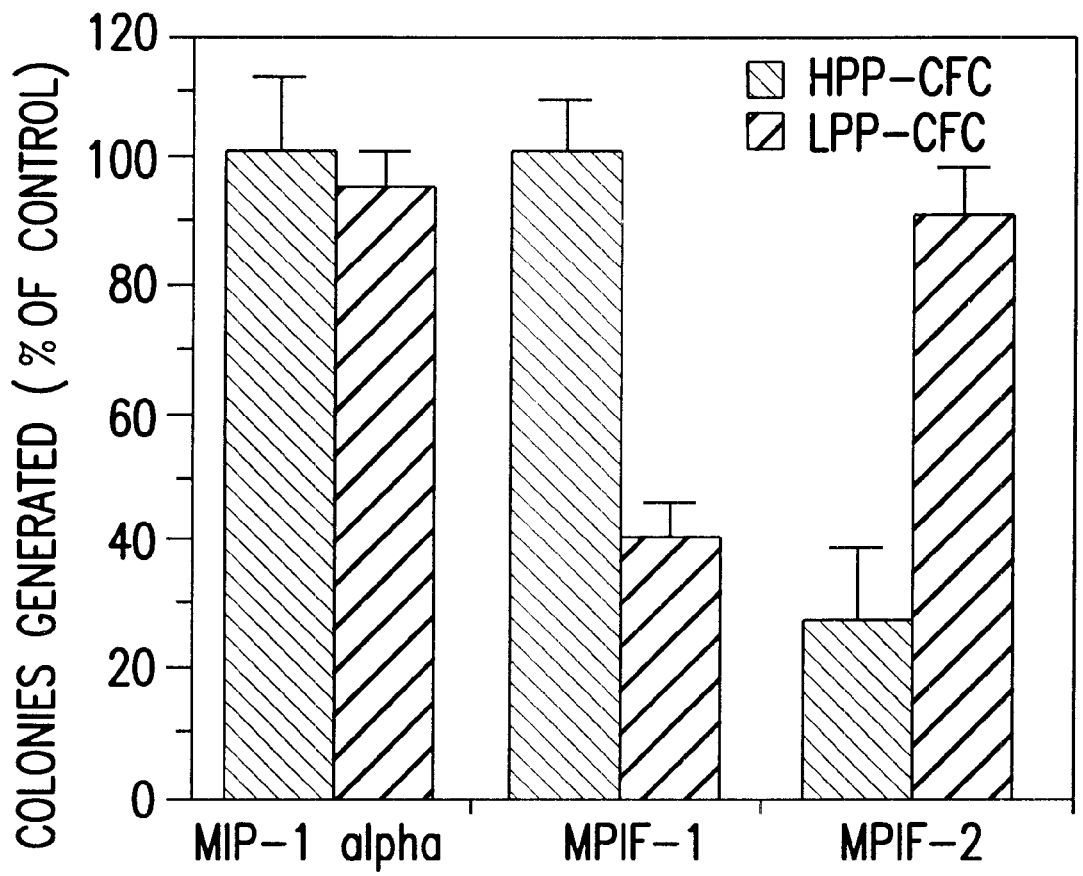
FIG. 15 shows a comparison of MPIF-1 and MIP-1α effects on colony formation by HPP-CFC and LPP-CFC. A low density population of mouse bone marrow cells was plated (1,500 cells/dish) in agar containing medium with or without the indicated chemokines (100 ng/ml) plus standard cytokine cocktail as used for the HPP-CFC and LPP-CFC assay. The number of colonies generated in the presence of chemokines is expressed as a mean percentage of those produced in the absence of any added chemokines. Data shown are pooled from two independent experiments and are expressed as Mean +/–S.D. The results demonstrate that MPIF-1 purified according to the present invention inhibits colony formation by LPP-CFC, but not HPP-CFC.

LPP-CFC colony formation was inhibited in a dose-dependent manner in the presence of MPIF-1 purified according to the present invention; compared to the control there was 50% reduction in the number of colonies at 20 ng/ml MPIF-1 and 73% reduction at 80 ng/ml (FIG. 14B). No further increase in the inhibition of LPP-CFC colony formation was observed when this preparation of MPIF-1 was tested up to 500 ng/ml (data not shown). As expected, M-CIF in the same assay had no effect on either LPP-CFC or HPP-CFC (FIG. 14B) and MPIF-1 had no effect on HPP-CFC (FIG. 14A). Thus, there exists a small ~20%) but significant percentage of LPP-CFC's in the bone marrow that appear to be not inhibited by MPIF-1. MIP-1α has been shown to inhibit the growth of multipotential hematopoietic progenitors. Also, MIP-1α is most homologous to MPIF-1 within the β-chemokine family. Therefore, MIP-1α was tested but it had no effect on either LPP-CFC or HPP-CFC colony formation, whereas MPIF-1, as shown above, inhibited LPP-CFC colony formation (FIG. 15).

MPIF-1 inhibits proliferation of human CD34$^+$progenitors

Figure 16:
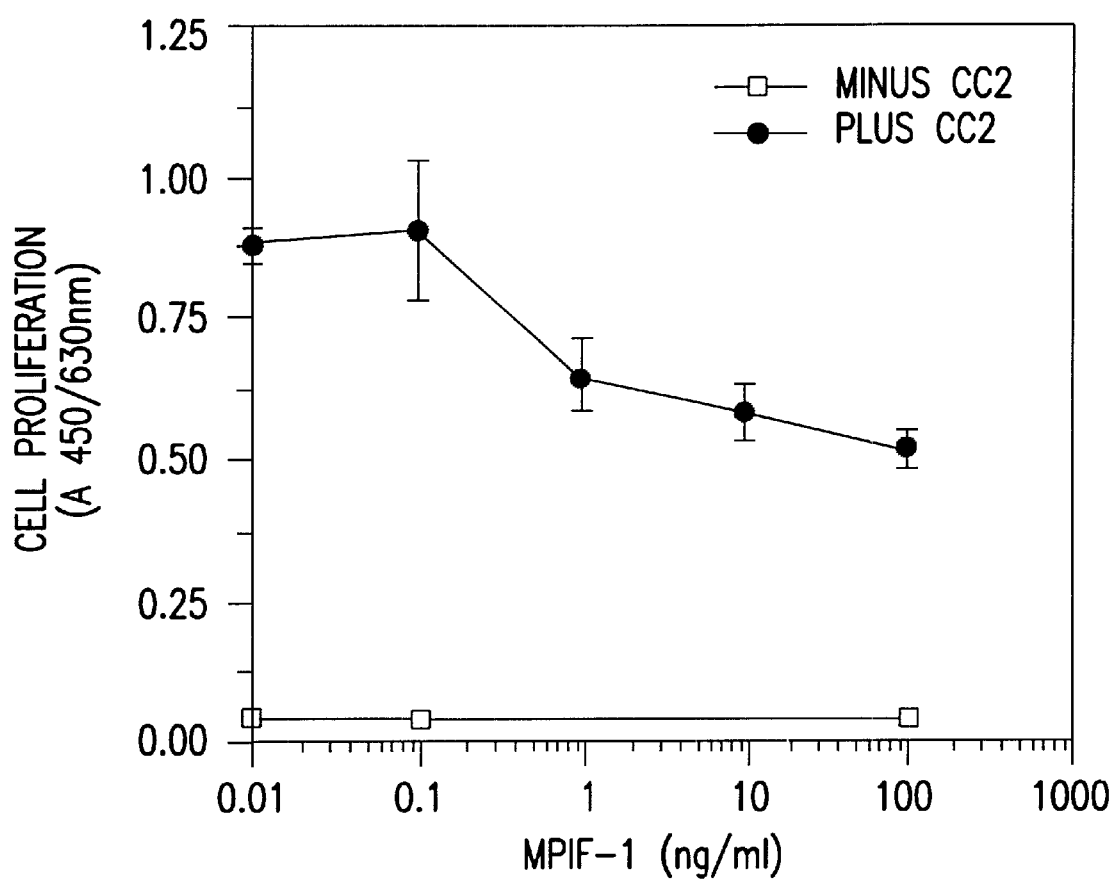
FIG. 16 shows the effect of MPIF-1 on the cytokine-induced proliferation of human hematopoietic progenitor cells in vitro. Hematopoietic progenitors were obtained by culturing human cord blood CD34+ stem cells in the presence of IL-3 (10 ng/ml) and SCF (50 ng/ml) for four days in liquid culture. These cells were then plated (5,000 cells/well) in a 96-well plate in 0.2 ml of growth medium containing the indicated concentrations of MPIF-1 either in the presence or absence of a cytokine cocktail (CC2) consisting of IL-3 & GM-CSF (1 ng/ml each), SCF (5 ng/ml) & erythropoietin (3 U/ml). Cells were then allowed to grow in a tissue culture incubator for six days at which point the numbers of cells in each well was quantitated colorimetrically using the WST-1 reagent. Data from one out of three representative experiments are shown as Mean absorbance +/–S.D. of assays that were performed in triplicates. Note that 0.01 ng/ml represents no added MPIF-1.

The data presented above demonstrates that human MPIF-1 purified according to the present invention has biological activity in regards to murine hematopoietic progenitor. To assess whether human MPIF- 1 purified according to the present invention has biological activity in regards to human cells, CD34$^+$hematopoietic stem cells were isolated from human cord blood and cultured for four days in the presence of IL-3 and SCF. The resulting populations of cells, consisting of myeloid progenitors, were then allowed to undergo proliferation and differentiation for six additional days in the presence or absence of multiple cytokines plus various concentrations of MPIF-1 purified according to the present invention. As shown in FIG. 16, there was little proliferation of cells either in the absence of cytokines or in the presence of MPIF-1 alone. Addition of cytokines resulted in a ~40-fold increase in total cells and this cytokine stimulated proliferation of cells was inhibited, in a dose-dependent manner, by MPIF-1 (FIG. 16). Clonogenic assays also demonstrated that CFU-GM induced colony formation was sensitive to MPIF-1, as shown above with murine cells (Table 6). Thus, as anticipated, MPIF-1 purified according to the present invention inhibits growth of myeloid progenitors of both murine and human origin.

MPIF-1 protects myeloid progenitors from 5-Fu-induced cytotoxicity in vitro

Figure 17:
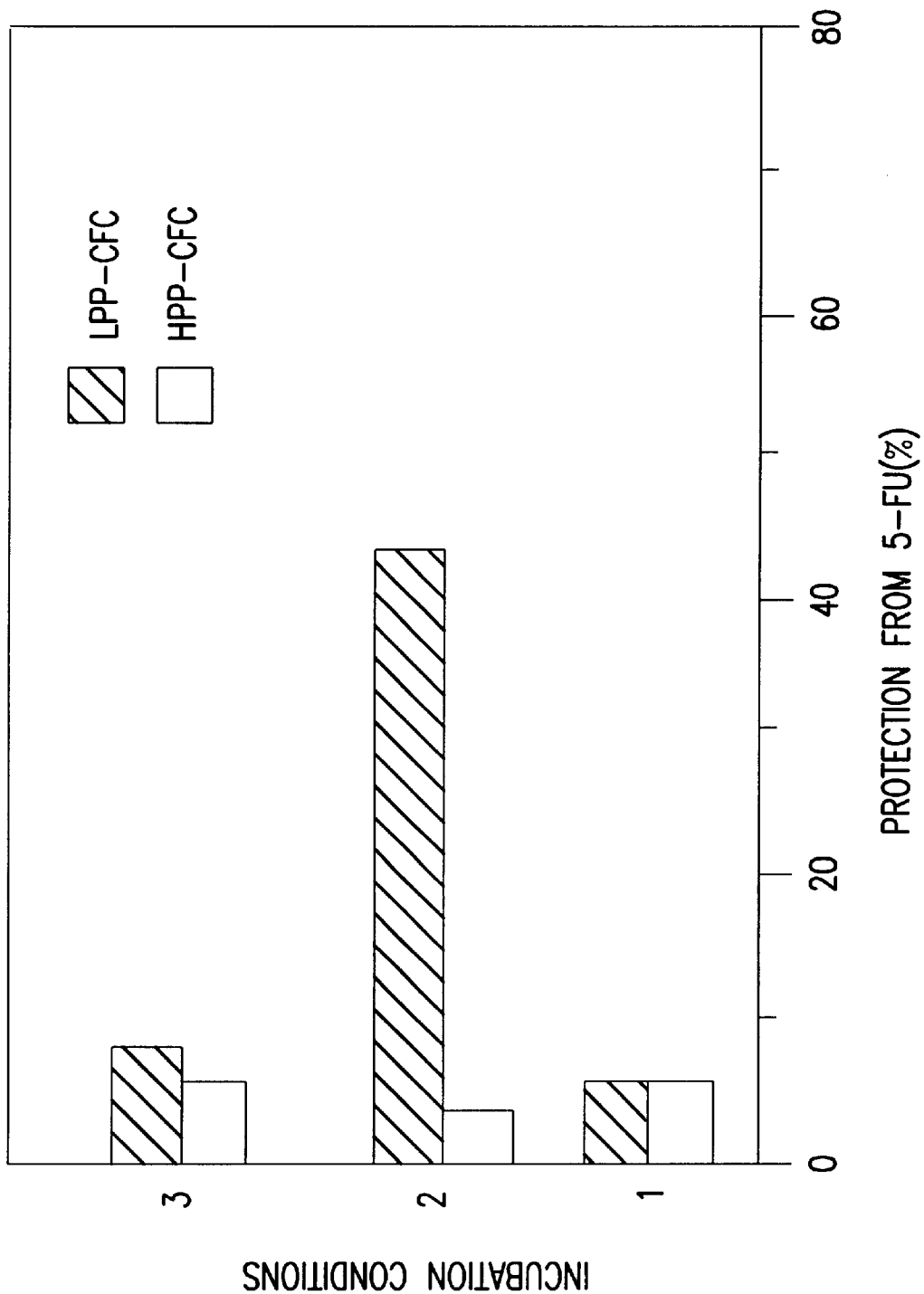
FIG. 17 shows the effect of MPIF-1 on the 5-Fu-induced cytotoxicity against HPP-CFC and LPP-CFC in in vitro liquid cultures. Lin$^1$ populations of mouse bone marrow cells were resuspended ($1\times10^5$ cells/ml) in a growth medium containing IL-3 (5 ng/ml), SCF (50 ng/ml), GM-CSF (5 ng/ml), M-CSF (5 ng/ml) and IL-1a (10 ng/ml) and 1 ml of this cell suspension was dispensed into culture tubes. (1) A set of duplicate cultures received no chemokine; (2) duplicate cultures with MPIF-1 at 100 ng/ml; and (3) duplicate cultures with an irrelevant protein (i.e, MIP-4 (chemokine β-7), a chemokine previously tested to be not active in both HPP-CFC and LPP-CFC assay and is used as a negative control) at 100 ng/ml. All cultures were incubated in a tissue culture incubator for 48 hours, at which point one culture from each set received 5-fluorouracil (5-Fu) at 100 µg/ml and incubation was continued for additional 24 hours. All cultures were then harvested, washed three times with HBSS, and then assayed for the presence of the HPP-CFC & LPP-CFC. Percent protection is expressed as number of colonies detected in cultures incubated in the presence of 5-Fu divided by the number of colonies found in cultures incubated without 5-Fu×100. Data from one out of two representative experiments are shown and are expressed as Mean ±SD of assays that were performed in duplicates.
Figure 18:
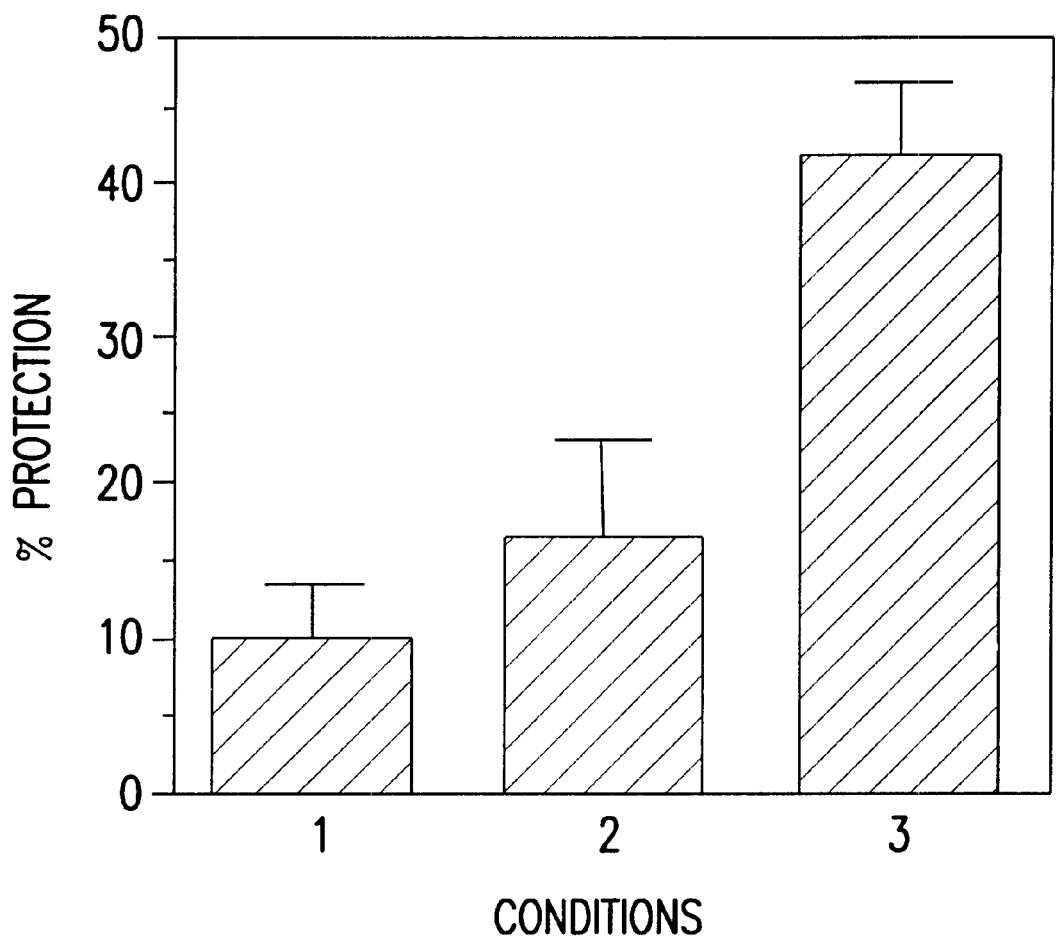
FIG. 18 shows the effect of MPIF-1 on the survival of human hematopoietic progenitors from 5-Fu-induced cytotoxicity in vitro. CD34+ cells ($5\times10^4$/ml) were cultured in 2 ml of growth medium supplemented with IL-3 (10 ng/ml) and SCF (50 ng/ml) in the absence of any chemokine (1) and in the presence of MIP-1α (2) or MPIF-1 at 10 ng/ml (3). After allowing cells to grow for four days, each culture was equally split into two cultures. One culture of each set received 5-Fu at 25 µg/ml and the other served as a control. Both sets of cultures were then incubated for one additional day. All cultures were then harvested, washed three times with HBSS, and then assayed in triplicate in a 96-well cell proliferation assay to determine proliferative potential in the presence of IL-3 (10 ng/ml), GM-CSF (10 ng/ml), and SCF (50 ng/ml). Plates were incubated in a tissue culture incubator for six days and the total number of cells in each well was then determined colorimetrically using WST-1 reagent. Percent protection equals mean absorbance in the presence of 5-Fu/mean absorbance in the absence of 5-Fu×100. Data from one out of two representative experiments are shown as mean % protection ±S.D.
Figure 19:
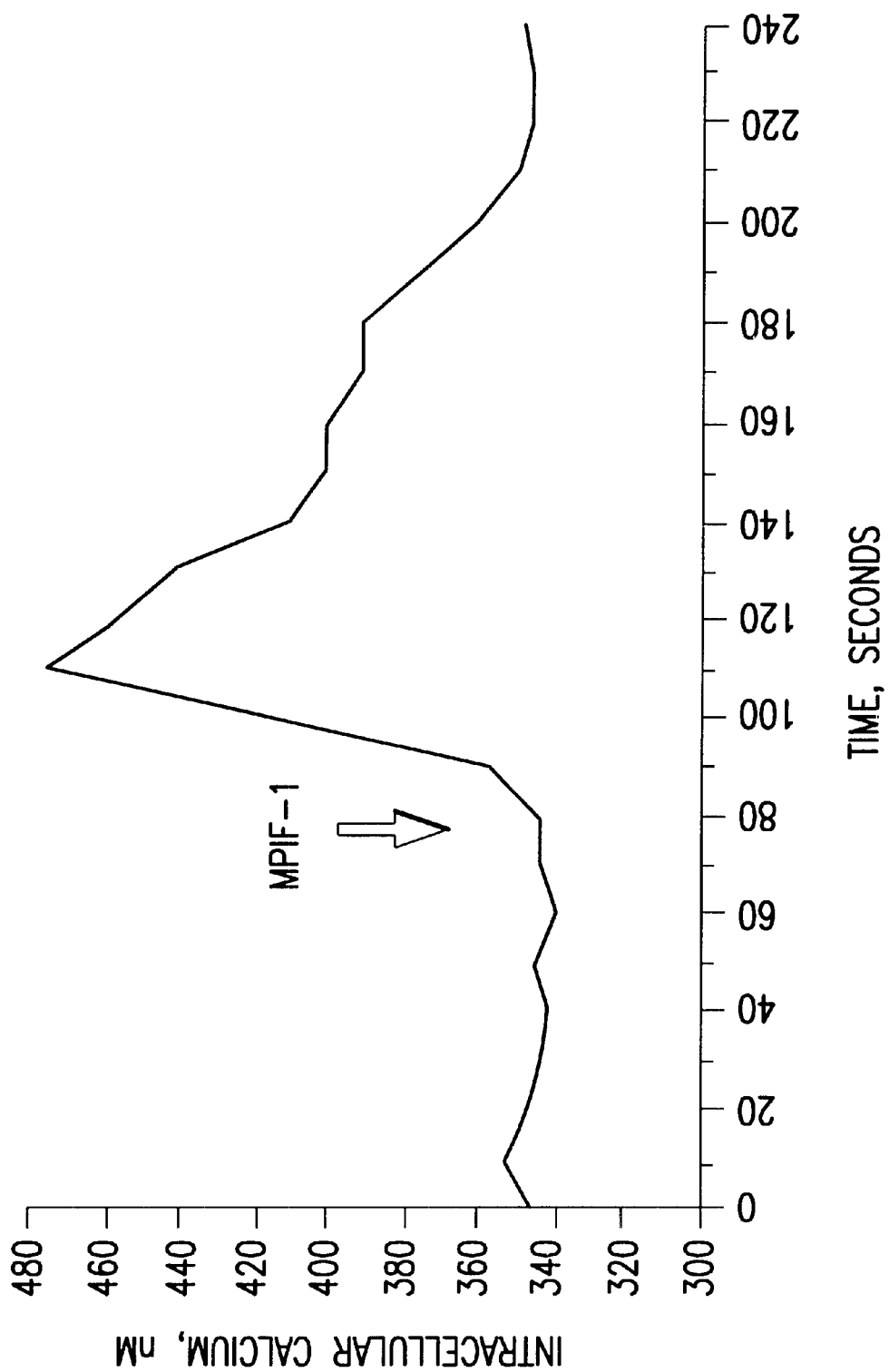
FIG. 19 shows calcium mobilization by MPIF-1 in THP-1 cells. MPIF-1 induces calcium mobilization in human THP-1 cells in vitro. THP-1 cells were exposed to 100 ng/ml MPIF-1 at the indicated time. MPIF-1 induced a rapid mobilization of calcium in the THP-1 cells.

To demonstrate that the inhibitory effect of MPIF-1 purified according to the present invention can lead to the protection of LPP-CFC from the cytotoxicity of the cell cycle acting chemotherapeutic drug 5-Fu, lineage-depleted populations of cells (Lin⁻cells) were isolated from mouse bone marrow and incubated in the presence of multiple cytokines with or without MPIF-1. After 48 hours, one set of each culture received 5-Fu and the incubation was then continued for an additional 24 hours. After the 24 hour incubation, the numbers of surviving LPP-CFC were determined by a clonogenic assay. As shown in FIG. 17, ~40% of LPP-CFC were protected in the presence of MPIF-1 from the cytotoxic effects of 5-Fu, whereas little protection (<5%) of LPP-CFC was observed in the absence of MPIF-1 or in the presence of an unrelated protein. HPP-CFC under the same culture conditions were not protected by MPIF-1, demonstrating the specificity of the MPIF-1 effect. A similar experiment was also performed with human $CD34^+$cells, where protection from the 5-Fu-induced cytotoxicity was determined by measuring proliferative capacity of the survival of cells in response to multiple cytokines. Data presented in FIG. 18 demonstrates that progenitors capable of responding to multiple cytokines were protected by about 40% in the presence of MPIF- 1, with little protection observed either in the absence of any added chemokine or in the presence of MIP-1α. Together, these data demonstrate that MPIF-1, isolated by the method of the present invention, is biologically active.

Effect of MPIF-1 treatment in normal mice

To determine the effect of administering MPIF-1 purified according to the present invention on hematopoietic parameters in vivo, four mice were injected IP twice a day at 8 hours intervals for two days with either MPIF-1 (0.5 mg/Kg/injection) or saline. Approximately 12 hours after the last injection, peripheral blood and bone marrow cells were obtained from each of the animals and then assayed for the presence of HPP-CFC and LPP-CFC. Table 7 shows pooled data obtained from four animals in each group and are expressed as Mean±S.D. Frequency of progenitors in the peripheral blood was not affected in response to MPIF-1 injections. However, the frequency of LPP-CFC in the bone marrow of the MPIF-1 injected animals was significantly reduced compared to that found in animals injected with saline (Table 7).

Effect of MPIF-1 pre-treatment of mice on the recovery from 5-Fu-induced neutropenia The results shown above suggested that the myelotoxicity elicited by cytotoxic drugs such as 5-Fu, a severe side effect frequently observed in cancer patients undergoing chemotherapy, might be ameliorated if the critical cell types within the bone marrow could be protected during the period of action of the chemotherapeutic drugs by MPIF-1 purified according to the present invention. To explore this possibility, a group of mice (Group 4) were injected (I.P.) daily for three days, at 24 hour intervals, with 1.0 mg/Kg MPIF-1. On the third day these mice were also injected (I.P.) with 5-Fu at 150 mg/Kg. Animals injected with either saline (Group 1), MPIF-1 alone (Group 2), or 5-Fu alone ( Group 3) served as controls. Four animals from each of the groups were sacrificed at 3, 6, & 10 days post 5-Fu administration to determine White Blood Cell (WBC) counts in the peripheral blood. As shown in Table 8, injection of MPIF-1 alone had little effect on the WBC counts. As expected, 5-Fu treatment resulted in a dramatic reduction in the circulating WBC counts on day 6 post 5-Fu administration compared to animals injected with saline. Significantly, animals treated with MPIF-1 prior to 5-Fu administration exhibited about two fold higher WBC counts in the blood compared to animals treated with 5-Fu alone. Thus, treatment of mice with MPIF-1 prior to 5-Fu apparently resulted in an accelerated recovery from neutropenia.

Effect of MPIF-1 pre-treatment on the bone marrow recovery

Hematopoietic stem and multipotential progenitor cells in the bone marrow are responsible for restoring all the hematopoietic lineages following chemotherapy. In normal individuals, these cells divide less frequently and are therefore spared from a single dose of a chemotherapeutic drug. However, these cells are killed if a second dose of the drug is administered within three days after the first dose is administered as the critical cell types in the bone marrow are rapidly dividing during this period. To demonstrate that MPIF-1 purified according to the present invention is able to protect these cell types in the bone marrow, the following experiment was performed as illustrated below.

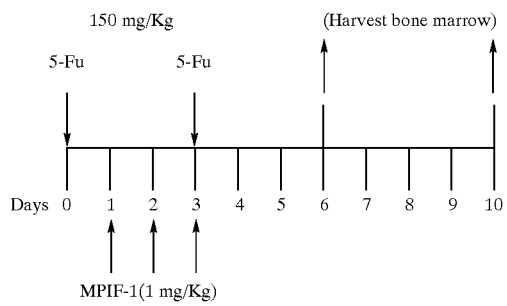

Three groups of mice (9 animals per group) were treated as follows: Group 1 was injected with saline on days 1, 2, and 3; Group 2 was injected with 5-Fu on days 0 and 3; and Group 3 was injected with 5-Fu on days 0 and 3 and MPIF-1 on days 1, 2, and 3. Four animals from each group were bled and their bone marrow harvested 3 and 7 days post second 5-Fu administration to determine WBC counts, bone marrow cellularity, and HPP-CFC and LPP-CFC frequencies in the bone marrow using a clonogenic assay. As shown in Table 9, injection of two doses of 5-Fu to mice resulted in a dramatic reduction in the peripheral blood WBC counts, total bone marrow cellularity, and HPP-CFC and LPP-CFC frequencies compared to that in the saline-injected animals at 3 days post second 5-Fu administration. These parameters were not significantly affected at 3 days post second 5-Fu in animals pre-treated with MPIF-1 (Table 9). The most pronounced effect of MPIF-1 pre-treatment, especially with respect to the progenitor frequencies, was observed at 7 days post second 5-Fu administration; HPP-CFC and LPP-CFC frequencies in 5-Fu treated mice were still at <50% of the control levels, whereas these progenitor frequencies in mice pre-treated with MPIF-1 had been restored to those found in the saline injected control animals (Table 9). A consistent finding has been the apparent recovery of HPP-CFC from the 5-Fu-induced cytotoxicity in the MPIF-1 pre-treated animals. This is a surprising result since MPIF-1 had no impact on colony formation by HPP-CFC in vitro.

Induction of Calcium Mobilization by MPIF-1 in Human Monocytes

Many cell-surface receptors transmit their signals via G-proteins activate phosphoinositidase C, which catalyzes the hydrolysis of phosphatidylinositol 4,5-bis-phosphate to the second messengers, inositol 1,4,5-triphosphate ($IP_3$) and diacylglycerol. $IP_3$ interacts with a specific receptor population of ligand-gated channels to mobilize non-mitochondrial intracellular $Ca^{++}$ stores (calciosomes and endoplasmic reticulum). The Indo-1 assay utilizes the highly fluorescent $Ca^{++}$-indicator dye Indo-1 to detect the release and uptake of native $Ca^{++}$ from the intracellular $Ca^{++}$ stores. Indo1 excitation is at 330 nm while detection of bound dye is measured at 405 nm and free dye is measured at 485 nm.

Chemokines play fundamental roles in the physiology of acute and chronic inflammatory processes by attracting and stimulating leukocytes. The actions of chemokines are mediated by G protein-coupled receptors. Transient increases in cytosolic free calcium are early events in signal transduction during leukocyte activation with chemokines. Therefore, the Indo-1 calcium mobilization assay can be used to assess the effects of MPIF-1 purified according to the present invention on leukocytes.

Methods

Cells.

A human monocytic-like cell line THP-1 was obtained from the American Type Culture Collection (ATCC TIB 202) and maintained in RPMI-1640 medium supplemented with 10% FCS. Human peripheral blood monocytes were purified from normal blood by elutriation. The monocyte preparations were 60–80% pure as assessed by monocyte-specific antibody staining.

Analysis of intracellular calcium mobilization.

Human monocytes or THP-1 cells were loaded with Indo-1 by incubation for 30 minutes at 37° C. with 2.5 μM Indo-1 acetoxymethylester per $10^7$ cells in HBSS containing 1 mM $CaCl_2$, 2 mM $MgSO_4$, 5 mM glucose and 10 mM HEPES. The cells were washed with HBSS and resuspended in the same buffer at $2–5\times10^5$ cells/ml and stimulated with the indicated chemokines at 37° C. The fluorescence signals relating to changes in intracellular calcium ($[Ca^{++}]_i$) were measured using a Hitachi F-2000 fluorescence spectrophotometer by monitoring Indo-1 excitation at 330 nm with detection of fluorescence emitted at 405 and 485 nm.

MPIF-1 preparations.

MPIF-1 protein preparations expressed in insect cells transfected with recombinant baculovirus (HG00300-B5, HG00300-B7 and HG14800-B1) were purified according to the invention. Proteins released into culture supernatants were purified and characterized with respect to N-terminal sequence. Preparation HG00300-B5 was found to contain RVTKDAET (SEQ ID NO:5) as the N-terminal amino acid sequence. In contrast, preparation HG00300-B7 was heterogenous with respect to N-terminal sequence (four N-truncated species). Preparation HG14800-B1 was from an alternate spliced cDNA construct. Preparation HG00302 was full length MPIF-1 with an additional methionine at the N-terminus and HG00304 was MPIF-1d23, a mutant lacking 23 N-terminal amino acids, were expressed in E. coli encoded by the cDNA constructs and purified according to the process of the present invention.

Results

Figure 20:
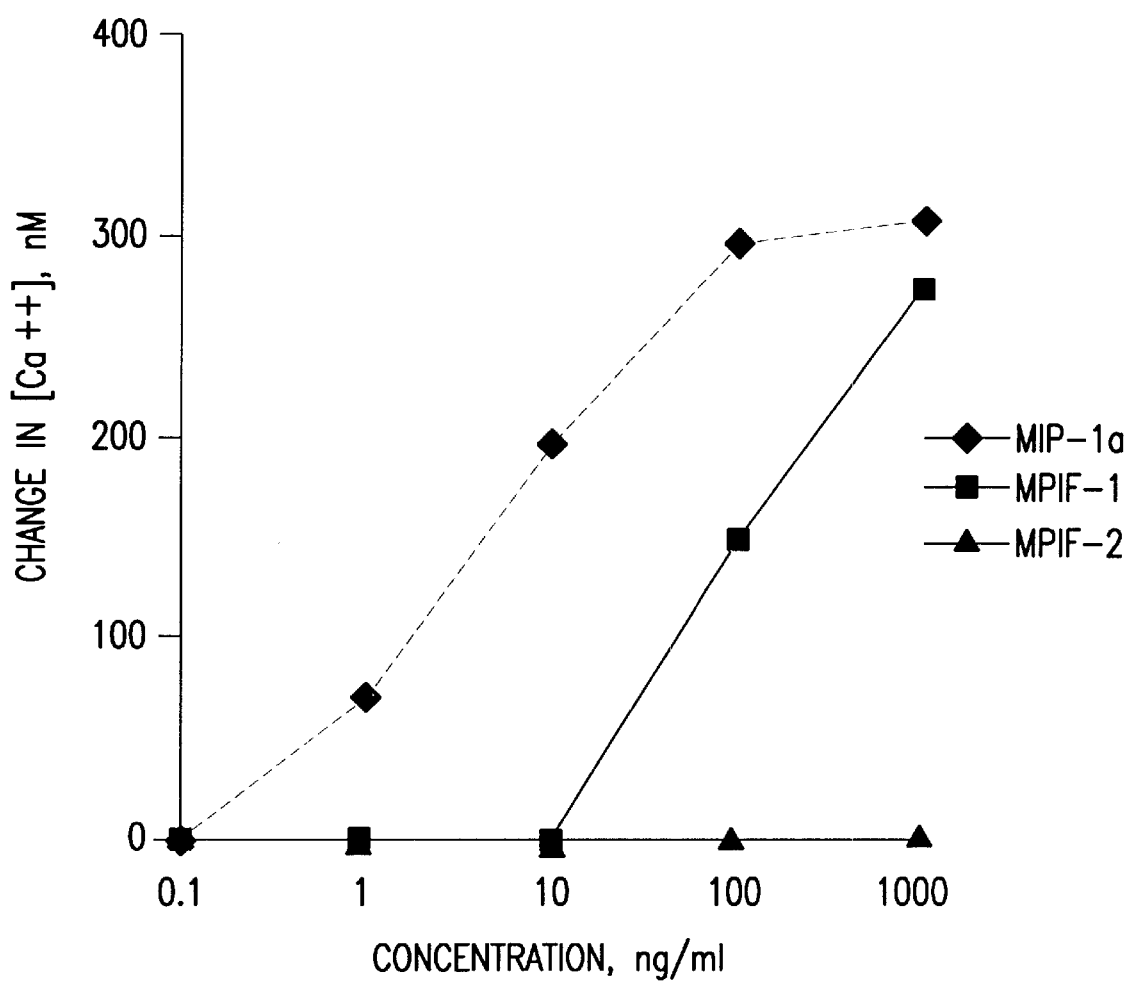
FIG. 20 shows calcium mobilization at various concentrations of MPIF-1, MPIF-2, MIP-1α in THP-1 cells. THP-1 cells loaded with Indo-1 were stimulated with various concentrations of MPIF-1, MPIF-2 and MIP-1α. The maximal changes in intracellular calcium concentration were measured.
Figure 21:
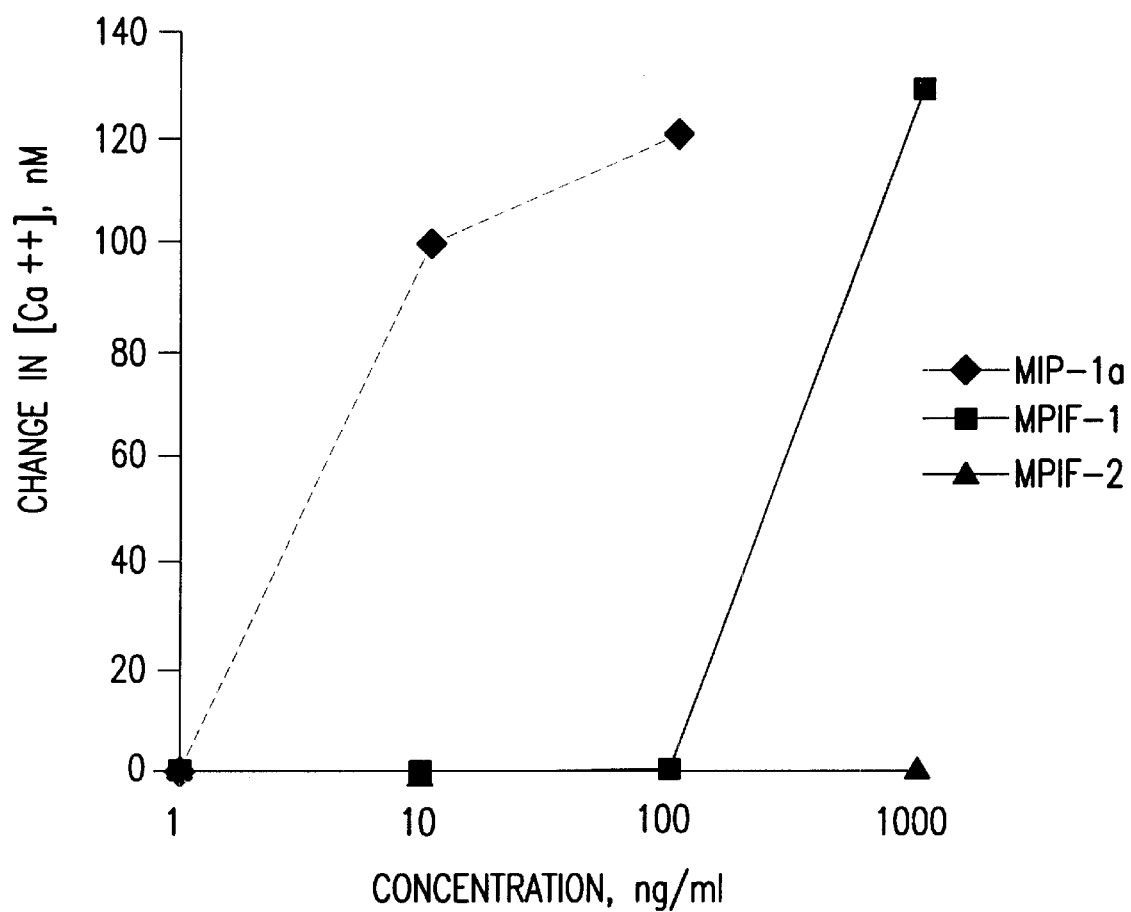
FIG. 21 shows calcium mobilization at various concentrations of MPIF-1, MPIF-2, MIP-1α in monocytes. Monocytes were stimulated with various concentrations of MPIF-1, MPIF-2 and MIP-1α.
Figure 22A:
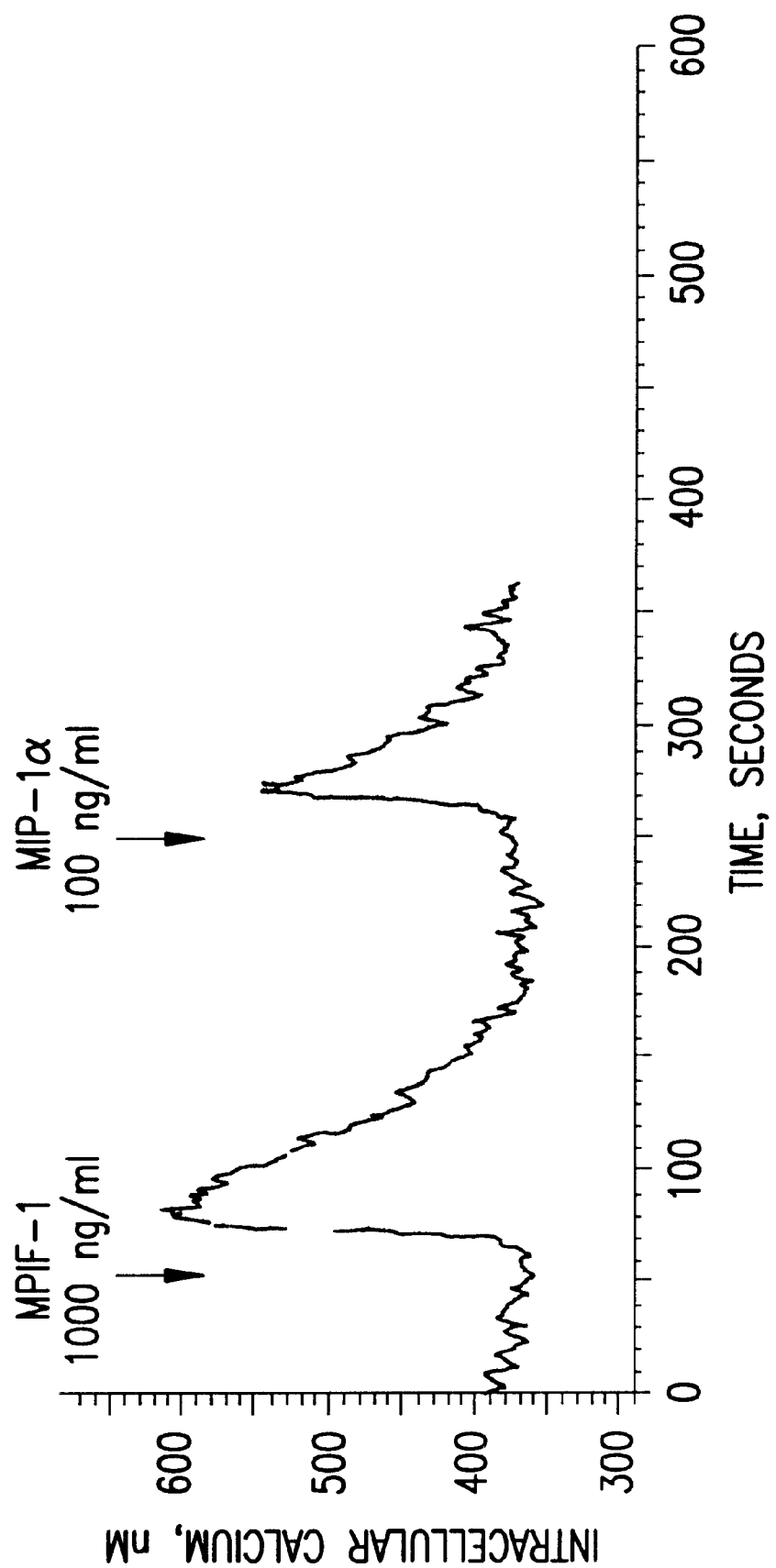
FIG. 22A and 22B show the desensitization of THP-1 cells by MPIF-1 and MIP-1α. The data shown in Panel A was obtained using THP-1 cells stimulated with MPIF-1 followed by MIP-1α. The data obtained in Panel B was obtained using THP- 1 cells stimulated with MIP-1αfollowed by MPIF-1.
Figure 22B:
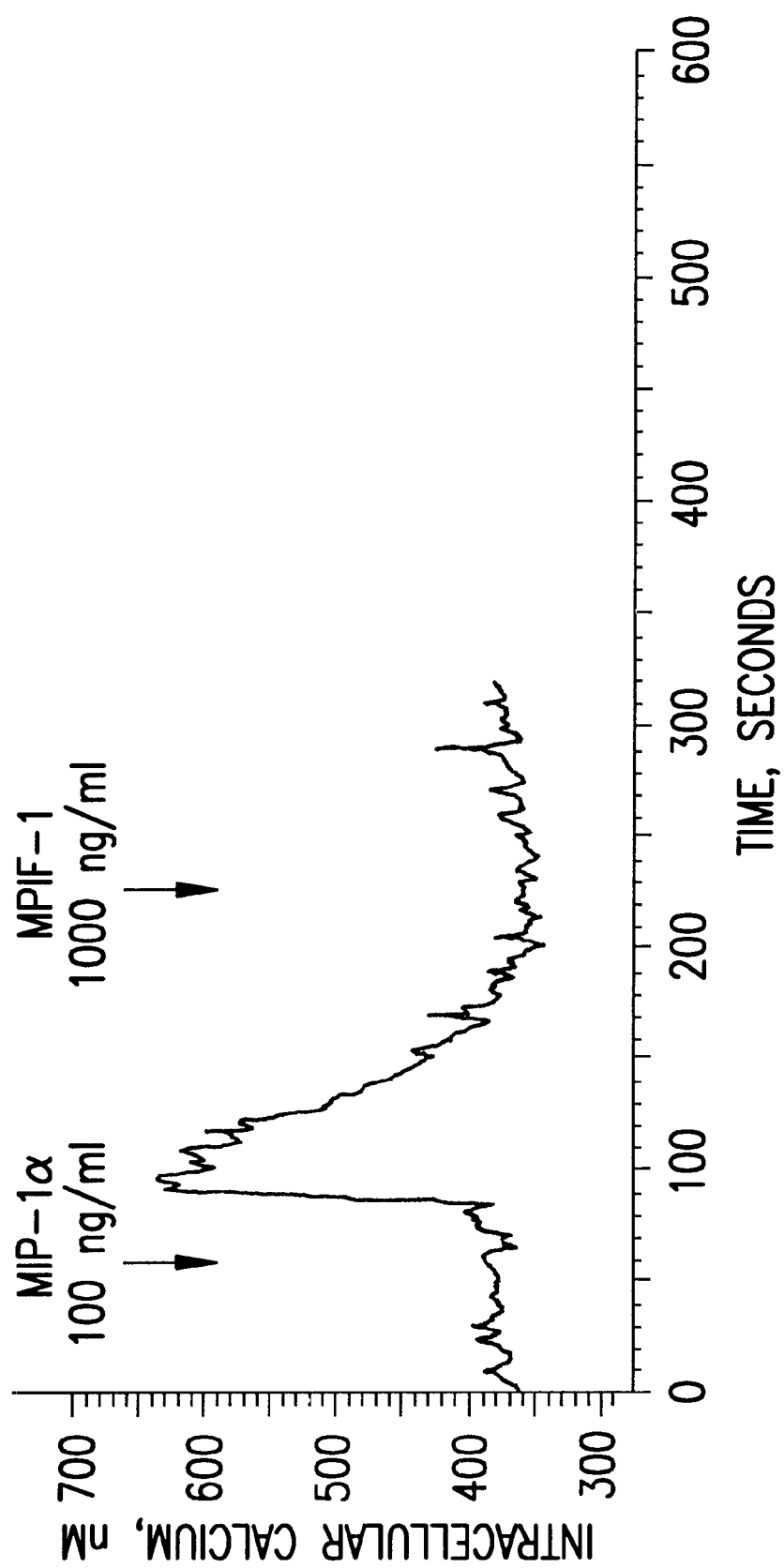
Figure 23A:
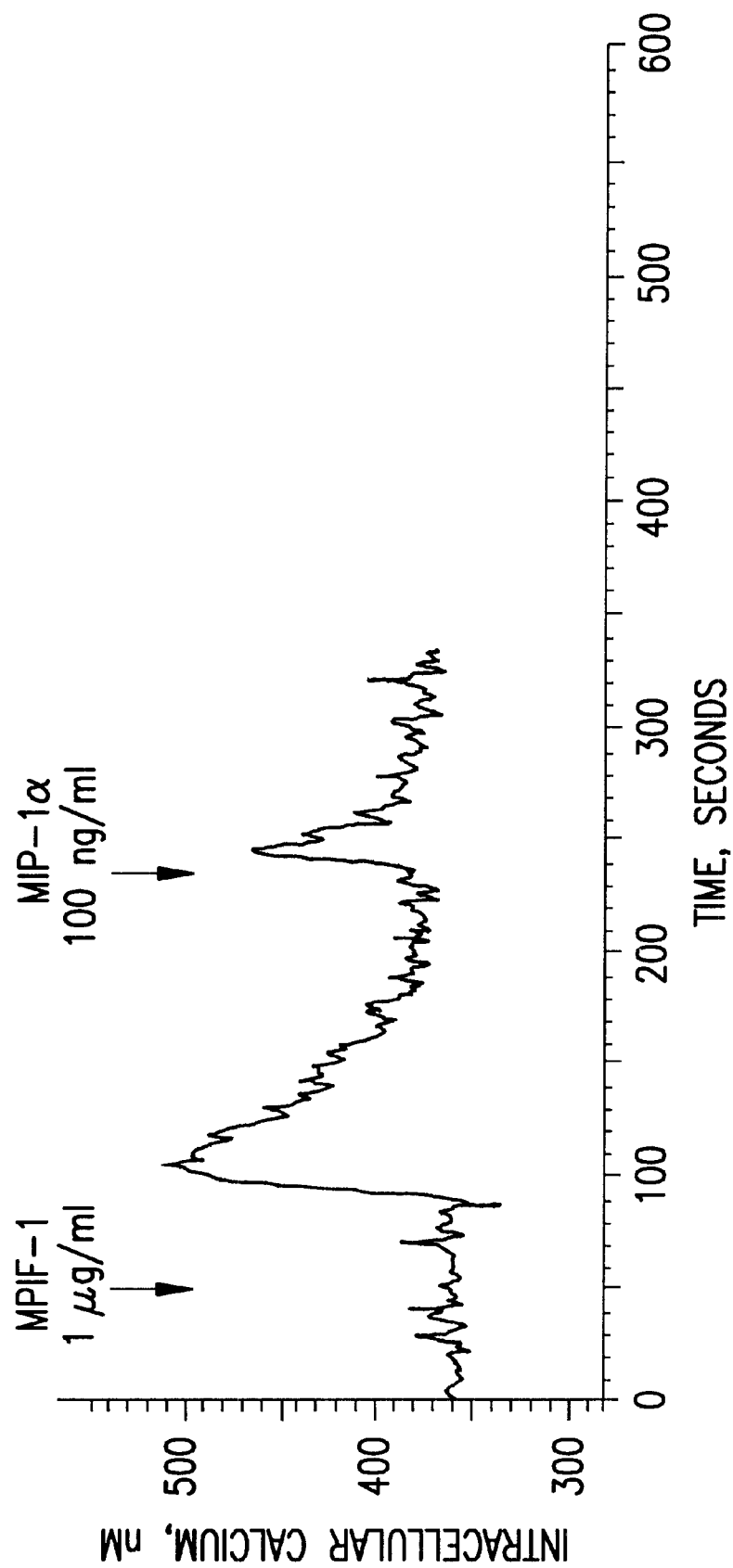
FIG. 23A and 23B show the desensitization of monocytes by MPIF-1 and MIP-1α. The data shown in Panel 23A was obtained using Monocytes stimulated with MPIF-1 followed by MIP-1α. The data shown in Panel B was obtained using Monocytes stimulated with MIP-1α followed by MPIF-1.
Figure 23B:
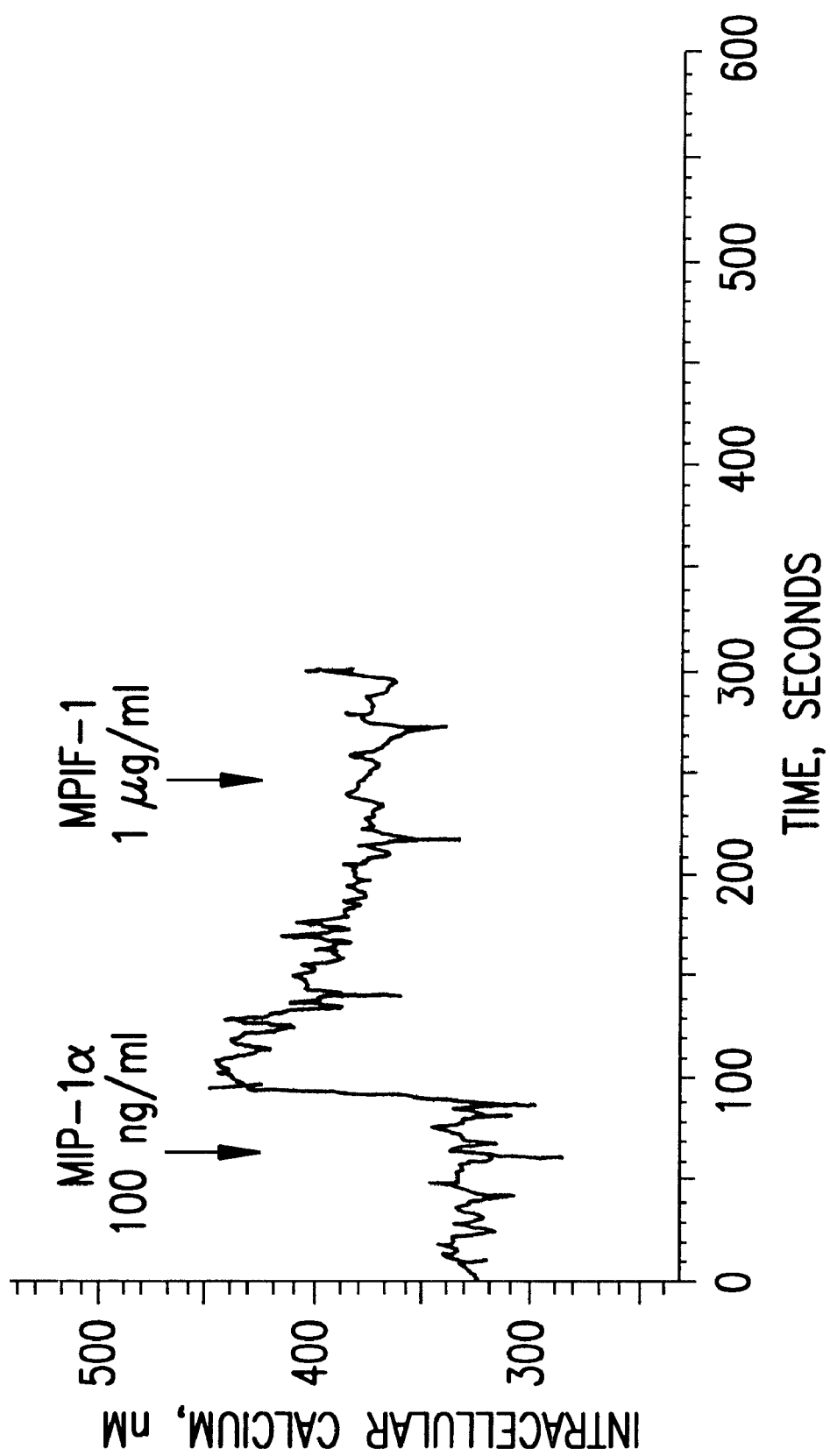

MPIF-1 purified according to the invention (HG00300-B5) induced a rapid calcium mobilization in THP-1 cells at a concentration of 100 ng/ml. Subsequently, we compared the effect of MIP-1α and MPIF-1 on calcium mobilization in THP-1 cells (FIG. 20) and monocytes (FIG. 21). The minimum concentrations of MIP-1α which stimulate calcium mobilization are 10 ng/ml and 1 ng/ml in the monocytes and THP-1 cells, respectively. MPIF-1 was about 10-fold less potent as compared with MIP-1α. Prior incubation of the THP-1 cells with 1000 ng/ml MPIF-1 prevented 50% of the subsequent response to 100 ng/ml MIP-1α (FIG. 22A and FIG. 22B). In contrast, the subsequent response to 1000 ng/ml MPIF-1 was abolished when the cells were first stimulated with 100 ng/ml MIP-1α. Similar desensitization results were obtained with monocytes (FIG. 23A and FIG. 23B). BB100.10 protein was identical to MIP-1α except for a difference of one amino acid at position 26 from Asp to Ala.

The effects of various MPIF-1 proteins from different cDNA constructs on monocytes and THP-1 cells are summarized in Table 10 and Table 11, respectively. The order or potency is HG00300-B7 >HG00304>HG00302. Thus, the N-terminal truncated MPIF-1 proteins seem to be more active than the full length MPIF-1 protein.

TABLE 10

EFFECTS OF VARIOUS MPIF-1 PROTEINS ON CALCIUM MOBILIZATION IN THP-1 CELLS

| Date | ng/ml | 00300-B5 | 00300-B7 | Change in $Ca^{++}$ nM 00302-E1 | 00302-E2 | 00304-E1 | 00304-E2 |
|---|---|---|---|---|---|---|---|
| 7/19/95 | 100 | 140 | | | | | |
| | 1,000 | | | | | | |
| 8/1/95 | 100 | 150 | | | | | |
| | 1,000 | | | | | | |
| 8/18/95 | 100 | 150 | | | | | |
| | 1,000 | | | | | | |
| 4/29/96 | 100 | | 50 (21%) | 240 (100%) | 70 (29%) | | |
| | 1,000 | | 190 (79%) | 230 (96%) | 200 (83%) | | |
| 5/1/96 | 100 | | | 170 (106%) | | | |
| | 1,000 | | | | | | |
| 5/6/96 | 100 | | | 170 (113%) | 100 (56%) | | |
| | 1,000 | | | 200 (133%) | | | |

TABLE 10-continued

EFFECTS OF VARIOUS MPIF-1 PROTEINS ON
CALCIUM MOBILIZATION IN THP-1 CELLS

| Date | ng/ml | 00300-B5 | 00300-B7 | Change in Ca$^{++}$ nM 00302-E1 | 00302-E2 | 00304-E1 | 00304-E2 |
|---|---|---|---|---|---|---|---|
| 6/24/96 | 10 | | | | | | |
| | 100 | | 130 (72%) | 50 (28%) | 40 (22%) | 100 (56%) | 80 (44%) |
| | 1,000 | | 170 (95%) | 80 (44%) | 80 (44%) | 130 (72%) | 130 (72%) |

The number in parentheses represent percentage of MIP-1α (100 ng/ml) response

TABLE 11

EFFECTS OF VARIOUS MPIF-1 PROTEINS ON
CALCIUM MOBILIZATION IN MONOCYTES

| Date | ng/ml | 00300-B7 | 00302-E1 | Change in Ca$^{++}$ nM 00302-E2 | 00302-E1 | 00304-E2 | BB100.10 | CKB8-AS |
|---|---|---|---|---|---|---|---|---|
| May 23, 1996 | 10 | 170 (155%) | | | | | 110 (E1) (100%) | |
| | 100 | 210 (190%) | 40(36%) | | | | 200 (182%) | |
| | 1,000 | 220 (200%) | 100(91%) | | | | 220 (200%) | |
| Jun. 10, 1996 | 100 | 200 (133%) | | | | | 160 (107%) | |
| Jun. 13, 1996 | 10 | | | | | | | 100(56%) |
| | 100 | | | | | | | 140(78%) |
| | 1,000 | | | | | | | 160(89%) |
| Jun. 18, 1996 | 10 | | | | | | | |
| | 100 | | 200 (100%) | 0 | 70(35%) | 60(30%) | | |
| | 1,000 | | | 80(40%) | 120(60%) | 140(70%) | | |
| Jun. 20, 1996 | 10 | 90 (53%) | 60(35%) | | | | 20(12%) | |
| | 100 | 210 (123%) | 140(82%) | | | | 140(82%) | |
| | 1000 | 250 (147%) | 140(82%) | 0 | | | 130(77%) | |
| Jun. 25, 1996 | 10 | 160 (89%) | | | | | 80(45%) | |
| | 100 | 200 (111%) | 0 | 0 | 50(28%) | 50(28%) | 170(94%) | |
| | 1,000 | 230 (128%) | 0 | 60(33%) | 180 (100%) | 190 (105%) | 270 (150%) | |

The numbers in parentheses represent percentage of MIP-1α or CKB10 (100 ng/ml) response Effect of MPIF-1 on the chemotaxis of peripheral leukocytes Chemotaxis refers to the migration of a given cell type in response to a soluble factor. Upon bacterial infection or tissue insult, a number of chemotactic factors are released from the vascular endothelial cells as well as from the responding immune cells. These factors are thought to be involved in the recruitment of immune cells to the site of injury or infection and thus play critical roles in host immune response. In addition, these chemotactic agents most likely play a role in the normal trafficking of a variety of immune cell types. MPIF-1 purified according to the present invention was examined for its chemotactic activity or peripheral blood mononuclear cells (PBMCs), neutrophils (PMNs), monocytes, and purified T-lymphocytes as described in the methods section.

Method

Primary Cell Isolation:

Cell types used for the chemotaxis assay include peripheral blood mononuclear cells (PBMCs), T-lymphocytes, peripheral multi-nucleated cells (PMNs or neutrophils), and monocytes. Peripheral blood mononuclear cells were purified from donor leukopacks (Red Cross) by centrifugation on lymphocyte separation medium (LSM; density 1.077 g/ml; Organon Teknika Corp.) and harvesting the interface band. Neutrophils were recovered from the pellet following a dextran sedimentation step either prior to or after ficoll separation. Monocytes were purified by centrifugal elutriation and T-lymphocytes were purified from the PBMCs using T-cell enrichment columns (R&D Systems).

Chemotaxis assay:

Cells used for the assay were washed 3X with HBSS/ 0.1% BSA and resuspended at 2×10$^6$/ml for labeling. Calcein-AM (Molecular Probes) was added to a final concentration of 1 μM and the cells incubated at 37° C. for 30 minutes. Following this incubation, the cells were washed 3X with HBSS/0.1% BSA. Labeled cells were resuspended at 4–8×10$^6$/ml and 25 μu (1–2×10$^5$ cells) added to the top of a polycarbonate filter (5–8 μm pore size, PVP free; NeuroProbe, Inc.) which separates the cell suspension from the chemotactic agent in the plate below. Cells were allowed to migrate for 45–90 minutes and then the number of migrated cells (both attached to the filter as well as in the bottom plate) was quantitated using a Cytofluor II fluorescence plate reader (PerSeptive Biosystems).

Results

Figure 24:
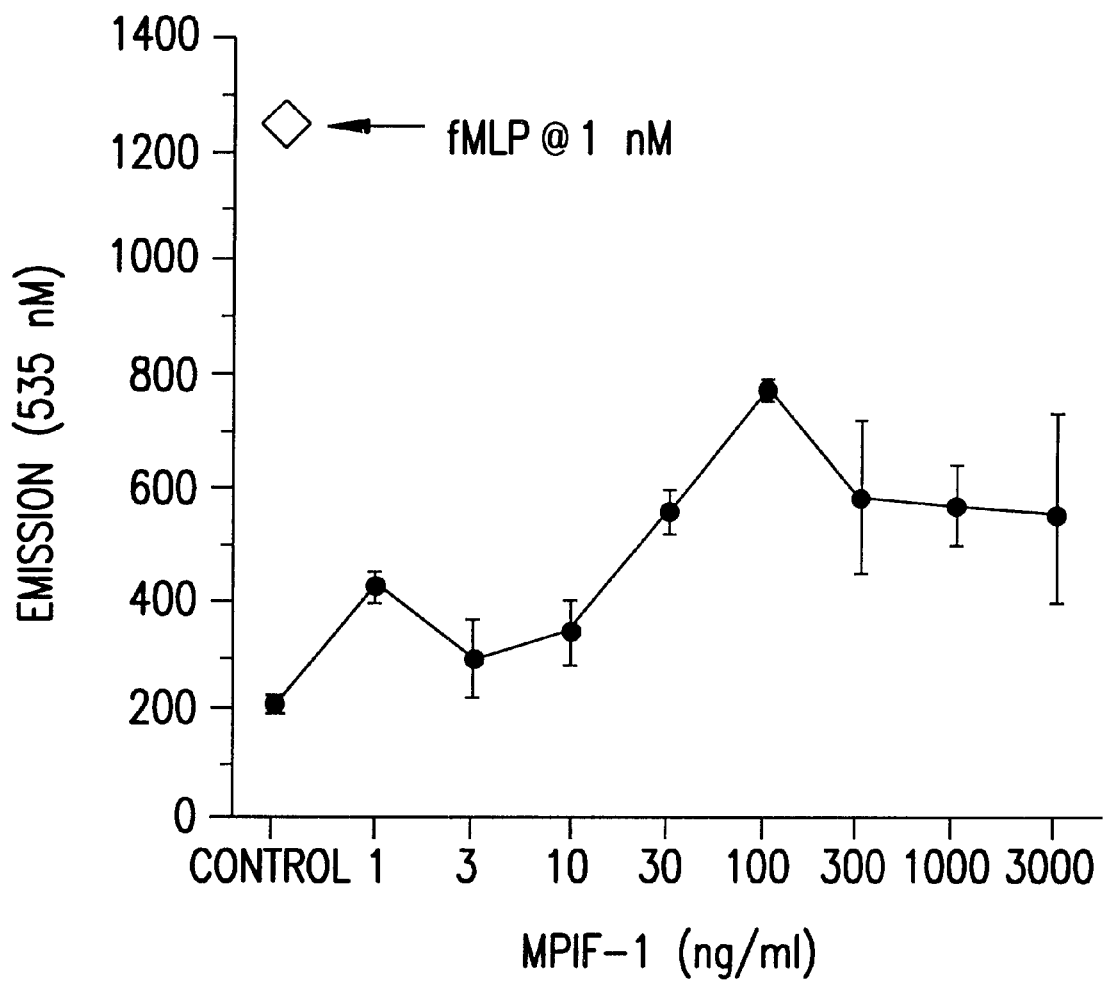
FIG. 24 shows the effect of MPIF-1 chemotaxis on PBMCs.
Figure 25:
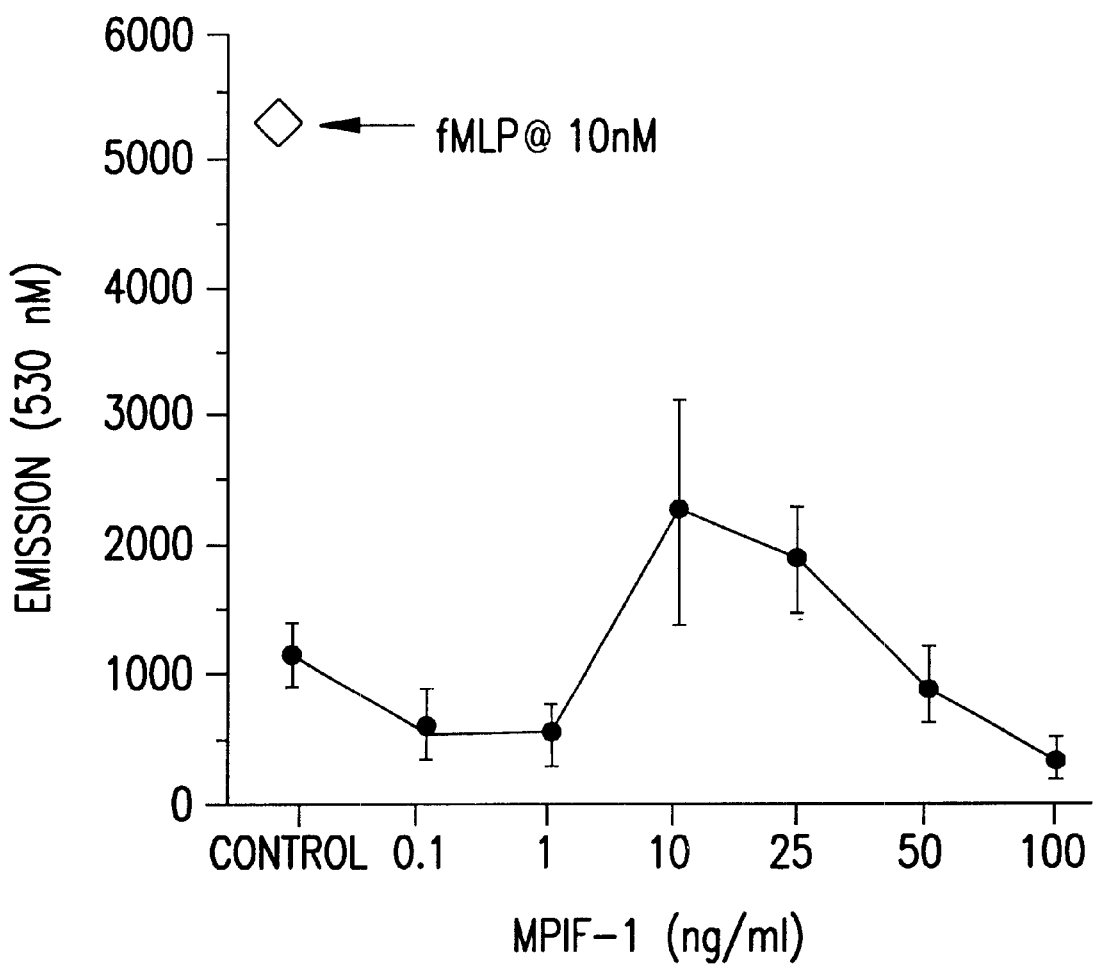
FIG. 25 shows the effect of MPIF-1 chemotaxis on neutrophils.

MPIF-1 purified according to the present invention had chemotactic activity on PBMCs in a dose range between 30–100 ng/ml with a chemotactic index (C.I.) ranging from 2–4 times the background values. FMLP served as a positive control in these assays and typically had a C.I. of 4–6 times background values. A representative experiment with PBMCs is shown in FIG. 24. MPIF-1 also showed chemotactic activity in assays with PMNs (FIG. 25) but this activity was weak (C.I.=2) and not always consistent. fMLP typically had a C.I. of 6–10 on PMNs and IL-8 typically showed a C.I. of 8–12 in this assay.

Figure 26:
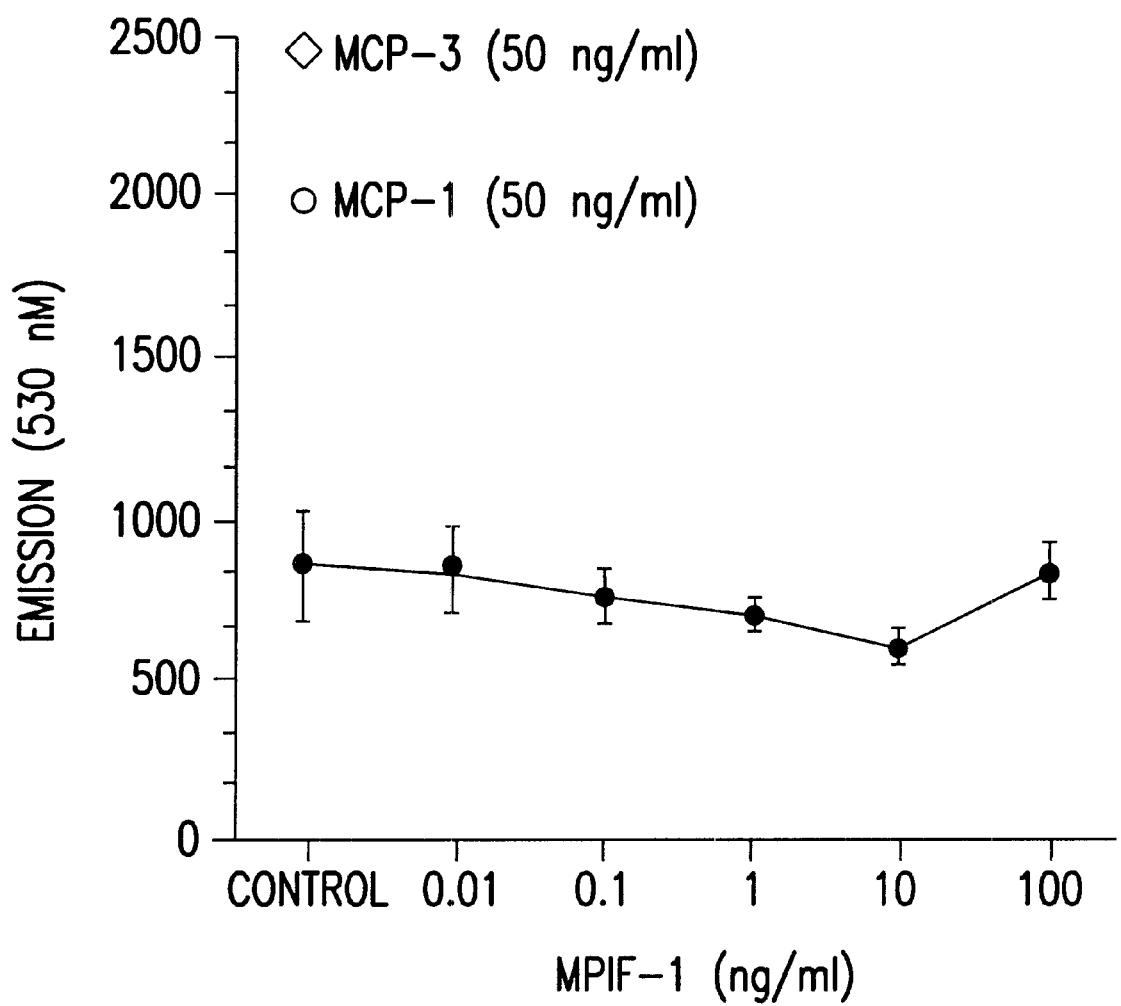
FIG. 26 shows the effect of MPIF-1 chemotaxis on monocytes.
Figure 27:
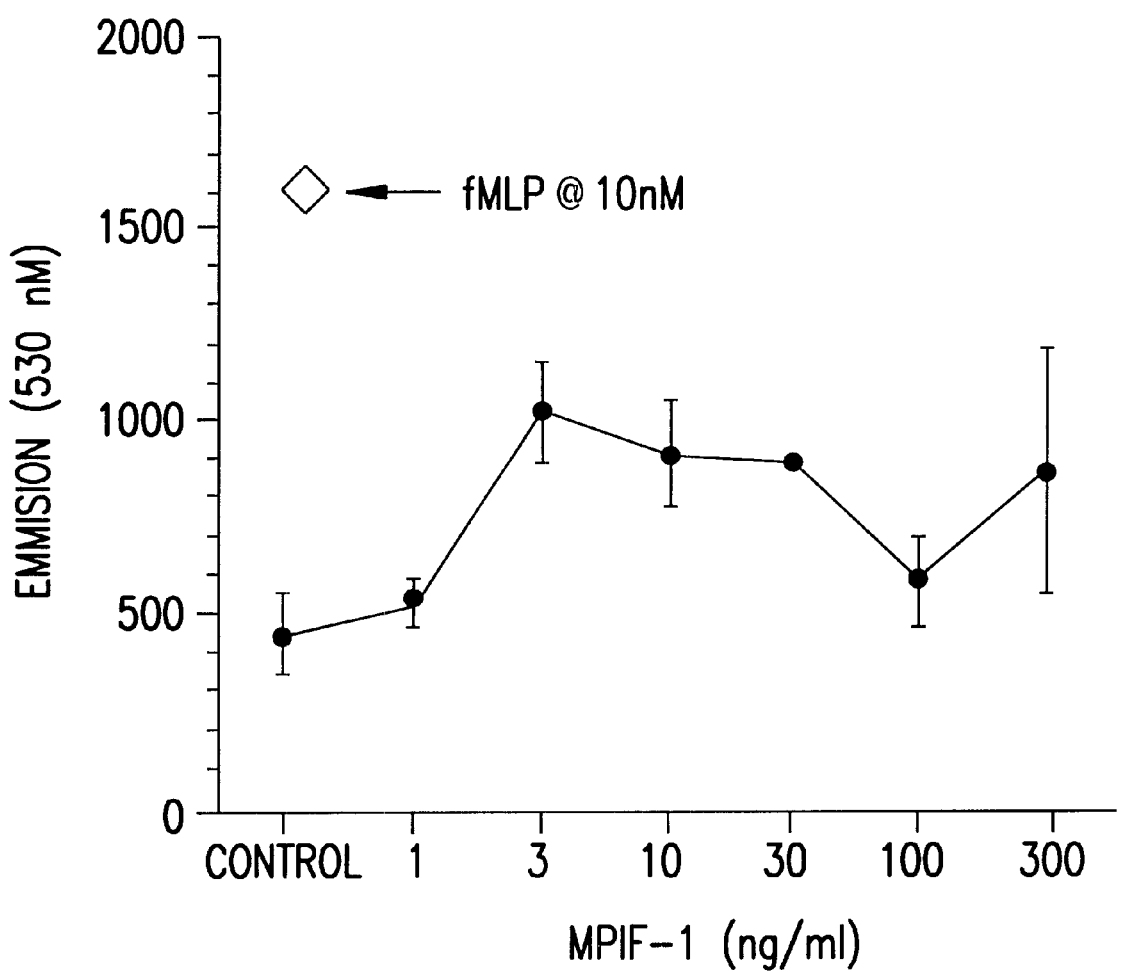
FIG. 27 shows the effect of MPIF-1 chemotaxis on T-lymphocytes.

The PBMC population was further fractionated into T-lymphocytes and monocytes and the purified populations used for chemotaxis assays. As shown in FIG. 26, MPIF-1 showed no chemotactic activity on purified monocytes. In contrast, MPIF-1 had chemotactic activity on the purified T-lymphocyte population (FIG. 27). This activity was similar to that seen with PBMCs but was evident at lower MPIF-1 concentrations (3–30 ng/ml) and with a lower C.I. (2–3 versus 2–4).

Conclusions

MPIF-1 purified according to the present invention retains its biological activity as a potent and specific inhibitor of a myeloid progenitor that gives rise to colonies composed of both granulocyte and monocyte lineage cells in vitro. This inhibition appears to be reversible in nature, as MPIF-1 purified according to the present invention was able to partially protect these progenitors from 5-Fu-induced cytotoxicity in vitro as well as in vivo. MPIF-1 was 10-fold less potent as compared with the same dose of MIP-1α inducing calcium mobilization in the monocytes and THP-1 cells. MPIF-1 and MIP-1α showed bi-directional cross desensitization indicating that they share a common receptor. MPIF-1 also shows chemotactic activity on an unfractionated population of PBMCs as well as a more purified population of T-lymphocytes. MPIF-1 has weak chemotactic activity on PMNs and shows no chemotactic activity on purified monocytes.

MPIF-1 Mutants

MPIF-1 N-terminal deletion mutants were also expressed and purified according to the present invention from baculovirus, E. coli and CHO expression systems. These mutants were also tested for biological activity. Particularly, MPIF-1d23 (HG00304), a mutant having 23 N-terminal amino acids deleted, was purified from E. coli. This protein was found to be more potent in calcium mobilization assays with THP-1 cells and monocytes. In addition, this protein was 10-fold more potent in LPP-CFC inhibition and protection of myeloid progenitors from 5-Fu-induced cytotoxicity. MPIF-1d23 was also found to be more active in animal experiments.

It will be clear that the invention may be practiced otherwise than as particularly described in the foregoing description and examples.

Numerous modifications and variations of the present invention are possible in light of the above teachings and, therefore, are within the scope of the appended claims.

The disclosures of U.S. application Ser. Nos. 08/722,719, now U.S. Pat. No. 6,001,606, and 08/722,723, now abandoned, are incorporated by reference.

TABLE 6

Effect of MPIF-1 on the murine hematopoietic progenitor cell colony formation in vitro in response to known cytokines

| Additions | CFU-E | BFU-E | Progenitor Colonies CFU-GM | HPP-CFC | LPP-CFC |
|---|---|---|---|---|---|
| Cytokine Cocktail (CC) | 94 ± 10 | 13 ± 2.5 | 29 ± 3.0 | 35 ± 4.0 | 114 ± 12 |
| CC + MPIF-1 (50 ng/ml) | 89 ± 11 | 12 ± 2.0 | 11 ± 2.0 | 29 ± 2.0 | 27 ± 6.0 |
| CC + MCP-4 (50 ng/ml) | 91 ± 11 | 12 ± 3.0 | 31 ± 4.0 | 34 ± 2.0 | 116 ± 17 |

The effect of MPIF-1 on the growth and the differentiation of the hematopoietic progenitors was examined in an clonogenic assay as described in the Materials and Methods. Also shown here is the colony formation response to another chemokine (CKB-10) which was expressed and purified as MPIF. Growth of CFU-E, BPU-E & CFU-GM was assayed by plating 5 × 10$^4$ bone marrow cells in amethylcellulose-containing growth medium that was supplemented either with rh Epo. (for CFU-E) or rmIL-3 + rh Epo. + rm GM-CSF (for BFU-E & CFU-GM). Colony formation by HPP-CFC and LPP-CFC was assayed by plating 1,500 bone marrow cells in a soft-agar medium as described in the Materials and Methods. Data shown are pooled from two separate experiments and are expressed as Mean ± S.D.

TABLE 7

Effect of MPIF-1 administration to mice on the Hematopoietic Progenitor Frequencies in the Peripheral Blood and Bone Marrow

| | Peripheral Blood | | Bone Marrow | |
|---|---|---|---|---|
| Treatments | HPP-CFC (per 1 × 10$^4$) | LPP-CFC | HPP-CFC (per 2 × 10$^3$) | LPP-CFC |
| Saline | 0 | 21 ± 7.2 | 11.8 ± 2.3 | 88 ± 11 |
| MPIF-1 | 0 | 15 ± 5.3* | 13 ± 3.1 | 67 ± 12# |

*The two-tailed P value derived from unpaired t-test is 0.0690, which is considered not significant.
Here the two-tailed P value derived as above is 0.0033, considered very significant.

TABLE 8

Effect of MPIF-1 Pre-treatment of mice on the 5-Fu induced reduction in the circulating WBC counts

| | Numbers of Circulating WBC per Milliliter of Blood | | |
|---|---|---|---|
| Treatments | Day 3 | Day 6 | Day 10 |
| Gr-1 (Saline) | 8.4 × 10$^6$ ± 3.0 × 10$^6$ | 10.2 × 10$^6$ ± 3.6 × 10$^6$ | 7.0 × 10$^6$ ± 9.9 × 10$^5$ |
| Gr-2, MPIF-1 alone | 7.8 × 10$^6$ ± 2.2 × 10$^6$ (100%) | 7.5 × 10$^6$ ± 6.5 × 10$^5$ (100%) | 10.6 × 10$^6$ (100%) |

TABLE 8-continued

Effect of MPIF-1 Pre-treatment of mice on the 5-Fu induced reduction in the circulating WBC counts

| Treatments | Numbers of Circulating WBC per Milliliter of Blood | | |
|---|---|---|---|
| | Day 3 | Day 6 | Day 10 |
| Gr-3,5-Fu alone | $4.23 \times 10^6 \pm 2.8 \times 10^6$ (54) | $1.8 \times 10^6 \pm 1.4 \times 10^4$ (24) | $8.8 \times 10^6 \times 4.9 \times 10^5$ (83) |
| G4-4, MPIF-1 plus 5-Fu | $3.49 \times 10^6 \pm 6.5 \times 10^5$ (45) | $3.98 \times 10^6 \pm 4.3 \times 10^5$ (53) | $9.48 \times 10^6 \pm 9.4 \times 10^5$ (89) |

Data from one out of three representative experiments are shown above and are expressed as Mean numbers of WBC/milliliter of blood ± S.D.

TABLE 9

Effect of MPIF-1 administration to mice prior to the second dose of 5-Fu on various hematopoietic parameters

| Treatments | 3 Days post second 5-Fu | | | | 7 Days post second 5-Fu | | | |
|---|---|---|---|---|---|---|---|---|
| | WBC* | BMC# | HPP-CFC** | LPP-CFC** | WBC | BMC | HPP-CFC | LPP-CFC |
| Saline | 8.1 ±2.0 | 17.8 ±4.4 | 14.6 ±1.3 | 102 ±6.4 | 7.5 ±2.0 | 18.6 ±2.6 | 16.5 ±3.0 | 97.5 ±8.5 |
| 5-Fu | 3.7 ±0.7 | 2.27 ±1.4 | 3.8 ±1.0 | 2.8 ±1.0 | 2.6 ±2.0 | 2.6 ±1.4 | 6.0 ±2.0 | 37 ±2.8 |
| 5-Fu plus MPIF-1 | 4.7 ±0.8 | 1.2 ±0.15 | 5.5 ±2.1 | 14.8 ±2.8 | 3.9 ±0.2 | 5.0 ±1.5 | 16.8 ±1.5 | 98 ±7.4 |

Data from one out of three representative experiments are shown above and are expressed as Mean ± S.D. with n equals 4 animals per time point.
* $\times 10^6$ WBC/ml blood
$\times 10^6$ Bone marrow cellularity (BMC)
**Colonies/600 bone marrow cells

What is claimed is:

1. A composition comprising a biologically active chemokine and a buffer at pH 4.5, wherein said chemokine is selected from the group consisting of myeloid progenitor inhibitory factor (MPIF-1) and myeloid progenitor inhibitory factor-1 having the N-terminal 23 amino acids deleted (MPIF-1d23).

2. The composition of claim 1, wherein said chemokine is myeloid progenitor inhibitory factor-1 (MPIF-1).

3. The composition of claim 1, wherein said chemokine is myeloid progenitor inhibitory factor-1 from which the N-terminal 23 amino acids are deleted (MPIF-1d23).

4. The composition of claim 2, wherein said chemokine is about 70% pure.

5. The composition of claim 3, wherein said chemokine is about 70% pure.

6. The composition of claim 2, wherein said buffer comprises 50 to 100 mM sodium acetate at a pH of 4.5, 150 mM sodium chloride, and 2 mM EDTA.

7. The composition of claim 3, wherein said buffer comprises 50 to 100 mM sodium acetate at a pH of 4.5, 150 mM sodium chloride, and 2 mM EDTA.

8. A composition comprising a soluble chemokine in a solution containing a chaotropic agent at a concentration of about 0.7 M to about 3.5 M, wherein said chemokine is selected from the group consisting of myeloid progenitor inhibitory factor (MPIF-1) and myeloid progenitor inhibitory factor-1 having the N-terminal 23 amino acids deleted (MPIF-1d23), and wherein said chaotropic agent is selected from the group consisting of guanidine isothiocyanate and urea.

9. The composition of claim 8, wherein said chemokine is myeloid progenitor inhibitory factor-1 (MPIF-1).

10. The composition of claim 8, wherein said chemokine is myeloid progenitor inhibitory factor-1 from which the N-terminal 23 amino acids are deleted (MPIF-1d23).

11. The composition of claim 8, wherein said chaotropic agent is present at a concentration of about 1 M to about 2 M.

12. The composition of claim 9, wherein said chaotropic agent is guanidine isothiocyanate.

13. The composition of claim 9, wherein said chaotropic agent is urea.

14. The composition of claim 9, wherein said chaotropic agent is guanidine isothiocyanate.

15. The composition of claim 10, wherein said chaotropic agent is urea.

* * * * *

UNITED STATES PATENT AND TRADEMARK OFFICE
CERTIFICATE OF CORRECTION

PATENT NO. : 6,632,425 B1
DATED : October 14, 2003
INVENTOR(S) : Li et al.

It is certified that error appears in the above-identified patent and that said Letters Patent is hereby corrected as shown below:

Column 42,
Line 30, delete "claim 9," and insert -- claim 10, --.

Signed and Sealed this

Second Day of March, 2004

JON W. DUDAS
*Acting Director of the United States Patent and Trademark Office*